United States Patent [19]
Eaton et al.

[11] Patent Number: 6,048,698
[45] Date of Patent: Apr. 11, 2000

[54] PARALLEL SELEX™

[75] Inventors: Bruce Eaton; Theodore M. Tarasow, both of Boulder, Colo.

[73] Assignee: NeXstar Pharmaceuticals, Inc., Boulder, Colo.

[21] Appl. No.: 09/157,601

[22] Filed: Sep. 21, 1998

Related U.S. Application Data

[63] Continuation-in-part of application No. 08/618,700, Mar. 20, 1996, Pat. No. 5,858,660, which is a continuation-in-part of application No. 08/309,245, Sep. 20, 1994, Pat. No. 5,723,289.

[51] Int. Cl.⁷ .............................. C12Q 1/68; C07H 21/02; C07H 21/04
[52] U.S. Cl. ................................. 435/6; 536/25.4
[58] Field of Search .................. 435/6; 536/25.4

[56] References Cited

U.S. PATENT DOCUMENTS

| | | | |
|---|---|---|---|
| 4,605,735 | 8/1986 | Miyoshi et al. | 536/22.1 |
| 4,794,073 | 12/1988 | Dattagupta et al. | 435/6 |
| 4,968,602 | 11/1990 | Dattagupta | 435/6 |
| 5,270,163 | 12/1993 | Gold et al. | 435/6 |
| 5,288,514 | 2/1994 | Ellman | 435/6 |
| 5,506,337 | 4/1996 | Summerton et al. | 435/6 |
| 5,541,061 | 7/1996 | Fodor et al. | 435/6 |
| 5,565,324 | 10/1996 | Still et al. | 435/6 |
| 5,571,681 | 11/1996 | Janda | 435/6 |
| 5,573,905 | 11/1996 | Lerner et al. | |
| 5,593,853 | 1/1997 | Chen et al. | |
| 5,723,289 | 3/1998 | Eaton et al. | |
| 5,723,592 | 3/1998 | Eaton et al. | |

FOREIGN PATENT DOCUMENTS

| | | |
|---|---|---|
| 2 183 661 | 6/1987 | United Kingdom . |
| WO 89/06694 | 7/1989 | WIPO . |
| WO 91/14696 | 10/1991 | WIPO . |
| WO 91/19813 | 12/1991 | WIPO . |
| WO 92/14843 | 9/1992 | WIPO . |
| WO 95/16788 | 6/1995 | WIPO . |
| WO 96/06944 | 3/1996 | WIPO . |
| WO 96/17086 | 6/1996 | WIPO . |

OTHER PUBLICATIONS

Allinger et al. (1971) Organic Chemistry, Worth Publ., Inc., New York, NY p. 330.
Alper (1994) Science 264:1399.
Bartel and Szostak (1993) Science 261:1411.
Brenner and Lerner (1992) Pro. Natl. Acad. Sci. USA 89:5381.
Cech (1987) Science 236:1532.
Chung et al. (1994) Proc. Natl. Acad. Sci. USA 91:2372.
Ellington & Szostak (1990) Abstract of papers presented at the 1990 meeting on RNA Processing, Cold Spring Harbor Laboratory, Cold Spring Harbor, NY, p. 84.
Fodor et al. (1991) Science 251:767.
Joyce (1989) Gene 82:83.
Joyce and Inoue (1989) Nucleic Acids Research 17:711.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Longman (1994) In Vivo 23–31.
Lorsch and Szostak (1994) Nature 371:31.
McCorkle and Altman (1987) Journal of Chemical Education 64:221.

(List continued on next page.)

Primary Examiner—Stephanie W. Zitomer
Attorney, Agent, or Firm—Swanson & Bratschun, L.L.C.

[57] ABSTRACT

This invention discloses a method for coevolving products from two or more reactants, along with the nucleic acid that can facilitate the reaction for making the products. The invention further discloses the products and facilitating nucleic acids produced by said method.

27 Claims, 13 Drawing Sheets

OTHER PUBLICATIONS

Nagpal et al. (1990) Autoimmunity 8:59 (Abstract).
Needels et al. (1993) Proc. Natl. Acad. Sci. USA 90:10700.
Ohlmeyer et al. (1993) Proc. Natl. Acad. Sci. USA 90:10922.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Piccirilli et al. (1992) Science 256:1420.
Prudent et al. (1994) Science 264:1924.
Robertson and Joyce (1990) Nature 344:467.
Thiesen and Bach (1990) Nucleic Acids Research 18:3203.
Szostak, "Structure and Activity of Ribozymes," in *Redesigning the Molecules of Life*, (S.A. Benner ed.) Springer–Verlag Berlin Heidelberg, pp. 87–113, (1988).

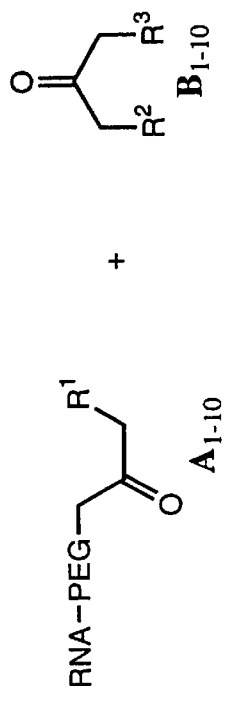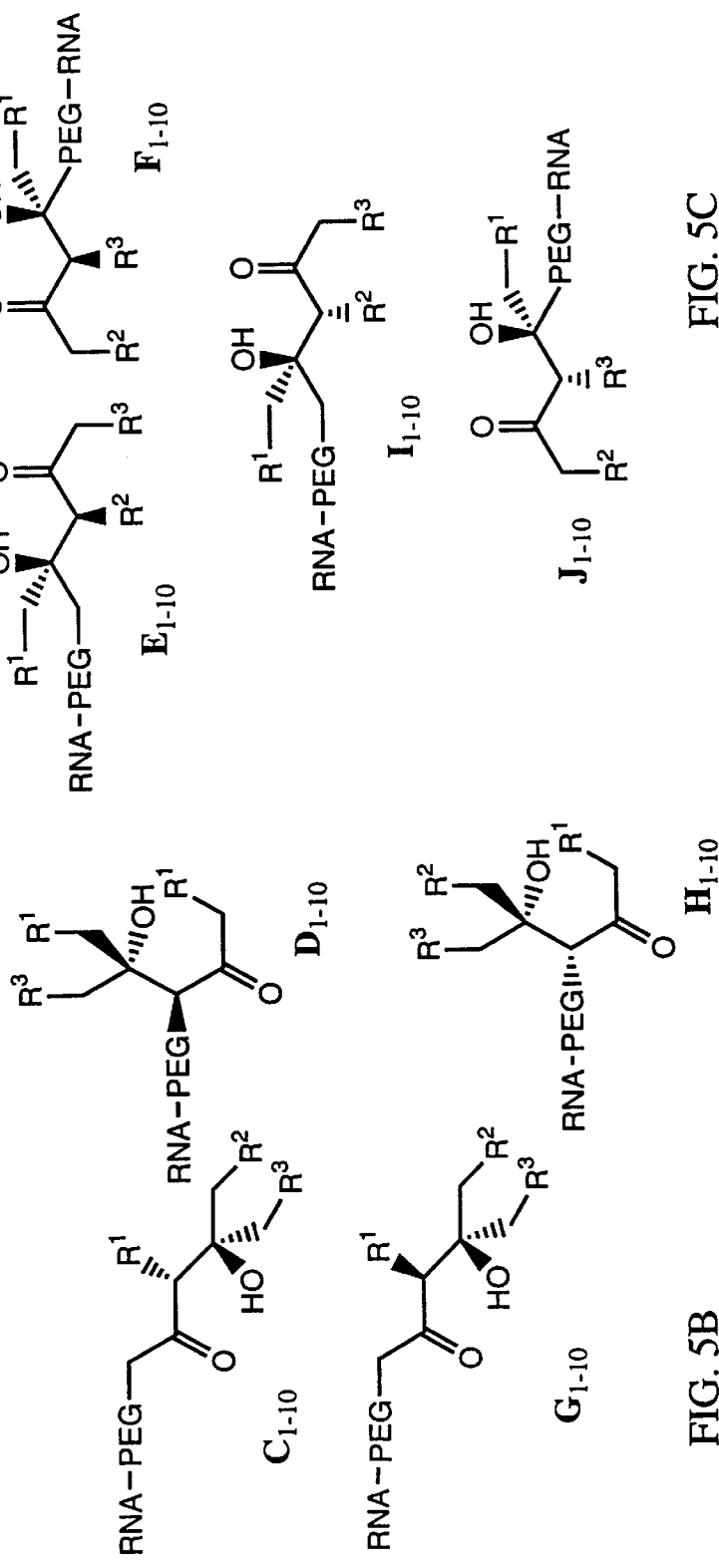
FIG. 5A  FIG. 5B  FIG. 5C

PARALLEL SELEX™

RELATED APPLICATIONS

This application is a Continuation-In-Part of U.S. patent application Ser. No. 08/618,700, filed Mar. 20, 1996, entitled "Parallel SELEX", now U.S. Pat. No. 5,858,660, which is a Continuation-In-Part of U.S. patent application Ser. No. 08/309,245, entitled "Parallel SELEX", filed Sep. 20, 1994, now U.S. Pat. No. 5,723,289.

FIELD OF THE INVENTION

This invention relates to methods for producing products from two or more reactants wherein the reaction, preferably bond formation, between the reactants is mediated by a nucleic acid having facilitating properties. Also included in the invention are the products made by the methods. More particularly, the invention relates to methods for coevolving a facilitating nucleic acid and the product that is assembled by the mediation of said facilitating nucleic acid. The invention further relates to a method for identifying nucleic acids having facilitative properties and said nucleic acids.

BACKGROUND OF THE INVENTION

A method for the in vitro evolution of nucleic acid molecules with highly specific binding to target molecules has been developed. This method, Systematic Evolution of Ligands by EXponential enrichment, termed SELEX™, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Methods for Identifying Nucleic Acid Ligands", now U.S. Pat. No. 5,270,163 (see also WO 91/19813), each of which is herein specifically incorporated by reference. Each of these applications, collectively referred to herein as the SELEX™ Patent Applications, describes a fundamentally novel method for making a nucleic acid ligand to any desired target molecule.

The SELEX™ method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX™ method demonstrates that nucleic acids as chemical compounds can form a wide array of shapes, sizes and configurations, and are capable of a far broader repertoire of binding and other functions than those displayed in biological systems.

The dogma for many years was that nucleic acids had primarily an informational role. Through the application of SELEX™ it has become clear to the present inventors that nucleic acids have three dimensional structural diversity not unlike proteins. As such, the present inventors have recognized that SELEX™ or SELEX™-like processes could be used to identify nucleic acids which can facilitate any chosen reaction in that nucleic acid ligands can be identified for any given target. In theory, within a candidate mixture of approximately $10^{13}$ to $10^{18}$ nucleic acids, the present inventors postulate that at least one nucleic acid exists with the appropriate shape to facilitate a broad variety of physical and chemical interactions.

Studies to date have identified only a few nucleic acids which have only a narrow subset of facilitating capabilities. A few RNA catalysts are known (Cech, 1987. *Science* 236:1532–1539 and McCorkle and Altman (1987) *J. Chem. Education* 64:221–226). These naturally occurring RNA enzymes (ribozymes) have to date only been shown to act on oligonucleotide substrates. Further, these molecules perform over a narrow range of chemical possibilities, which are thus far related largely to phosphodiester bond condensation/hydrolysis, with the exception of the possible involvement of RNA in protein biosynthesis. Despite intense recent investigation to identify RNA or DNA catalysts, few successes have been identified. Phosphodiester cleavage, hydrolysis of aminoacyl esters (Piccirilli et al., 1992. *Science* 256:1420–1424), ligation of an oligonucleotide with a 3' OH to the 5' triphosphate end of the catalyst (Bartel and Szostak, 1993. *Science* 261:1411–1418), amide bond cleavage (Dai et al., 1995. *Science* 267:237–40), biphenyl isomerase activity (Prudent et al., 1994. *Science* 264:1924–1927), and polynucleotide kinase activity (Lorsch and Szostak, 1994. *Nature* 371:31–36) have been observed. Illangasekare et al., (*Science.* (1995) 267:643–47) describe the first RNA molecules that catalyze a carbon-oxygen bond formation. The nucleic acid catalysts known to date have certain shortcomings associated with their effectiveness in bond forming/breaking reactions. Among the drawbacks are that they act slowly relative to protein enzymes, and as described above, they perform over a somewhat narrow range of chemical possibilities.

The basic SELEX™ method has been modified to achieve a number of specific objectives. For example, U.S. patent application Ser. No. 07/960,093, filed Oct. 14, 1992, entitled "Method for Selecting Nucleic Acids on the Basis of Structure", now abandoned (See also U.S. Pat. No. 5,707, 796) describes the use of SELEX™ in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands", now abandoned (See also U.S. Pat. No. 5,763,177) describes a SELEX™ based method for selecting nucleic acid ligands containing photoreactive groups capable of binding and/or photo-crosslinking to and/or photoinactivating a target molecule. Co-pending PCT Application Publication No. WO 95/08003, filed Sep. 19, 1994 which is a CIP of U.S. patent application Ser. No. 08/123,935, specifically incorporated by reference, discloses that certain nucleic acid sequences that contained 5-iodouracil residues were identified that covalently bind to HIV-1 Rev protein. U.S. patent application Ser. No. 08/134,028, filed Oct. 7, 1993, entitled "High-Affinity Nucleic Acid Ligands That Discriminate Between Theophylline and Caffeine", now abandoned (See also U.S. Pat. No. 5,580,737) describes a method for identifying highly specific nucleic acid ligands able to discriminate between closely related molecules, termed Counter-SELEX™. U.S. patent application Ser. No. 08/143,564, filed Oct. 25, 1993, entitled "Systematic Evolution of Ligands by EXponential Enrichment: Solution SELEX™", now abandoned (See also U.S. Pat. No. 5,567,588) describes a SELEX™-based method which achieves highly efficient partitioning between oligonucleotides having high and low affinity for a target molecule. U.S. patent application Ser. No. 08/400,440, filed Mar. 8, 1995 entitled "Systematic Evolution of Ligands by Exponential Enrichment: Chemi-SELEX™," now U.S. Pat. No. 5,705,337, describes methods for covalently linking a nucleic acid ligand to its target.

The SELEX™ method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", now abandoned (See also U.S. Pat. No. 5,660,985) that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", now abandoned, describes oligonucleotides containing various 2'-modified pyrimidines.

The SELEX™ method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX™", now U.S. Pat. No. 5,637,459, and U.S. patent application Ser. No. 08/234,997, filed Apr. 28, 1994, entitled "Systematic Evolution of Ligands by Exponential Enrichment: Blended SELEX™", now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX™ procedure are specifically incorporated by reference herein in their entirety.

Recently some attempts have been made to use combinatorial chemistry as a way to discover new drugs. A few elaborate schemes have been devised to produce combinatorial libraries having an array of different structures. The structures associated with known combinatorial libraries include nucleic acids as described previously for the SELEX™ process, peptides (Brenner, et al., 1992. *PNAS* 89:5381–5383; Needels, et al., 1993. *PNAS* 90:10700–10704; Alper, 1994. *Science* 264:1399–1401; Longman, 1994. *In Vivo* 23–31, Fodor et al., 1991. *Science* 251:767–773), and a much smaller number directed to small organic molecules (Ohlmeyer, et al., 1993. *PNAS* 90:10922–10926). There are certain drawbacks associated with each of the known combinatorial library approaches.

First, some of the schemes used for preparing peptide or small molecule combinatorial libraries require rigorous recordkeeping systems to keep track of which chemistries occurred at any point in the array/matrix. Moreover, peptides and small organic molecules are not amplifiable and therefore relatively large quantities of each individual product must be present in the library to enable testing and identification of desirable products. In order to obtain large enough quantities of specific products, the reactions that make up the array must be highly efficient. More importantly, for these approaches to work, it is not possible to have a mixture of products and side products at the same site in the array. Diversity is generated by polymeric combination of multiple steps, each of which consists of a single reaction with a predictable outcome. However, the extent of polymeric combination is limited by yield and recordkeeping constraints.

Another limitation of small molecule combinatorial approaches is that the schemes generally exclude bond formation reactions that produce new stereocenters by asymmetric reactions. By eliminating asymmetric reactions, these approaches do not provide chemical diversity that can be generated at a single step. Often, asymmetric reactions are difficult to control, so if reactions that form new chiral centers are included in the combinatorial scheme, it would be likely that racemic product mixtures would result. When more than one chiral center is present, diastereomeric product mixtures can result in background problems. For example, it is possible that the ideal atoms and groups are introduced for assembly, but that the chirality of the product is crucial to the desired properties and the correct enantiomer is only present as a small percentage of the total. In this example, it is quite likely that the correct enantiomer will not be made in a quantity sufficient to be identified. Further, it is impossible to accurately predict the chirality of each individual reaction when a large array of reactants is included in an asymmetric transformation. Therefore, it is unlikely that the difficulty associated with racemic mixtures can be overcome by traditional means. The labor and time necessary to include asymmetric catalysis in conventional combinatorial library approaches is generally impractical. Therefore, asymmetric reactions are generally excluded to circumvent the described problems.

Nevertheless, asymmetric reactions include one of the most powerful of all bond forming reaction types. The absence of asymmetric reactions in combinatorial library approaches significantly limits the types of products that can be made and the breadth of the library. The following example illustrates the immense diversity afforded by asymmetric reactions. In general, the number of potential products produced from a matrix of reactants is $M \times 2^n$ where M=the number of reactants and n=the number of chiral centers. Consider a matrix comprised of bond forming reactions where one asymmetric bond is formed. The number of potential products increases as two times the product of the matrix. Note that for each bond formed the possibility exists to generate two chiral centers, so that for a single transformation the number of possible combinations is 4 or $2^2$. Consider a specific example of an asymmetric reaction, the Diels-Alder reaction, where two carbon-carbon bonds are formed and the potential for producing 4 chiral centers exists.

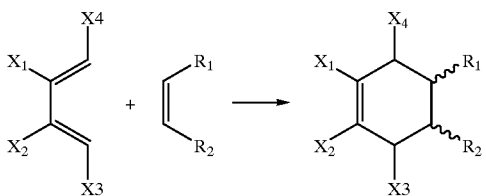

For the Diels-Alder reaction, the relative stereochemistry of the two ends of the dienophile reactant are coupled as are the two ends of the diene reactant, reducing the number of possibilities to $2^3$ for each diene/dienophile pair. This means that for a single dienophile in combination with 10 dienes, the number of possible product molecules that could be formed is $1 \times 10 \times 2^3 = 80$. To get the same level of diversity from traditional combinatorial approaches using only a single bond forming step would require the direct synthesis of 81 compounds. For an array of 10×10 reactants, the standard combinatorial approach yields 100 compounds. Expansion of the asymmetric Diels-Alder reaction array to 10×10 reactants has the potential to yield 800 new compounds from the original 20. Current combinatorial strategies cannot screen for all potential products of asymmetric transformations because it is generally not possible to obtain each of the products desired. As described above, the elimination of asymmetric reactions is a serious limitation of conventional combinatorial library approaches.

An ideal combinatorial library approach would be complementary to the SELEX™ method, where yield is not a concern, due to the ability to amplify the oligonucleotide products, and yet yield small organic molecules which are generally orally active and relatively inexpensive to produce. The present invention combines the power of SELEX™ with a novel approach for generating a large, structurally diverse library of products. The approach taken in the present invention overcomes many of the inadequacies associated with other combinatorial library approaches and represents a revolutionary concept in future drug discovery.

BRIEF SUMMARY OF THE INVENTION

The present invention provides product libraries which are evolved simultaneously with the corresponding nucleic acid facilitator required to produce each member of the library from one or more chemical reactants. More importantly, products can be identified from the product library which have predetermined desirable characteristics. This method, referred to herein as Parallel SELEX™, is a SELEX™-like process which is used to generate such a product library and subsequently to identify products with desired characteristics. As in the SELEX™ process, a huge, diverse nucleic acid test mixture is provided. Each nucleic acid is coupled to a chemical reactant. The invention is premised on the assumption that in a large enough nucleic acid library, one can identify nucleic acids in the nucleic acid test mixture capable of mediating a chemical reaction between the chemical reactant attached to the nucleic acid and a free chemical reactant. Further, among the subset of nucleic acids capable of mediating a chemical reaction, some are highly specific for generating each or a substantial portion of all the possible products. Therefore, the product library will contain at least some of all possible products for a given reaction. The nucleic acid provides facilitative specificity for the product and the product in turn provides specificity for a predetermined desirable action on a target.

The Parallel SELEX™ method alleviates many of the shortcomings of the prior art combinatorial library approaches. In its most basic form, the Parallel SELEX™ method comprises forming a product library by contacting two or more reactants wherein one of the reactants is coupled to a nucleic acid capable of mediating bond formation, selecting for products having predetermined desirable characteristics, and identifying the product using the power of the SELEX™ process for iterative amplification. A schematic depiction of the Parallel SELEX™ process is provided in FIG. 1.

The invention provides a method for identifying a desirable product from a product library, wherein said desirable product is selected for its ability to perform a preselected function on a target, said method comprising: preparing a nucleic acid-reactant test mixture comprised of nucleic acids each having a region of randomized sequence and each being associated with a first reactant; reacting said nucleic acid-reactant test mixture with a free reactant to form a product library comprised of nucleic acids associated with a product formed by the reaction of said first and free reactants; and partitioning between members of said product library based on their relative ability to perform said preselected function, whereby said desirable products can be identified.

The invention provides a product library comprised of a mixture of products that are the result of a reaction between at least a coupled reactant and a free reactant, wherein said coupled reactant is attached to the nucleic acid that facilitated the reaction between said reactants.

The Parallel SELEX™ method does not require keeping track of a matrix of products and their respective chemistries nor does it require highly efficient or rapid reactions. This advantage is a result of the fact that product formation is directed by specific nucleic acids. This directed approach is contrasted with the encoded approach taken by other combinatorial library approaches. The nucleic acid that specifically facilitates the desirable product formation can be easily amplified and the product reliably reproduced in subsequent rounds of production. This method allows a multitude of reactions to take place initially which can be sorted out later once it has been determined that products which display predetermined desirable characteristics have been formed. By this method, products may be selected for in the absence of detailed structural information.

The Parallel SELEX™ method can include the formation of product libraries using asymmetric reactions. Unlike conventional combinatorial library approaches, even though it is impossible to predict the stereochemical outcome at the onset of the reaction, asymmetric reactions can be included. The specific chemistry does not have to be tracked for the Parallel SELEX™ method to be effective. The only requirement is that the nucleic acid mediate at least a finite subset of the total number of possible reactions.

In another embodiment, facilitative nucleic acids are provided. Nucleic acids having facilitative properties are capable of mediating chemical reactions such as bond formation or bond cleavage. The nucleic acids can be modified in various ways to include other chemical groups that provide additional charge, polarizability, hydrogen bonds, electrostatic interaction, and fluxionality which assist in chemical reaction mediation. The other chemical groups can include, inter alia, alkyl groups, amino acid side chains, various cofactors, and organometallic moieties. The invention requires that the facilitative nucleic acids direct the synthesis of products which have predetermined desirable characteristics.

Included in the invention are pharmaceutical compositions containing the inventive products and methods of administering the compositions. Also included are diagnostic reagents, agricultural compositions and manufacturing compositions containing the inventive products.

BRIEF DESCRIPTION OF THE FIGURES

FIGS. 5A–C depict the impact of the mixed Aldol reaction described in FIG. 4 on structural diversity of the products. $A_{1-10}$ and $B_{1-10}$ depict the reactants. $C_{1-10}$, $D_{1-10}$, $G_{1-10}$ and $H_{1-10}$ depict diastereomers formed when A is the nucleophile and B is the electrophile. $E_{1-10}$, $F_{1-10}$, $I_{1-10}$ and $J_{1-10}$ depict diastereomers formed when B is the nucleophile and A is the electrophile. Only diastereomers are shown and each structure would have a corresponding enantiomer.

DETAILED DESCRIPTION OF THE INVENTION

The Parallel SELEX™ process provides product libraries which are formed by combining a pool of first chemical reactants coupled to a nucleic acid with a pool of free chemical reactants. The coupled nucleic acid is capable of mediating the chemical reaction which leads to the product library and further the nucleic acid is amplifiable so a product which has a predetermined desirable characteristic can be enriched for and identified from the product library.

Figure 1:
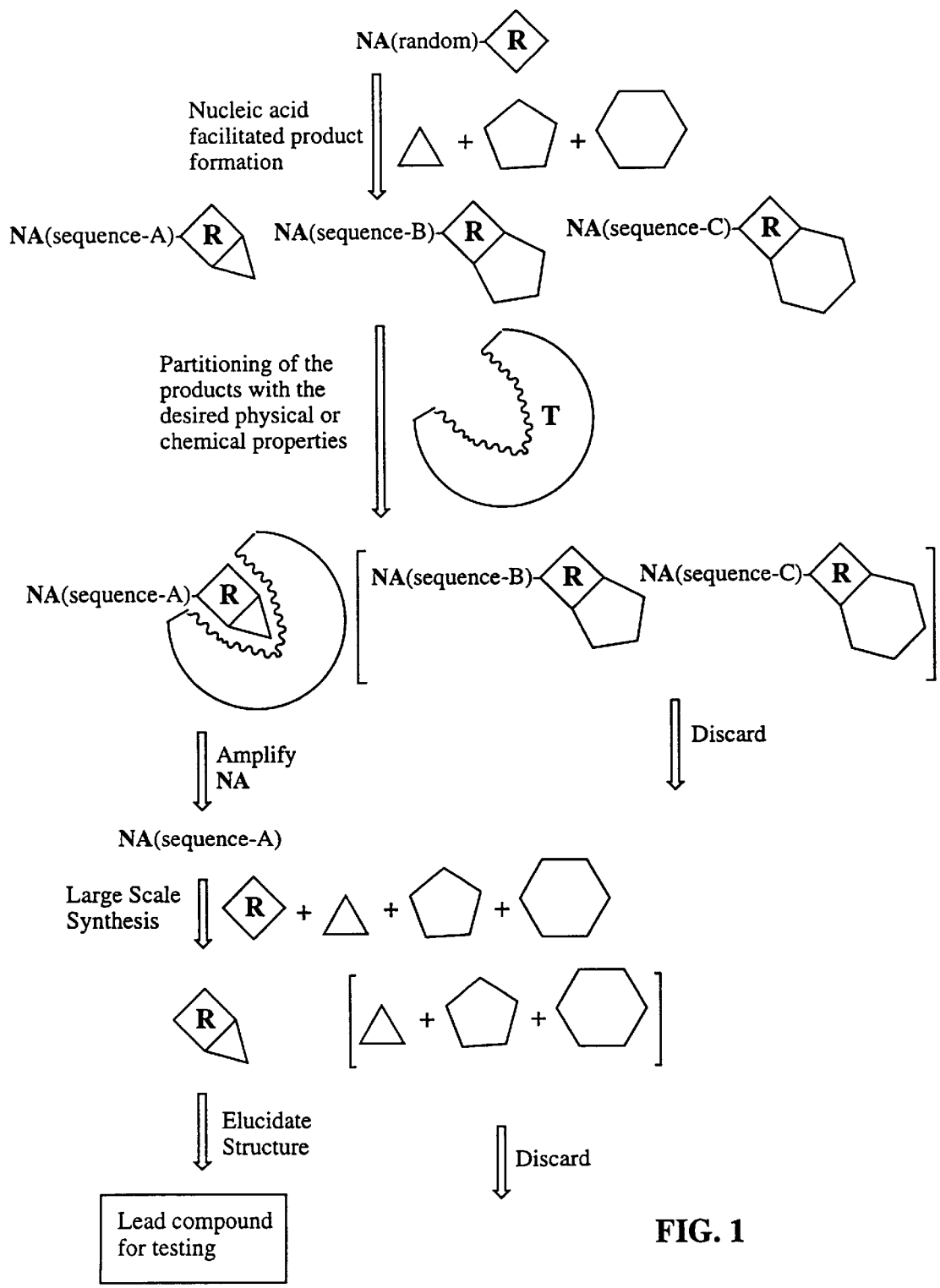
FIG. 1 depicts a schematic representation of the Parallel SELEX™ process in its most basic form.

In its most general form, the Parallel SELEX™ process may be described as in FIG. 1. A nucleic acid-reactant test mixture is formed by attaching a first reactant (R) to each of the nucleic acids in a test mixture (containing $10^2$ to $10^{18}$ nucleic acids with randomized sequences). The nucleic acid-reactant test mixture is treated with other free reactants (denoted as triangle, pentagon and hexagon) that will combine with the first reactant (R) to form different products. It is important to note that from the nucleic acid test mixture (NA), discrete nucleic acid sequences will be associated with facilitating the formation of the different shaped products as denoted by sequence-A, sequence-B and sequence-C in FIG. 1. The products may differ in shape, reactivity or both shape and reactivity. Partitioning of the desirable product shape or reactivity is accomplished by binding to or reaction with a target. Proteins, small molecules, lipids, saccharides, etc., are all examples of targets (T). After binding to or reacting with the target the non-interacting products, which are attached to sequence-B and sequence-C as depicted in FIG. 1 are separated from sequence-A and discarded. The nucleic acid sequence-A is then amplified by a variety of methods known to those experienced in the art. Sequence-A is then used to facilitate the assembly of the desirable product by facilitating the specific reaction to form the selected product on treatment with the mixture of starting reactants. In a typical reaction, Sequence-A can be reattached to the first reactant, however, said reattachment is not always required. This is an idealized case and in many examples the nucleic acid facilitator may assemble more than one product from the starting mixture, but all of the products selected will have the desired properties of binding to or chemical reaction with the target.

I. Definitions

Certain terms used to describe the invention herein are defined as follows:

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position base modifications, 5-position pyrimidine modifications, 8-position purine modifications, 7-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include those which enhance the facilitating properties of the nucleic acids. Modifications can also include 3' and 5' modifications such as capping. Modifications that occur after each round of amplification are also compatible with this invention. Post-amplification modifications can be reversibly or irreversibly added after each round of amplification. Virtually any modification of the nucleic acid is contemplated by this invention. The length of the randomized section of the nucleic acid is generally between 8 and 800 nucleotides, preferably between 40 and 400 nucleotides.

"Nucleic acid test mixture" is a mixture of nucleic acids of differing, randomized sequence including some which have a shape which enables them to mediate the formation and/or cleavage of chemical bonds. The source of a "nucleic acid test mixture" can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic acid having facilitating properties" or "facilitating nucleic acid" or "facilitative nucleic acid" or "nucleic acid facilitator" refers to any nucleic acid which is capable of mediating or facilitating a chemical reaction. The chemical reaction can be a bond formation or bond cleavage reaction. The preferred embodiments of this invention are directed to bond formation reactions. The nucleic acid does not necessarily need to show catalytic turnover to be considered to have facilitating properties. The reaction rate of product formation can be increased by the presence of the nucleic acid, however, increased reaction rate is not a requirement for facilitating properties. A facilitating nucleic acid folds such that its three-dimensional structure facilitates a specific chemical reaction. The nucleic acid can mediate the chemical reaction either alone, in combination with another catalytic moiety coupled directly with the nucleic acid, or in combination with another catalytic moiety which could be found in solution. The other catalytic moieties can include organometallic moieties, metal ions, etc. The nucleic acid can cause different stereoisomers to be formed. The nucleic acid can mediate formation or cleavage of a variety of bond types, including, but not limited to, condensation/ hydrolysis reactions, cycloaddition reactions (such as the Diels-Alder reaction, the Ene reaction, and the 1,3 dipolar reaction), conjugate addition to α,β-unsaturated compounds, Aldol condensations, Claisen reaction, glycosylation of peptides, sugars and lipids. Additionally, when the nucleic acid modification includes an organometallic moiety, other reactions may occur which could form symmetric or asymmetric products, including, but not limited to, cyclopropanation, epoxidation, azridination, hydrogenation, cyclotrimerization of alkynes, [3+2] and [4+1] cycloaddition of unsaturated molecules, and olefin metathesis.

"Reactant" refers to any chemical entity that could be involved in a bond forming or bond cleavage reaction which is compatible with the thermal and chemical stability of nucleic acids, including the modifications described above. The term reactant may refer to a single chemical entity or a class of chemical compounds, including several reactants of several general chemical structures or several reactants of different general chemical structures. A reactant typically has a molecular weight in the range of 2 to 1000, preferably about 26 to 500. Particularly preferred reactants include small organic molecules such as alkenes, alkynes, alcohols, aldehydes, ketones, esters, carboxylic acids, aromatic carbocycles, heterocycles, dienes, thiols, sulfides, disulfides, epoxides, ethers, amines, imines, phosphates, amides, thioethers, sulfonates and halogenated compounds. Inorganic reactants are also contemplated by this invention. However, in some embodiments of the invention, larger reactants can be included, such as polymers or proteins. The selection of the chemical reactants used can be random or based on a number of criteria, including the nature of the product desired, the activity the product is meant to have, or information based on the nature of the target on which the product is meant to act.

"Coupled Reactant" or "First Reactant" or "First Chemical Reactant" refers to those Reactants described above which are coupled to a nucleic acid to form a nucleic acid-reactant test mixture. The coupling of the first reactant to the nucleic acid can be either covalent or non-covalent. The first chemical reactant can be a single chemical entity or a class of chemical molecules, including several reactants of several general chemical structures or several reactants of different general chemical structures. For example, the first reactant may be one alkene (e.g., 1-propene), or 10 different alkenes, or 10 different alkenes and 10 different alkynes.

"Free Reactant" or "Second Reactant" or "Free Chemical Reactant" refers to those reactants that are not coupled to a nucleic acid. A reaction may involve more than one free reactant, as in a cyclotrimerization reaction. The free reactants may be the same or different from each other or from the coupled reactant. For example, the free reactant may be one alkene (e.g., 1-propene), or 10 different alkenes, or 10 different alkenes and 10 different alkynes.

"Nucleic acid-reactant test mixture" refers to the mixture of nucleic acids each of which has been coupled to a first chemical reactant. The coupling can be covalent or non-covalent, direct or with a linker between the nucleic acid and the reactant. The nucleic acid-reactant test mixture is contacted with a pool of free chemical reactants to enable the formation of a product library.

"Product" refers to a compound resulting from a bond forming or bond cleavage reaction between one or more reactants which has been mediated by a nucleic acid. In the preferred embodiment, a product is typically formed between a coupled reactant and a free reactant. Two reactants that react to make a product do not necessarily have to be reactants of different chemical structures. Preferably the products of this invention are small organic molecules that can be medicinally active and show therapeutic efficacy or are useful as diagnostic agents or agricultural agents. The typical molecular weight of a product is in the range of about 40 to 2000, preferably about 100 to 1000. However, in certain less preferred embodiments, the products can be larger molecules as illustrated by peptides, proteins, polymers, etc. In certain less preferred embodiments, the reaction is a bond cleavage reaction and can take place with only the coupled reactant or between two or more reactants.

"Product library" refers to the collection of products formed by the chemical reaction between a reactant coupled to a facilitating nucleic acid and preferably at least one free reactant. Due to the nature of the invention, a product library can contain many diverse products of varying chemical structures.

"Product having the ability to perform a preselected function on a target" or "Product having Predetermined Characteristic" or "Desirable Product" refers to a product that acts on a target in a predetermined desirable manner. Examples of predetermined desirable actions on a target include, but are not limited to, binding of the target, catalytically changing the target, reacting with the target in a way which modifies/alters the target or the functional activity of the target, covalently attaching to the target as in a suicide inhibitor, facilitating the reaction between the target and another molecule. As one example, in a product library, a product having a predetermined characteristic is one which binds a target with greater affinity than that of the bulk population. In any given product library there can exist more than one product having a predetermined characteristic for a given target. The products having predetermined characteristics can differ from one another in their binding affinities for the target or in their other abilities to act on the target.

"Target" refers to any compound upon which a product identified by the Parallel SELEX™ method can act in a predetermined desirable manner. A target molecule can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc., without limitation.

Particularly preferred targets include, but are not limited to, angiotensin converting enzyme, renin, cyclooxygenase, 5-lipoxygenase, IL-1β converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA$_2$, red blood cells, glioblastomas, fibrin clots, PBMCs, hCG, lectins, selecting, cytokines, ICP4, complement proteins, etc.

"Partitioning" means any process whereby members of the nucleic acid test mixture or nucleic acid-reactant test mixture can be separated from the bulk of the test mixture based on the ability of the nucleic acid to facilitate a reaction involving its associated reactant, resulting in a desirable product. Partitioning can be accomplished by various methods known in the art. Filter binding, affinity chromatography, liquid-liquid partitioning, filtration, gel shift, density gradient centrifugation, molecular weight filter partitioning, size exclusion chromatography, size exclusion membrane separation and isoelectric focusing are all examples of suitable partitioning methods. The choice of partitioning method will depend on properties of the target and the product and can be made according to principles and properties known to those of ordinary skill in the art.

Additionally, it may be desirable as an initial partitioning step to partition between nucleic acids which are associated with products (and therefore facilitating nucleic acids) vs. those which are only associated with a first reactant (non-facilitating nucleic acids). This partitioning step can be accomplished by numerous methods known to one of ordinary skill in the art, such as sizing columns, affinity chromatography, etc. After such a partitioning step, the nucleic acid test mixture would be enriched for facilitating nucleic acids.

"Amplifying" means any process or combination of process steps that increases the amount or number of copies of a molecule or class of molecules. In preferred embodiments, amplification occurs after members of the test mixture have been partitioned, and it is the facilitating nucleic acid associated with a desirable product that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplification can be made after each round of amplification, if necessary.

"Randomized" is a term used to describe a segment of a nucleic acid having, in principle, any possible sequence over a given length. Randomized sequences will be of various lengths, as desired, ranging from about eight to more than one hundred nucleotides. The chemical or enzymatic reactions by which random sequence segments are made may not yield mathematically random sequences due to unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into a randomized sequence, for example, by altering the molar ratios of precursor nucleoside (or deoxynucleoside) triphosphates in the synthesis reaction. A deliberate bias may be desired, for example, to affect secondary structure, to introduce bias toward molecules known to have facilitating activity, to introduce certain structural characteristics, or based on preliminary results.

"SELEX™" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX™ methodology is employed to amplify the nucleic acid associated with a desirable product.

"Parallel SELEX™" is a method wherein nucleic acids in a nucleic acid test mixture are coupled to a chemical reactant which is then contacted with a pool of other free chemical reactants under conditions favorable for facilitated bond formation to produce a product library. The product library is screened to identify products having predetermined desirable characteristics. The product can be tested for its ability to act on a given target in the predetermined manner (e.g., bind to the target, modify the target in some way, etc.). The desirable products can then be partitioned away from the undesirable products. The desirable product remains coupled to the facilitating nucleic acid that directed its synthesis. The facilitating nucleic acid can be partitioned away from the remainder of the pool and amplified as described in the SELEX™ method. The facilitating nucleic acid can be partitioned alone or along with its associated desirable product. The amplified nucleic acids are enriched for the nucleic acids which are capable of assembling desirable products. The amplified nucleic acids are then recoupled to the first reactant, recontacted with the free reactants, and the iterative cycling of the selection/amplification steps of the SELEX™ process are incorporated to synthesize, select and identify desirable products. The selected nucleic acids ultimately produce enough of the desirable product so that the structure can be determined II. The Reaction A. The Nucleic Acid The Parallel SELEX™ process depends on the ability of a nucleic acid to mediate product formation. The method requires the initial preparation of a nucleic acid test mixture. In general, the rationale and methods for preparing the nucleic acid test mixture are as outlined in the SELEX™ Patent Applications described earlier which are herein incorporated by reference. Briefly, a nucleic acid test mixture of differing sequences is prepared. Each nucleic acid in the test mixture generally includes regions of fixed sequences (i.e., each of the members of the test mixture contains the same sequences in the same location) and regions of randomized sequences. The fixed sequence regions are selected either: (a) to assist in the amplification steps described in detail in the SELEX™ patents, (b) to mimic a sequence known to mediate a reaction, (c) to enhance the concentration of nucleic acids of a given structural arrangement in the test mixture or (d) to facilitate the ligation of the first reactant. The randomized sequences can be totally randomized (i.e., the probability of finding a base at any position being one in four) or only partially randomized (e.g., the probability of finding a base at any location can be selected at any level between 0 and 100 percent). The nucleic acids found in the nucleic acid test mixture will include those capable of proper folding in order to specifically mediate various chemical reactions.

The nucleic acid test mixture can be modified in various ways to enhance the probability of the nucleic acids having facilitating properties. The modifications contemplated by this invention are any modifications which introduce other chemical groups that have the correct charge, polarizability, hydrogen bonding, electrostatic interaction, or fluxionality and overall can adopt the shape needed to perform the reaction. Without wishing to be bound by any theory, it is believed that the mechanism for performing the reaction can include, but is not limited to, stabilizing the reaction transition state, facilitating specific chemical reactions and binding to the free reactant in a manner that brings it in close proximity to the coupled reactant, without limitation. The modifications that may enhance the active site of the nucleic acid include hydrophilic moieties, hydrophobic moieties, metal atoms in various oxidation states, rigid structures, functional groups found in protein enzyme active sites such as imidazoles, primary alcohols, carboxylates, guanidinium groups, amino groups, thiols and the like. Additionally, organometallic and inorganic metal catalysts can be incorporated as the other chemical group of the nucleic acid, as can redox reactants.

The individual components of a nucleic acid test mixture can be modified in various ways. Suitable modifications include, but are not limited to, modifications on every residue of the nucleic acid, on random residues, on all pyrimidines or purines, or all specific bases (i.e., G, C, A, T or U), or one modification per nucleic acid. It is also recognized that certain molecules (e.g., metal catalysts and the like) can be in solution, not attached to the nucleic acid, and be useful in mediating the reaction in concert with the mediating action of the nucleic acid. It is believed that as long as the nucleic acid coupled to the first chemical reactant is in some way associated with mediating the chemical reaction that the method and products fall within the scope of this invention. It is also recognized that modification is not a prerequisite for facilitating activity of the nucleic acids of the invention.

Under some circumstances it may be desirable to preselect for nucleic acids that bind to a target. In this embodiment, the random nucleic acid pool is subjected to several rounds (1–10) of SELEX™ against the target molecule before the reactant is coupled to the nucleic acid pool.

i. Modifying Nucleotides with Other Chemical Groups

The nucleotides can be modified in any number of ways, including modifications of the ribose and/or phosphate and/or base positions. Certain modifications are described in U.S. patent application Ser. No. 08/117,991 entitled "High Affinity Nucleic Acid Ligands Containing Modified Nucleotides", now abandoned (see also U.S. Pat. No. 5,660,985) and U.S. patent application Ser. No. 08/076,735 entitled "Method for Palladium Catalyzed Carbon-Carbon Coupling and Products," now U.S. Pat. No. 5,428,149, which are herein incorporated by reference. In one embodiment, modifications are those wherein another chemical group is attached to the 5-position of a pyrimidine, the 7- or 8-position of a purine, or the 2' position of a sugar. There is no limitation on the type of other chemical group that can be incorporated on the individual nucleotides. In the preferred embodiments, the resulting modified nucleotide is amplifiable or can be modified subsequent to the amplification steps.

As an example, which is not meant to limit the invention in any way, one can envision a biomimetic facilitating nucleic acid. One choice for modification of the nucleic acids includes modifications which would make certain bases appear more like proteins in their chemical and physical properties. Certain modifications of pyrimidine and purine nucleotide bases can be made to make the nucleic acid appear to have "side chains" similar to the amino acid side chains of proteins. Several synthetic methods are available to attach other chemical groups, in this case amino acid derivatives, to the 5-position of a pyrimidine or the 7- or 8-position of a purine. Methods for modifying pyrimidines at the 5-position have been described in U.S. patent application Ser. No. 08/076,735, now U.S. Pat. No. 5,428,14, Ser. No. 08/347,600, now U.S. Pat. No. 5,580,972, and Ser. No. 08/458,421, (now U.S. Pat. No. 5,719,273), as well as other published procedures. Numerous published procedures are known for modifying nucleic acids including, but not limited to the following Limbach, Pa., et al.,1994. *Nucleic Acids Res.* 22:2183–2196 and references cited therein; Hayakawa H, et al., 1985. *Tetrahedron* 41: 1675–83; Crouch G J et al., 1994. *Nucleosides Nucleotides* 13: 939–44; Scheit K H, 1966. *Chem. Ber.* 98: 3884; Bergstrom and Ruth., 1976. *J. Am. Chem. Soc.* 98: 1587–89; Bergstrom and Ogawa, 1978. *J. Am. Chem. Soc.* 100: 8106–12; Ruth and Bergstrom, 1978. *J. Org. Chem.* 43: 2870; Bergstrom D E et al., 1981. *J. Org. Chem.* 46: 1432–41; Bergstrom D E. 1982. *Nucleosides Nucleotides* 1:1–34; Crisp and Flynn, 1990. *Tetrahedron Lett.* 31: 1347–50; Hobbs F W Jr. 1989. *J. Org. Chem.* 54: 3420–22; Hirota K et al., 1993. *Synthesis* 213–5; Nagamachi T et al., 1974. *J. Med. Chem.* 17: 403–6; Barton DHR et al., 1979. *Tetrahedron Lett.* 3:279–80; Hirota K et al., 1992. *J. Org. Chem.* 57: 5268; Mamos P et al., 1992. *Tetrahedron Lett.* 33: 2413–16; Sessler J L et al., 1993. *J. Am. Chem. Soc.* 115: 10418–19; Long R A et al., 1967. *J. Org. Chem.* 32: 2751–56; Prakash T P et al., 1993. *Tetrahedron* 49: 4035; Janokowski A J et al., 1989. *Nucleosides and Nucleotides* 8: 339; Kumar and Buncel, 1984. *J. Inorg. Biochem.* 22: 11–20; Moffatt J G. 1979. in *Nucleoside Analogues*, eds. R T Walker, E De Clercq, F Eckstein pp. 71–163 New York: Plenum Press; Townsend L B. 1988. *Chemistry of Nucleosides and Nucleotides* pp.59–67 New York: Plenum Press; Verheyden J P H et al., 1971. *J. Org. Chem.* 36:250–54; Wagner D, et al., 1972. *J. Org. Chem.* 37:1876–78; Sproat Lamond, 1991. In *Oligonucleotides and Analogues A Practical Approach*, ed. F. Eckstein pp.49–86. New York: Oxford University Press; Lesnik E A et al., 1993. *Biochemistry* 32:7832–38; Sproat B S et al., 1991. *Nucleic Acids Res.* 19:733–38; Matsuda A et al., 1991. *J. Med. Chem.* 34:234–39; Schmit C. 1994. *Synlett* 238–40; Imazawa and Eckstein, 1979. *J. Org. Chem.* 44:2039–4; Schmit C. 1994. *Synlett* 241–42; McCombie and Metz., 1987. *Tetrahedron Lett.* 28:383–6; Imazawa M, et al., 1975. *Chem. Pharm. Bull.* 23:604–10; Divakar K J et al,, 1990. *J. Chem. Soc., Perkin Trans.* 1 969–74; Marriott J H et al., 1991 *Carbohydrate Res.* 216:257–69; Divakar and Reese, 1982. *J. Chem. Soc., Perkin Trans.* 1 1625–28; Marriott J H et al., 1990. *Tetrahedron Lett.* 31:7485–88.

The above-described amino acid-modified nucleotides can be substituted for the native nucleotides and incorporated into the sequences of the nucleic acid test mixture. Nucleotides modified with other chemical groups in place of the above-described amino acids are also contemplated by this invention. Oftentimes, a working assumption can be made about which modified nucleotides would be most desirable for addition to the nucleic acid test mixture. For example, if the reaction which is intended to be mediated is an aldol condensation, guided by the structure of Class I Aldolases, the needed other chemical group could be an amino acid derivative that contains a primary amino group to form an imine with the carbonyl substrate and another basic group to facilitate formation of the enamine that serves as the nucleophile in the reaction.

Other nucleotide modifications include attaching functional groups to nucleotides which enhance the facilitating properties of the nucleic acids. Such functional groups may participate in creating active sites of a facilitating nucleic acid. The active sites created may be capable of binding multiple substrates and aligning key facilitating functions with high precision. These functional groups should have sufficient conformational freedom to coordinate the reaction dynamics of reactants and the active site to aid in bond formation. Functional groups include both polar and non-polar groups, groups which can generally act as acids, bases, nucleophiles, electrophiles and metal ligands. By modifying nucleotides in this manner, all possible types of facilitating nucleic acids may be produced having appropriate properties including, but not limited to, solvation, pKa, polarizability, dynamics, etc. which allow the nucleic acids to facilitate interactions between virtually any type of reactants. Nucleotides may be substituted at sugar and/or base and/or phosphate positions with one or more of such functional groups which include, but are not limited to,

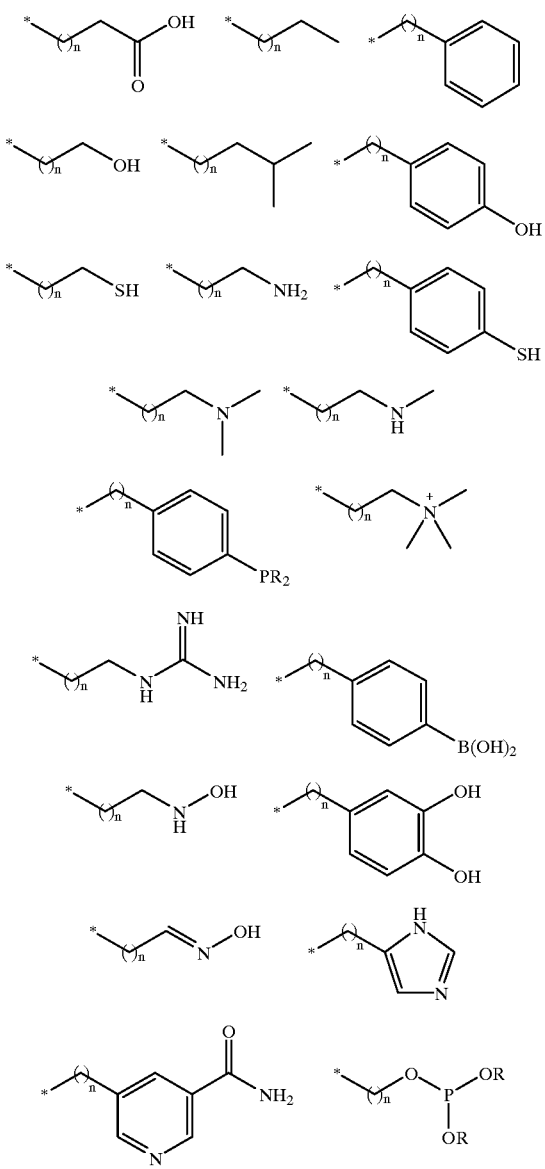

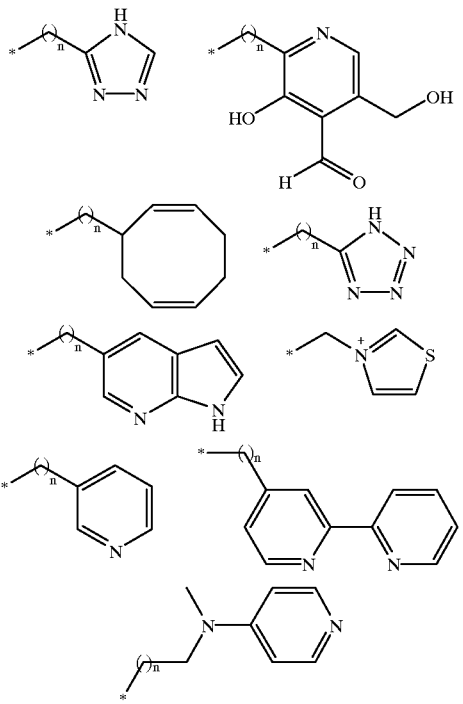

wherein the asterisk indicates the point of attachment of the functional group to the nucleic acid, n may be any integer, preferably n is 0–20, and wherein such chemical groups may also include substitutions at the aliphatic or aromatic positions. Preferably the functional groups are base substituents.

ii. Modifying the Nucleic Acid with Organometallic Groups

Another modification to the nucleic acid test mixture contemplated by this invention is incorporating an organometallic reagent into the sequences that make up the nucleic acid test mixture. Use of organometallic catalysts in the synthesis of complicated organic structures has revolutionized organic syntheses. An organometallic catalyst is any metal and organic ligand sphere capable of mediating a reaction. The ligands that can make up the coordination sphere are known to those skilled in the art, and include pyridine ligands, phosphine ligands, oxime ligands, porphyrins, isocyanates, cyanates, carboxylates, thiols, carbon monoxide, alkenes, ethers and the like. Useful metals include nickel, rhodium, cobalt, palladium, zirconium, aluminum, iron, manganese, titanium, ruthenium, molybdenum and boron. For example, pyridinium nickel complexes are known to catalyze urea hydrolysis; rhodium acetate catalysts facilitate cyclopropanation; cobalt complexes catalyze cyclotrimerization and [3+2] cycloaddition; palladium catalyzes hydrogenation and [3+2] cycloaddition; ruthenium and molybdenum complexes catalyze olefin metathesis. Taken together these reactions can prepare 3, 4, 5, 6 and 7 membered rings, all of which are known to be useful in the structure of many medicinal compounds. Larger rings may be prepared by π-allyl palladium catalysis. Formation of chiral centers is crucial to the synthesis of many biologically active compounds and in many cases the wrong enantiomer can have deleterious pharmacological effects. An asymmetric hydrogenation to form single enantiomers has been accomplished by palladium and zirconium complexes.

In this embodiment, several options are available to connect the organometallic complex to the oligonucleotide.

The organometallic complex can be attached directly to the nucleotide base, such as at the 5-position of a pyrimidine. The modified oligonucleotide should amplify with good integrity.

In some cases, the linkage between the nucleic acid and the organometallic complex should be cleavable, leaving the oligonucleotide intact. Examples of cleavable linkages include, but are not limited to, photochemically labile linkers, disulfides and carbonates. These linkage chemistries are well known to those of ordinary skill in the art and could be used to attach the organometallic complex to the 5' or 3' end of a nucleic acid or the 5-position of pyrimidine residues in the nucleic acid.

Another option would be to use a cassette oligonucleotide that may be synthesized to include an organometallic complex. The cassette oligonucleotide embodiment would include a fixed nucleic acid sequence having an organometallic complex associated with it which could be ligated onto the nucleic acid at the start of each round of selection. Each member of the nucleic acid test mixture would have an identical fixed region complementary to the fixed sequences of the cassette. This cassette oligonucleotide may obviate the need for other conjugation methods.

It may also be desirable to embed the organometallic catalyst within an oligonucleotide. For some of these embodiments, the modification can take place after each round of amplification. In the case of embedding the organometallic complex within the oligonucleotide, more than one cleavable bond may be desirable and the chemistry of each cleavable bond will need to be unique. The bipyridine ligand is used as an example in the scheme shown below.

would be readily synthesized by chemical methods. For some organometallic complexes it will be required that the metal be incorporated subsequent to synthesis or transcription. In these cases the chelating ligands that bind the metal would be attached to the oligonucleotide as discussed above and the metal introduced after nucleic acid synthesis or amplification by ligand exchange reactions.

Embedding an organometallic catalyst in the nucleic acid may be accomplished by adding a functional group to the catalyst that causes the organometallic complex to associate with the nucleic acid. Typically, ligands such as acetylacetate, amines, carboxylates, pyrazole borates, porphyrins, carboranes, thiols, sulfides, phosphines, phosphites, binapthols, salens, oxazolines and oxime metal coordinating ligands can be modified with functional groups that will result in an enhanced affinity of these ligands, and any bound metal, for the nucleic acid. The metal coordinating ligands can be modified to include nucleic acid binding groups such as, but not limited to, amine, amide, sulfoxide, sulfonate, hydroxyl, guanidinium, polyamine, putrescene, or spermidine. Non covalent attachment of the organometallic catalyst to the nucleic acid may be accomplished by electrostatic attraction, in which case the functional groups on the catalyst would contain a net positive charge. In addition, association of the nucleic acid to the organometallic catalyst complex could be accomplished by introducing groups that intercalate within the nucleic acid structures and are not bound by electrostatic attraction. Furthermore, groups that bind with good affinity to the major and minor groves of nucleic acids are well known and could also be attached to

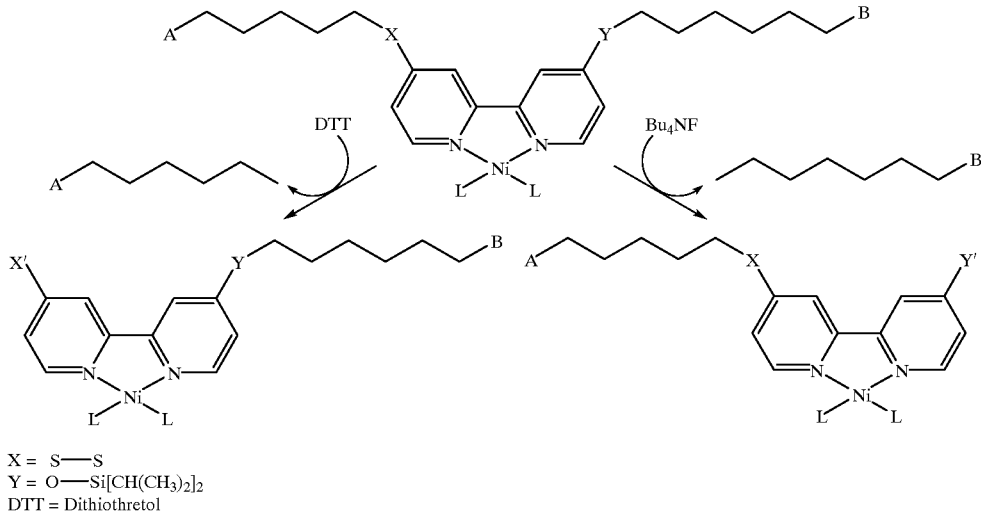

X = S—S
Y = O—Si[CH(CH$_3$)$_2$]$_2$
DTT = Dithiothretol

Because the oligonucleotide components labeled A and B may be chemoselectively cleaved from the support their sequences may be determined independently. In addition, A and B may be comprised of relatively short sequences that the ligands of the organometallic complex. An example of an organometallic cofactor that can serve as a catalyst for the cyclotrimerization of alkynes, and alkenes is provided in the Scheme below.

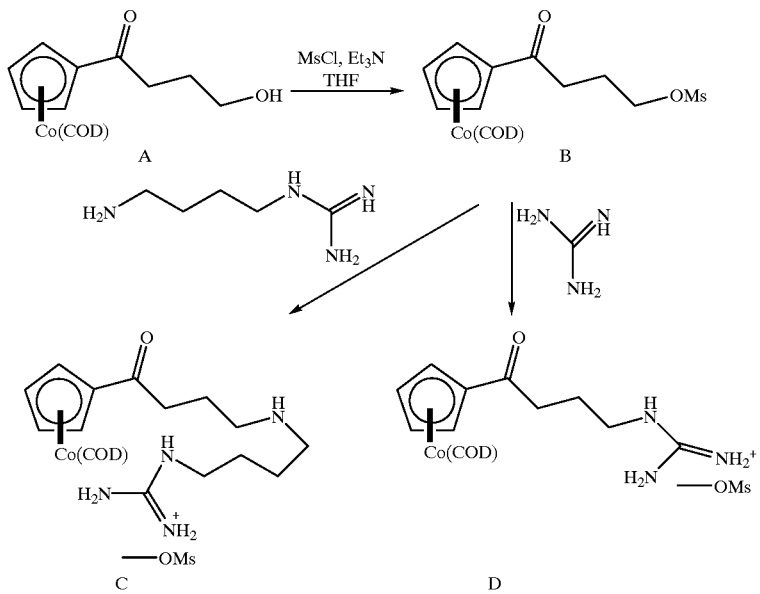

The cobalt complex A, which is the subject of U.S. patent application Ser. No. 08/619,228, filed Mar. 20, 1996, now U.S. Pat. No. 5,659,069, entitled "Method for the Cyclotrimerization of Alkynes in Aqueous Solutions", the subject matter of which is incorporated herein by reference, is in one possible example, rendered a nucleic acid cofactor by activating the hydroxyl for substitution as in B. Substitution of B with either agmatine to give C, or with guanidine to give D gives a cobalt complex that now possesses the type of groups capable of electrostatic binding to nucleic acids. The attraction of a positive guanidyl group for a phosphate is well known, supplying approximately 3 kcal/mol of binding energy. Additional hydrophobic contacts or intercalation of the cyclopentadienyl or cyclooctadienyl ligands with the nucleic acids will enhance both the affinity and specificity of the binding of the cobalt organometallic cofactor.

As can be seen from the examples provided above, there are numerous ways to modify the nucleic acid to enable it to mediate chemical reactions, such as bond formation and bond cleavage. All modifications of the nucleic acid are contemplated by this invention.

B. The Reactants

In its broadest sense, the term reactants refers to any chemical entity that is compatible with the thermal and chemical stability of nucleic acids which can be involved in a bond forming or bond cleaving reaction. This invention should not be limited by the type of reactant. The following classes of small organic molecules are intended to be non-limiting examples of potential reactants: alkenes, alkynes, alcohols, aldehydes, ketones, esters, carboxylic acids, aromatic carbocycles, heterocycles, dienes, thiols, sulfides, disulfides, epoxides, ethers and halogenated compounds. The reactants preferably have a molecular weight in the range of 2 to 1000, most preferably in the range of 26 to 500. Where the desired products are larger molecules, the reactants would also be larger, such as with peptides, proteins and polymers. The reactants can contain more than one of the listed functionalities and can contain chiral centers. In general, the term reactants represents a class of chemical reactants defined by its chemically reactive unit (e.g., diene, ester, etc.). As an example, the chemical reactant can be a class of reactants which could include 1 to $10^n$ different members of the class. The reactants chosen for any given reaction may also include several classes of reactants.

At some level in the process of determining suitable reactants for the Parallel SELEX™ process, a target must be identified and the mode of action by which a desirable product would act on such target must be determined. Once that determination is made, a class of products thought likely to have the desirable properties can be selected. Suitable reactants that are likely to produce the desired class of products can then be selected and incorporated into the Parallel SELEX™ process.

The selection of reactants can be determined randomly. However, preferably the choice of reactants can be based upon a number of criteria including, but not limited to, selecting reactants based on the desired class of products, which can be determined by initial structural assumptions based on similarity to known compounds having a desired characteristic, other known ligands, computer modeling simulations, NMR and X-ray data/structure, enzymatic and chemical footprinting experiments. Once a product class is identified, the reactants are selected to maximize the variability that can be obtained. Often, retrosynthesis procedures are employed to select possible reactants. Multiple classes of reactants can be used simultaneously.

For the purposes of this invention, the reactant which is coupled to the nucleic acid will be termed the first reactant or coupled reactant. Typically, the first reactant will be contacted with at least one free reactant under conditions favorable for facilitated bond formation, and the resulting product will be assayed to determine if it has a predetermined desirable characteristic. It is envisioned that a first reactant can chemically react with more than one other reactant (i.e., second, third, forth, etc. reactants) to form a product. It is also envisioned that more than one type of chemical reaction can be taking place simultaneously. It is also contemplated that multiple reactions may be taking place simultaneously or stepwise, possibly using multiple nucleic acids to facilitate different portions of the product formation. Ideally, reactants are selected so that, depending on the ability of the facilitating nucleic acid sequences to specifically generate products, a product library is created.

C. Coupling the Reactant to the Nucleic Acid

The Parallel SELEX™ process requires that the first reactant be coupled to the nucleic acid having facilitating properties which is present in the nucleic acid test mixture. The first reactant is coupled to the nucleic acid either covalently or non-covalently. The coupling can theoretically be anywhere on the nucleic acid. However, for practical purposes, the coupling usually takes place on the 5' or 3' ends of the nucleic acid. Typically, the coupling is through a ligation reaction, but any known coupling reaction is acceptable. The coupling can be direct, as could be done with a 5' GMPS, a 3' dideoxy with terminal transferase, or the like.

The coupling between the nucleic acid and reactant may also include a linker group. Such a linker group may allow the nucleic acid to fold in a more favorable conformation so that it can better interact with the reactants to mediate the reaction. The linker group may allow the first reactant to explore the entire surface and catalytic pockets of the folded nucleic acid.

The linker group can be any suitable spacer moiety. The linker group should be of sufficient length, preferably made up of polymeric units, to allow for a flexible tether that would enable the various reactants access to the entire surface and binding pockets of the folded nucleic acid. The optimal size of the linker is dependent on the size of the nucleic acid. In general, the size of the linker group should be between 10 and 1000 Å, preferably between 50 and 300 Å. The linker group can be varied in the nucleic acid-reactant test mixture to select optimum length for a desired reaction. The linker group should also be easily solvated under the reaction conditions. Suitable linker groups are exemplified by PEG, poly vinyl alcohol, polyacrylates and polypeptides.

The linkage between the linker group and the nucleic acid preferably is cleavable, leaving the nucleic acid intact. Examples of suitable cleavable linkages include, but are not limited to, photochemically labile linkers, disulfides, cis-diols and carbonates. The linkage can also be cleavable with enzymes, such as DNAse and proteinases.

Additionally, the linkage can be by the Splint Blended SELEX™ method described in U.S. patent application Ser. No. 08/234,997, filed Apr. 28, 1994 entitled Systematic Evolution of Ligands by Exponential Enrichment:Blended SELEX™, now U.S. Pat. No. 5,683,867, which is herein incorporated by reference.

D. Product Formation

A chemical reaction occurs when a first reactant and at least a second reactant interact and form a product or when a first reactant is cleaved in some way that is facilitated by its associated nucleic acid. Any number of chemical reactions are compatible with the Parallel SELEX™ method. The only requirement is that the reaction be mediated by the nucleic acid coupled to the first reactant. Preferably, the mediation by the nucleic acid is specific for the reactants and desired product, however, that may not always be the case. The chemical reactions include both bond formation and bond cleavage reactions. Various bond formation reactions are contemplated by this invention and by way of example include condensation/hydrolysis reactions, cycloaddition reactions such as the Diels-Alder and Ene reaction, conjugate addition to α,β-unsaturated compounds, Aldol condensations, glycosylation of small organic molecules, peptides, sugars and lipids. Additionally, when the nucleic acids in the test mixture are modified to include an organometallic catalyst into the nucleic acid, other reactions, including, but not limited to, cyclopropanation, hydrogenation, cyclotrimerization of alkynes and alkenes, [3+2] and [4+1] cycloaddition of unsaturated molecules, and olefin metathesis may occur, all of which could form asymmetric molecules. This invention contemplates use of these reactions alone or together in any combination. This invention further contemplates successive reactions wherein a first product can be made with two or more reactants and then that product can become a "reactant" with other free reactants to form a second product, etc.

Bond cleavage reactions are also included in this invention. Bond cleavage reaction has several embodiments, including, but not limited to, cleavage of the first reactant to form a product that interacts with a target, cleavage of the first reactant so that it is now able to better react with a second reactant to form a new product, etc.

The invention also includes embodiments wherein the products formed by the method of the invention are attached to other molecules, including but not limited to, labels, antibodies, other small molecules, etc.

The reaction(s) can take place under a variety of conditions known to one of ordinary skill in the art, which are consistent with the stability requirements of nucleic acids. The reaction can take place in any buffered or non-buffered aqueous solvent, such as water, Tris, HEPES, etc. or in an organic solvent system with appropriate alkyl ammonium or similar counter ions, such as alcohol/water, DMSO, dioxane/water, acetonitrile/water, DMF/water, with triethylammonium salt. Alternatively, aqueous-organic biphasic solvent systems may be appropriate for some applications. The temperature range is generally −10° C. to 100° C., preferably 10° C. to 50° C. The concentration of the randomized nucleic acid-reactant test mixture is generally in the range of 1 pM to 10 mM, preferably 1 to 100 $\mu$M, and the concentration of the second reactant is generally in the range of 1 $\mu$M to 10 M, preferably 10 $\mu$M to 10 mM.

E. Partitioning Products having Predetermined Desirable Characteristics

Once a chemical reaction has taken place, one must screen the product library for products having predetermined desirable characteristics. As described earlier, predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IL-1β converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA$_2$, red blood cells, glioblastomas, fibrin clots, PBMCs, hCG, lectins, selectins, cytokines, ICP4, complement proteins, etc.

The conditions under which the products are screened are not limited to the conditions for product formation described in section D above. Screening conditions are known to one of ordinary skill in the art.

Products having predetermined desirable characteristics can be partitioned away from the rest of the product library while still attached to the nucleic acid which facilitated their formation by various methods known to one of ordinary skill in the art. The key is to partition the desirable products away from the entire product library without chemical degradation of the attached nucleic acid such that the nucleic acids are amplifiable. The nucleic acid can then be amplified, either still attached to the desirable product or after separation from the desirable product, as taught in the basic SELEX™ method.

In the most preferred embodiment, the desirable product acts on the target without any interaction between the nucleic acid attached to the desirable product and the target. The nucleic acid facilitates the reaction between its attached reactant and a free reactant yielding the desirable product, and also is amplifiable so that the desirable product can be subsequently reproduced and ultimately identified from the vast product library. However, it is not envisioned in this preferred embodiment that the nucleic acid interacts directly with the target.

The nucleic acid can be modified prior to contact with the target to ensure that it does not interact with the target. The modification can take place several ways, including making the nucleic acid double stranded so that it is less capable of interacting with the target. Another modification includes pH reversible glyoxal denaturation. In a somewhat less preferred embodiment, the nucleic acid can act on the target, either independently or in concert with the desirable product whose synthesis it facilitated. In this embodiment, the ultimate product could be a combination of the product with the associated nucleic acid.

In one embodiment, the product binds to the target and the bound nucleic acid-product-target complex can be partitioned from unbound products by a number of methods. The methods include nitrocellulose filter binding, column chromatography, filtration, affinity chromatography, centrifugation, and other well known methods. Briefly, the product library is subjected to the partitioning method, such as a column onto which the target is bound. All nucleic acids which have not formed products or those associated with undesirable products will pass through the column. Additional undesirable products (e.g., products which cross-react with other targets) may be removed by Counter-SELEX™. Desirable products are bound to the column and can be eluted by changing the conditions of the column (e.g., salt, etc.) or the nucleic acid associated with the desirable product can be cleaved from the product and eluted directly.

Additionally, products which react with a target can be separated from those products that do not react with the target. In one example, a product which covalently attaches to the target (such as a suicide inhibitor) can be washed under very stringent conditions. The resulting product-target complex can then be treated with proteinase, DNAse or other suitable reagent to cleave a linker and liberate the nucleic acids which are associated with the desirable products. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

As described earlier, the SELEX™ process can include other embodiments which could be incorporated for the successful partitioning of desirable products, including but not limited Photo-SELEX™, Counter-SELEX™, etc.

Inherent in the Parallel SELEX™ methodology is the selection of small molecules on the basis of a desired function; this can be extended to the selection of small molecules with a desired function and specificity. Specificity can be required during the selection process by first extracting RNAs attached to products which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a Parallel SELEX™ process-generated product library by first removing those products capable of interacting with the mammalian cytochrome, followed by retention of the remaining products which are capable of interacting with the fungal cytochrome.

In one embodiment, before the partitioning step, the nucleic acid is treated in such a way that it is less likely to interact with the target. As an example, the nucleic acid can be made double stranded or treated by pH reversible glyoxal denaturation before partitioning. In another embodiment, prior to coupling the reactant to the nucleic acid, the nucleic acid test mixture can be partitioned via Counter SELEX™ to eliminate nucleic acids which act directly on the target.

F. Amplification

Amplification of the nucleic acid that directs the synthesis of the product having desirable characteristics is done as described in the basic SELEX™ method using methods known to one of ordinary skill in the art. If necessary or desirable, any modification or other added feature (such as the linker group) may be removed prior to amplification. Polymerase chain reaction (PCR) is an exemplary method for amplifying nucleic acids. Descriptions of PCR methods are found, for example in Saiki et al., 1985. *Science* 230:1350–1354; Saiki et al., 1986. *Nature* 324:163–166; Scharf et al., 1986. *Science* 233:1076–1078; Innis et al., 1988. *Proc. Natl. Acad. Sci.* 85:9436–9440; and in U.S. Pat. No. 4,683,195 (Mullis et al.) and U.S. Pat. No. 4,683,202 (Mullis et al.). In its basic form, PCR amplification involves repeated cycles of replication of a desired single-stranded DNA, or cDNA copy of an RNA, employing specific oligonucleotide primers complementary to the 3' and 5' ends of the ssDNA, primer extension with a DNA polymerase, and DNA denaturation. Products generated by extension from one primer serve as templates for extension from the other primer. Other known amplification methods are contemplated by this invention.

Strand Displacement Amplification (SDA) is one example of an alternative partitioning method (Walker et al., 1992. *Proc. Natl. Acad. Sci.* 89:392–396; Walker et al., 1992. *Nucleic Acids Research* 20:1691–1696). SDA is a technique for amplifying ssDNA from ssDNA which shares some similarities to PCR. Like PCR, SDA uses a set of two convergent primers to amplify the DNA which lies between the primers and requires the activity of a DNA polymerase to accomplish this. Also, SDA uses an exponential amplification scheme in which newly synthesized DNA serves as a template for further DNA synthesis. Unlike PCR, SDA is carried out at a constant temperature (~40 deg. Celsius) and relies on the ability of a certain class of polymerases to displace a previously synthesized DNA strand off of the template as it synthesizes a new strand. This replaces the thermal denaturation step used in PCR. SDA requires the action of an additional enzyme, a restriction endonuclease, to generate a nick in a dsDNA template. The DNA on the 3' side of the nick serves as a primer for new DNA synthesis, while the DNA on the 5' side of the nick is displaced into solution by the DNA polymerase, where it can anneal with one of the SDA primers and serve as template for more DNA synthesis. If DNA ligands are desired, SDA has a number of advantages for the Parallel SELEX™ process. The SDA method uses the DNA polymerase Klenow exo(-) for synthesis of DNA, a very well characterized polymerase which is known to add certain modified dNTPs easily. Being well characterized, rational decisions about which modified dNTPs to make should be easier to make. A simple scheme could be devised in which primer extension replaces ligation for the joining of the DNA ligand to the tethered reactive group. SDA has amplification properties similar to PCR (for DNA <200 nt long), but can be accomplished using less specialized equipment in a shorter time.

The amplified nucleic acid then is subjected to any required post-amplification modification, recoupled to the first reactant and the process continues as described above. The process is repeated as many times as necessary to enrich for nucleic acids having the appropriate facilitating activity and/or until desirable products having maximal desirable characteristics are obtained. It is entirely possible that one round of the Parallel SELEX™ process is all that is required to obtain a product having desirable characteristics. The endpoint can be determined by many methods which would be understood by one of ordinary skill in the art, including binding curves, inhibition determined by $IC_{50}$ values, rates of inactivation, toxicity profiles, bioavailability, pharmacokinetics, etc.

G. Analyzing Desirable Products

After amplifying the nucleic acid facilitator and producing sufficient quantities of the desirable product, the structure of one or a series of desirable products can be solved by conventional spectroscopic methods known to one of ordinary skill in the art. In order to do this, the initial reaction conditions must be suitably replicated. The first reactant should be recoupled to the nucleic acid facilitator, the resulting nucleic acid-reactant mixed with the pool of second reactants and the resulting desirable product formed and isolated. The assumption that enables this process to be most effective is that the nucleic acid will specifically facilitate the individual reactions or at least a relatively small number of reactions, including the desired reaction. The conventional characterization methods include, but are not limited to, NMR spectroscopy, mass spectroscopy, HPLC-coupled spectroscopy, infrared spectroscopy, UV/visible spectroscopy, circular dichroism, polarimetry, and X-ray crystallography. Once the structure of the desirable product has been identified, it can be produced in large quantities either by standard chemical synthesis procedures or by the procedures outlined herein for production using a facilitating nucleic acid.

III. Generic Examples

The following generic examples are included to additionally describe the Parallel SELEX™ method. The most basic scheme for the Parallel SELEX™ method is outlined in FIG. 1. The following examples describe in more detail a small sampling of reactions that are contemplated by the invention. It is intended that these examples are provided for illustration purposes only and are not meant to limit the invention in any way.

A. A Diels-Alder Reaction

The following discussion describes how RNA facilitators and a cyclohexene small molecule product which will bind to a generic target may be coevolved utilizing the Diels-Alder reaction depicted in FIGS. 2A–2D. Another version of this Parallel SELEX™ example could employ DNA and in some cases DNA may be preferable to RNA.

The starting RNA (A of FIG. 2A) would contain 3' and 5' fixed regions to allow for transcription and a ligation site for conjugation to a PEG spacer which is in turn connected to a first reactant dienophile. The starting RNA (A) will have a randomized region consisting of approximately $4^N$ different sequences, wherein N is the number of nucleotides in the RNA sequence; the exact number will depend on the length of the random region and the scale of RNA synthesis used to make it. The PEG spacer would contain a sufficient number of polymeric units to allow for a flexible tether that would enable the first reactant dienophile access to the entire surface and binding pockets of the folded RNA (C and D of FIG. 2A. The starting RNA (A) which is coupled to the first reactant is depicted as a linear structure for the sake of clarity. The actual RNA structures will consist of different folded motifs as represented by C and D.

Figure 2A:
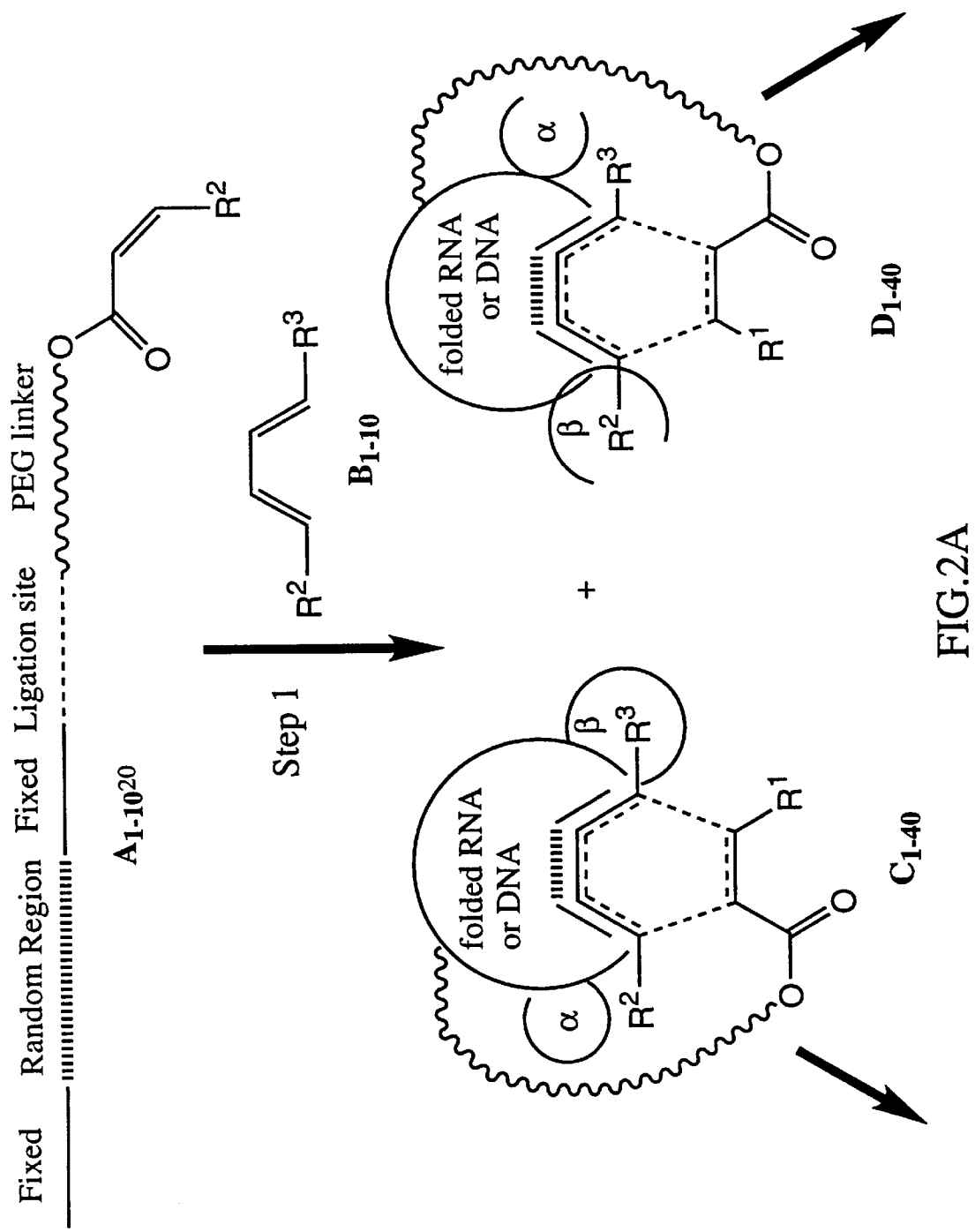
FIGS. 2A–D depict a schematic representation of the Parallel SELEX™ process wherein a facilitating nucleic acid mediates a generic Diels-Alder reaction between a diene and a dienophile.
Figure 2B:
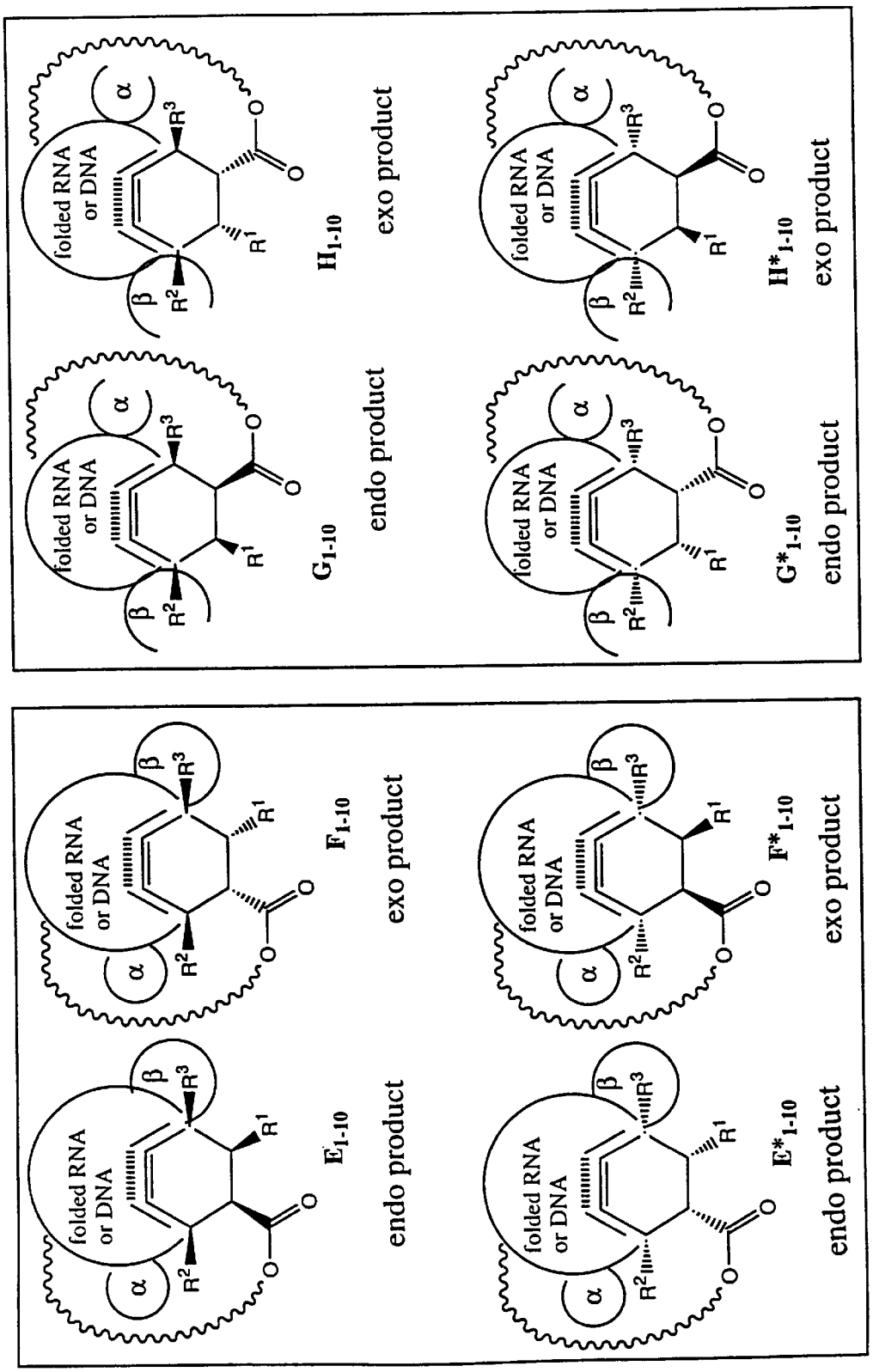

In this example, Step 1 will include a pool of 10 second reactant diene substrates labeled $B_{1-10}$ where the groups $R^1$, $R^2$ and $R^3$ are not hydrogen. There is no reason that the pool could not be expanded to include second reactant dienes where one or all of the groups $R^1$, $R^2$ and $R^3$ are hydrogen. This would only result in a fewer number of stereocenters being formed. Structures C and D represent the two possibilities for approach of the first reactant dienophile. Each regioisomer will have four possible stereoisomers that may form and if all are produced, 11 compounds will be transformed into 80 (FIG. 2B). Diagrammatic structural elements α and β represent theoretical bulges in the RNA that can interact with the second reactant diene or first reactant dienophile to determine the orientation of the second reactant diene and the approach of the second reactant diene at the transition state. For example, for $E_{1-10}$ if $R^3$ is smaller than $R^2$ the preferred orientation of the diene would favor formation of E/E* and F/F* in contrast to G/G* and H/H* because of steric interference between the RNA features β and dienophile group $R^2$. For approach C, enantiomers E/E* and F/F* will be formed. Attractive interaction such as H-bonding between the dienophile carboxylate oxygen and the RNA region labeled a would facilitate formation of the endo products. Attractive forces between $R^1$ and the RNA surface labeled β could also favor endo attack. In contrast, the RNA structural features α and β could have repulsive interactions with the carboxylate and $R^1$ of the dienophile which would result in formation of the exo products. Note that the relationship between the pairs E/E* and F/F* is diastereomeric so they will have different physical properties even for identical substituents $R^1$, $R^2$ and $R^3$. For approach D, enantiomers G/G* and H/H* will be formed and the relationship between the pairs G/G* and H/H* is diastereomeric. However, because the oligonucleotide has inherent chirality, the RNA facilitative site will have an energetically different, diastereomeric interaction with the transition state of the enantiomeric pairs which could allow for high enantioselectivity even if the energy difference is small ($\Delta\Delta G\ddagger$ 3–4 kcal/mol).

Figure 2C:
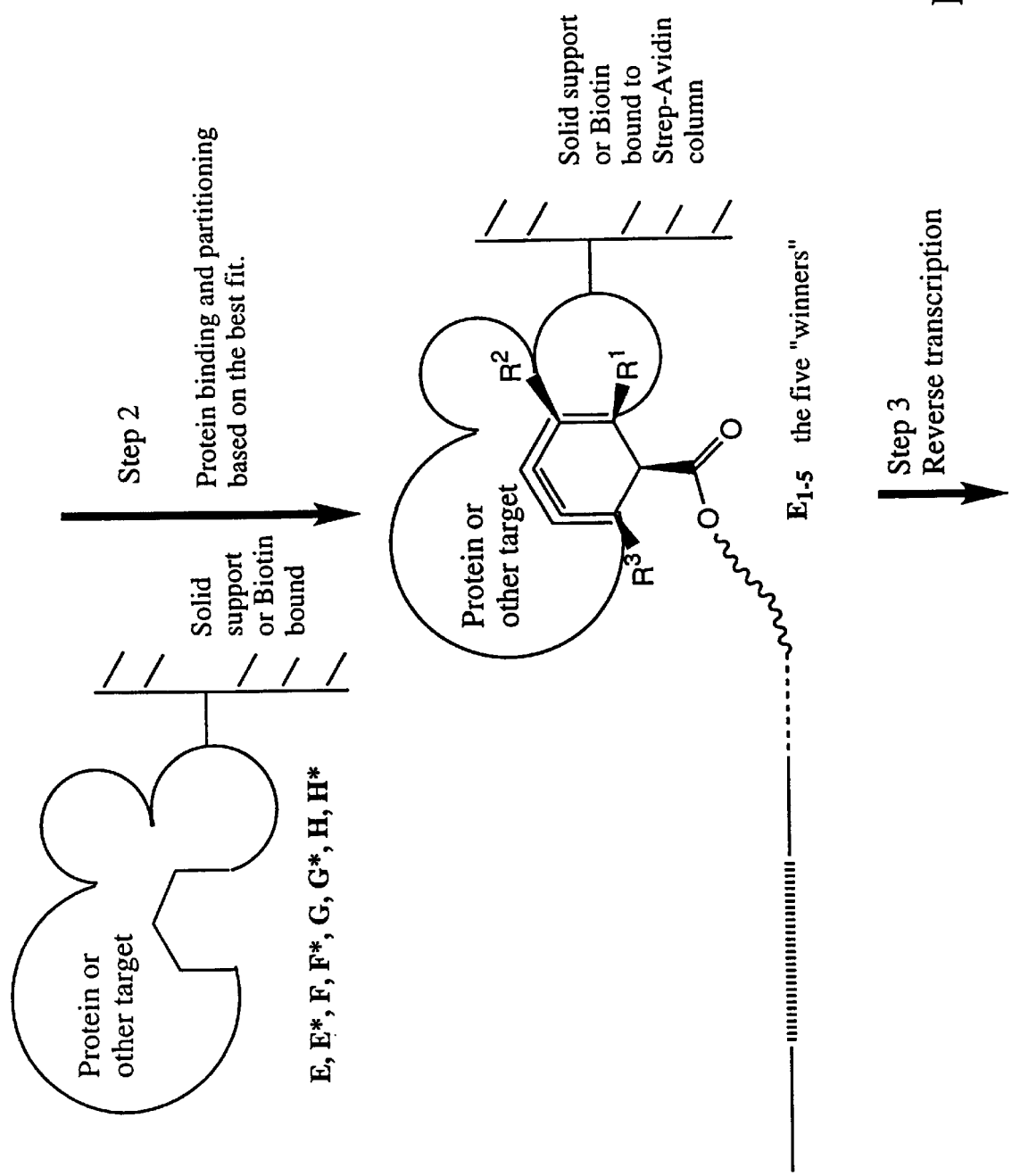

The selection of the cyclohexene desirable products is described by Step 2 (FIG. 2C). If the target is a protein and the desirable product is selected for binding to the target, Step 2 could be performed in target protein excess during initial rounds and the protein concentration would then be decreased as enrichment of the cyclohexene desirable product increases. Examples of target proteins could include enzymes, hormones, cell receptors, cell adhesion molecules etc. In a competition assay the highest affinity desirable products will be bound. This could result initially in the selection of entire groups such as E/E* and F/F*. For this example it is assumed that one enantiomer set is selected, say E, because it binds more tightly to the target protein, and for the sake of an example only 5 of the 10 possible structures are of comparable affinity. E1–5 depicts the five "winners" which bound to the protein. (It will be noted that there is no a priori reason to believe that desirable products could not be obtained that were derived from each of the diastereomers.)

Figure 2D:
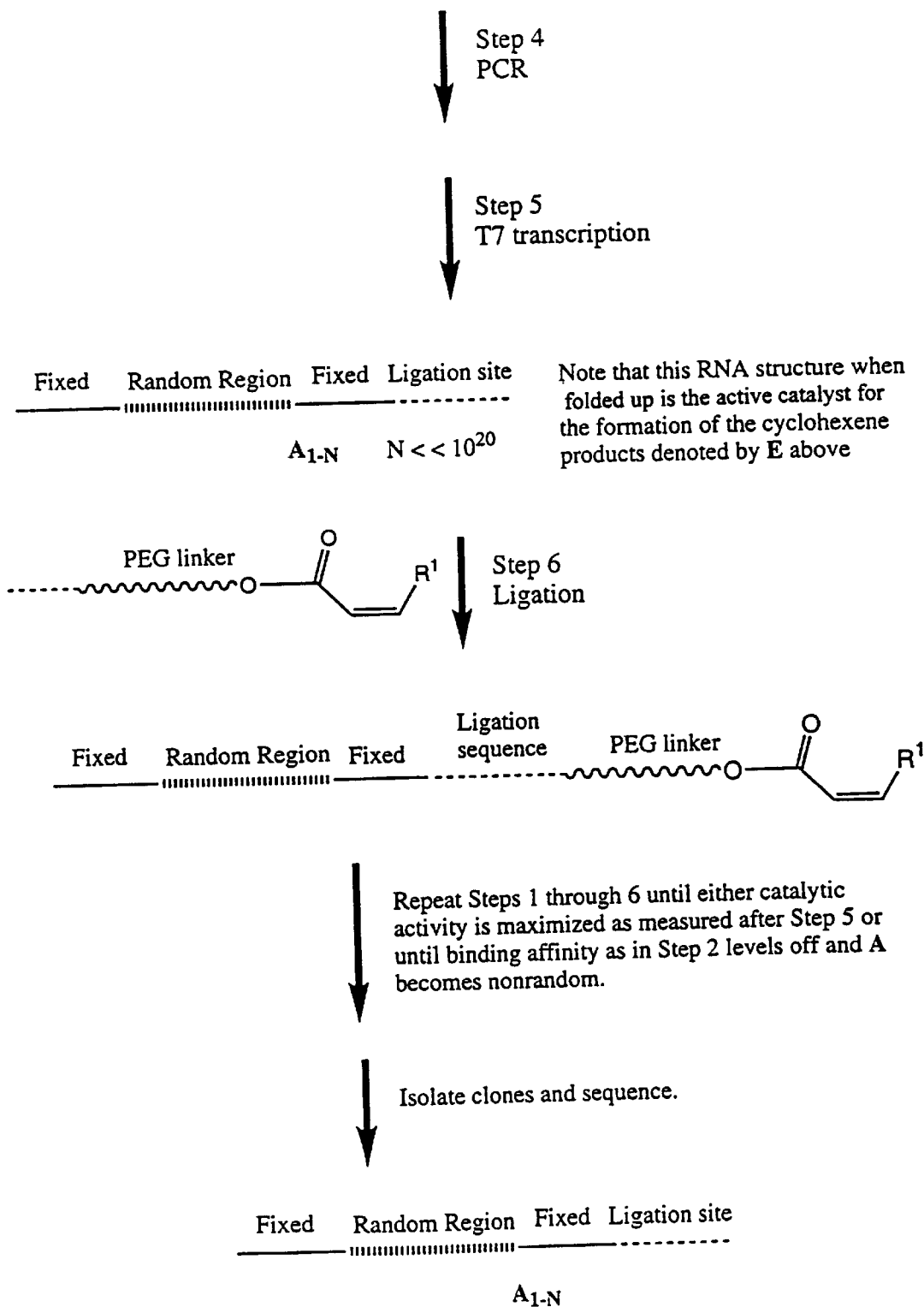
Figure 3A:
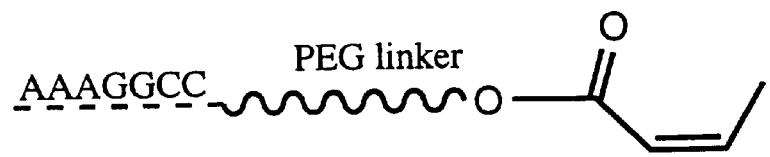
FIGS. 3A–E depict how ligation sequences may be used to expand the array of second reactant molecules in the Parallel SELEX™ process. Five of the possible 16,384 possibilities consistent with FIG. 2 are shown.
Figure 3B:
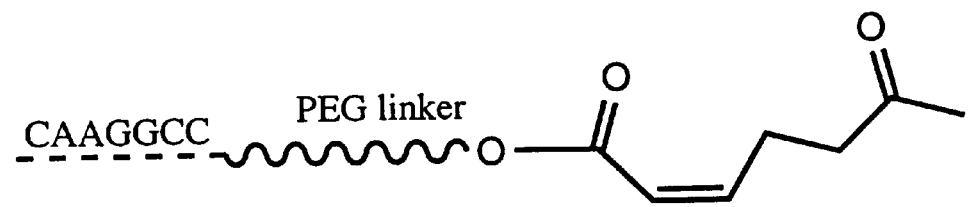
Figure 3C:
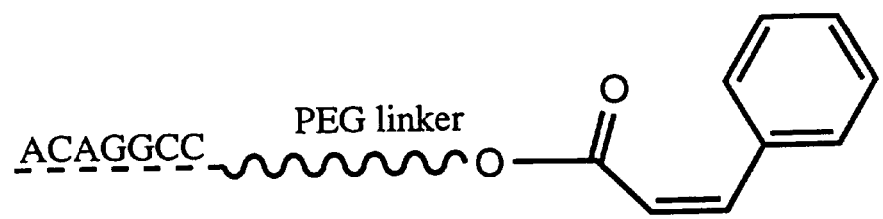
Figure 3D:
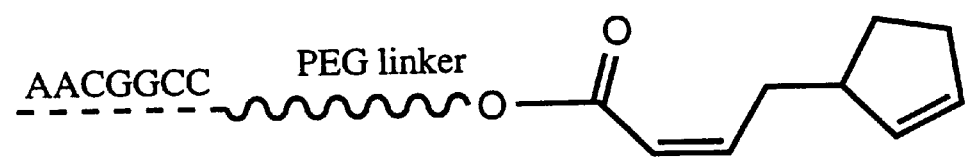
Figure 3E:
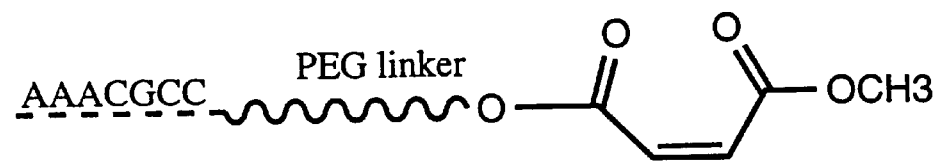

The selected desirable products and their attached, coevolved RNA facilitators are partitioned from the undesirable products and the RNA facilitators are amplified by the standard SELEX™ procedures of Steps 3 through 5 (FIGS. 2C and 2D). After Step 5, the RNAs have been enriched for facilitating activity that specifically forms the E group of compounds. The RNA structure obtained after step 5 when folded up is the active catalyst for the formation of the cyclohexene products denoted by E in FIG. 2C. There could be many more than 5 RNA sequences at this point. To perform subsequent rounds of SELEX™ would require Step 6 in which the initial PEG spacer with first reactant dienophile is ligated to the new enriched pool of RNAs. Repeating Steps 1 through 6 could further enrich for the facilitating activity of the RNA obtained after Step 5. Additionally, the binding affinity of the cyclohexene desirable products could reach a maximum. Assuming that the RNA pool is now non-random, by cloning and sequencing the different RNAs the individual RNA molecules could be tested for their facilitating activity. Treating these RNA molecules with the same first and second reactant dienophile and dienes would by necessity result in the formation of the coevolved cyclohexene desirable product. After producing sufficient quantities of the RNA facilitator, the structure of one or a series of cyclohexene desirable products is solved by conventional spectroscopic methods.

The example given above was for a single first reactant dienophile treated with a pool of 10 second reactant dienes. The number of first reactant dienophiles to be included in the coevolution process may be expanded by simply attaching a number of different first reactant dienophiles to the ligation sequence. After coevolution, cloning and sequencing the individual RNA facilitators would then be treated with the mixture of first and second reactant dienes and dienophiles so that the individual desirable product formed by the facilitating RNA would be made in sufficient quantity to allow for spectroscopic structural identification. Since in the Parallel SELEX™ example shown above the first reactant dienophile is attached to the RNA it is assumed that the facilitating RNA will be specific for reaction of the attached first reactant dienophile as opposed to those attached to other RNAs. It may turn out that treating a single facilitating RNA with a pool of first and second reactant dienes and dienophiles will result in a very specific reaction with respect to the second reactant diene, because this was what was selected for, but poor selectivity for the first reactant dienophile, since this is attached during the selection.

On the other hand, if both first and second reactants are varied, specificity for both reactants could be obtained. An improved embodiment would be to use the ligation sequence to code for the first reactant dienophile that is attached to a particular nucleic acid as shown in FIG. 3, and thus allowing for the matrix to be expanded. Using this approach, on cloning and sequencing of the individual facilitating RNAs the sequence of the ligation site would indicate the first reactant dienophile that was attached to it through the PEG linker. In this way only the first reactant dienophile corresponding to the particular facilitating RNA would be used for the final preparation of the evolved desirable product. It should be noted that there is no reason why a complementary experiment to the one proposed in FIG. 2 could not be employed where a single first reactant diene is attached to the RNA ligation sequence and a pool of second reactant dienophiles introduced into Step 1. It is also possible to use multiple first reactants and one second reactant.

The Diels-Alder is only one of a number of very powerful asymmetric bond forming reactions.

B. An Aldol Reaction

Figure 4A:
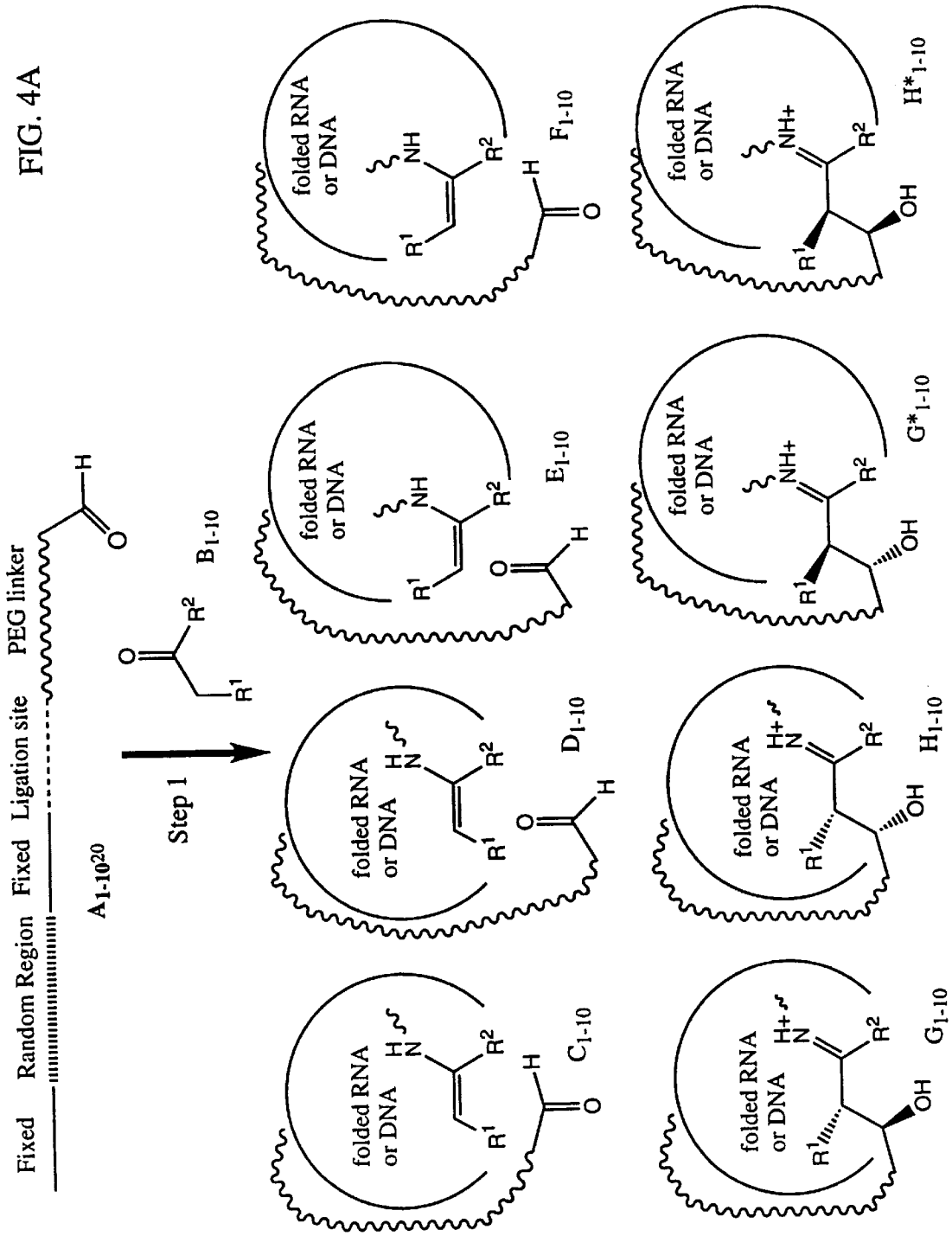
FIGS. 4A–C depict a schematic representation of the Parallel SELEX™ process wherein a facilitating nucleic acid mediates a generic bond forming Aldol condensation reaction between a ketone and an aldehyde.
Figure 4B:
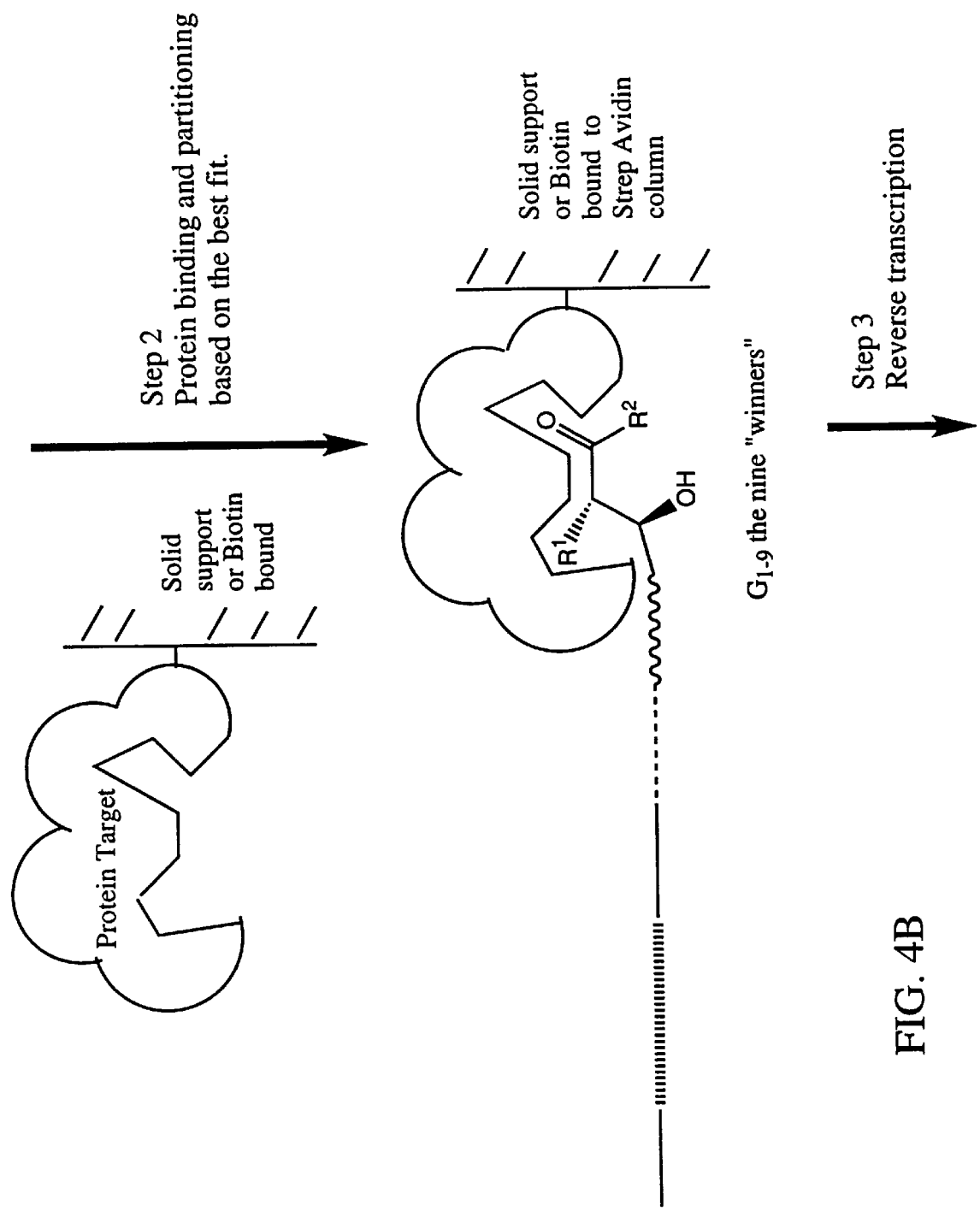
Figure 4C:
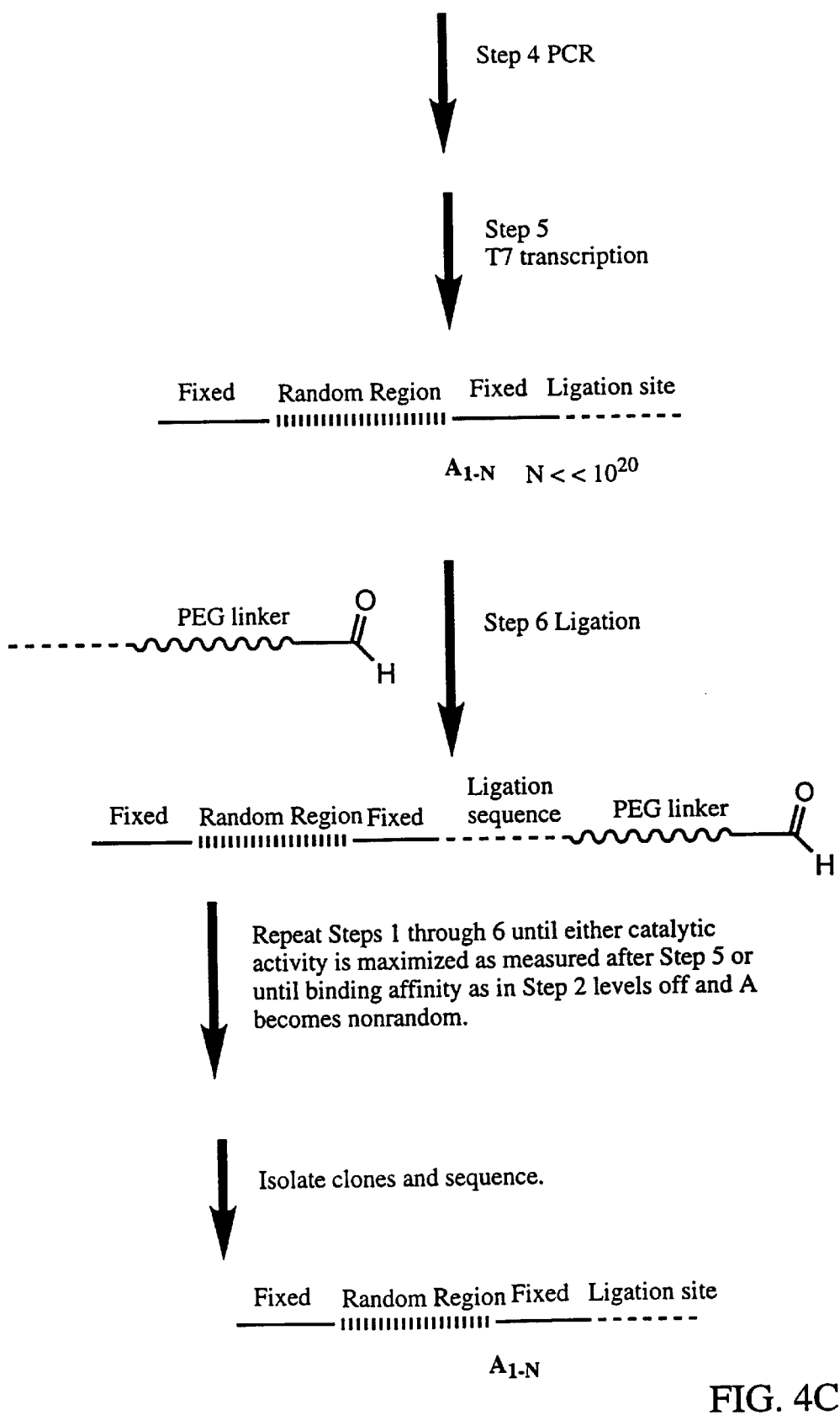

Another reaction type useful in synthetic and biosynthetic chemistry is the Aldol condensation. The basic concepts discussed for the Diels-Alder reaction apply to the Aldol reaction wherein one or more aldehyde are one reactant and one or more ketone are another reactant. A logical variation of how to tailor the Parallel SELEX™ process to an Aldol condensation is described in the following example and FIGS. 4A–4C. The RNA (or DNA) is comprised of a 3' and 5' fixed region for transcription. Attached to the RNA is a PEG linker (20–50 ethylene units long) which in turn has a first reactant aldehyde connected. The first reactant aldehyde will serve as the electrophile in the Aldol reaction by virtue of its greater reactivity as compared to a second reactant ketone. The pool of RNA sequences labeled A would fold up into different structural motifs. Second reactant ketones labeled $B_{1-10}$ with different chemical groups $R^1$ and $R^2$ would be treated with A in Step 1 of FIG. 4. In this example, the RNA contains an amine capable of adding to the carbonyl of the ketones and forming an enamine as denoted by $C_{1-10}$, $D_{1-10}$, $E_{1-10}$ and $F_{1-10}$. The shape of the RNA will determine whether the E- or Z-enamine is formed. The enamine would then serve as a nucleophile in the Aldol reaction with the appended aldehyde. The steric and electronic environment of the RNA surrounding the enamine will determine the degree of enantioselectivity observed for a given RNA sequence.

For the purposes of this example the Aldol condensation products $G_{1-10}$, $H_{1-10}$, $G^*_{1-10}$ and $H^*_{1-10}$ are derived from attack of the first reactant aldehyde from the same face. It is possible to form the same product by approach from the opposite face if a different enamine and relative orientation of the first reactant aldehyde occurs and this is likely to happen. It is important that for the two new chiral centers being formed that all forty products are represented as $G_{1-10}$, $H_{1-10}$, $G^*_{1-10}$ and $H^*_{1-10}$. Aldol products $G_{1-10}/G^*_{1-10}$ are enantiomers as are $H_{1-10}/H^*_{1-10}$.

In water the imine linkage of $G_{1-10}$, $H_{1-10}$, $G^*_{1-10}$ and $H^*_{1-10}$ will be reversible and hydrolyzed to give the corresponding β-ketoalcohol products. Selecting the highest affinity β-ketoalcohol desirable products will be accomplished by partitioning the resulting product library with the protein target linked to biotin or a column support. After allowing for equilibration the selected RNA is amplified by standard SELEX™ techniques as shown by Steps 3–5 in FIG. 4C. The RNA obtained after Step 5 when folded up is the active catalyst for the formation of the Aldol β-ketoalcohol products denoted by G1–9.

Once a maximum level of facilitation is achieved or the affinity of binding to the target levels off, the facilitating RNA associated with desirable products would be cloned and sequenced. The facilitating RNA could then be prepared separately and the synthesis of their corresponding β-ketoalcohol desirable products performed on a scale sufficient for isolation followed by structural characterization by spectroscopic methods.

As with the Diels-Alder example, the array of first reactant aldehydes employed in the Parallel SELEX™ process could be expanded by attaching different first reactant aldehydes to the PEG linker and encoding the ligation sequence for which first reactant aldehydes were attached to which nucleic acids.

From the Diels-Alder reaction example discussed above, a factor of 4 is obtained for the creation of two stereocenters. However, the Aldol condensation has the potential to form many more possibilities than this. Consider the mixed Aldol reaction where two ketones are used as first and second reactants that have comparable electrophilicity at the carbonyl carbon and similar nucleophilicity at the α-carbons (FIG. 5). Typically in organic synthesis this type of reaction is avoided because a very complex mixture of products can result. In the Parallel SELEX™ strategy this increase in diversity could be of added benefit. Structures C, D, E, F, G, H, I and J are all different diastereomers. Each of these products has a corresponding enantiomer, which means that for the mixed Aldol condensation reaction of FIG. 4, 1600 products with different structures would be formed from the original 20 ($A_{1-10}$ and $B_{1-10}$).

C. [2+2+2] Cyclotrimerization Reactions

Parallel Selection and coevolution of both the facilitating RNA and the desirable product is not limited to the formation of products having structures that create chiral centers. Many important medicinal compounds contain achiral aromatic groups with appended chiral substituents. One of the most powerful methods for the construction of products comprising aromatic ring systems (benzenes, naphthalenes, pyridines etc.) is cyclopentadienyl cobalt (CpCo) mediated cyclotrimerization of first, second and third reactant alkynes. It should be noted that [2+2+2] cyclotrimerization is not limited to alkyne reactants and non-aromatic six membered ring products can be assembled by combining alkyne and alkene reactants.

The example discussed here includes the embodiment of the invention where an organometallic catalyst is incorporated in the RNA (or DNA) and its use in the Parallel SELEX™ process. Steps 1–6 described above and shown in FIGS. 2 and 4 are general to all Parallel SELEX™ processes so only the impact of cyclotrimerization on the potential number of product structures formed will be discussed here. For cyclotrimerization of three alkyne reactants to form a product including a benzene ring the maximum number of possibilities is obtained using three different alkyne reactants that have different substituents attached to each end of each reactant (depicted in FIG. 6).

Figures 6A, 6B:
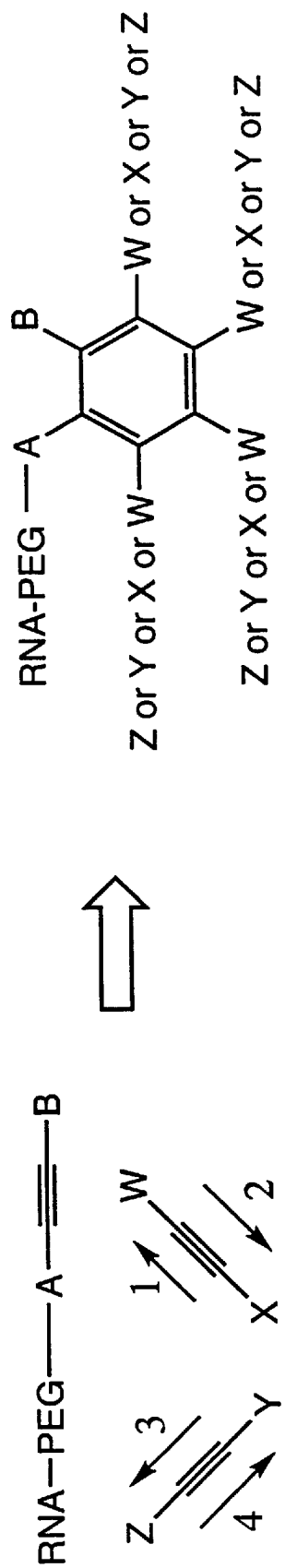
FIG. 6A depicts the cyclotrimerization of three alkynes to yield a substituted benzene ring.
FIG. 6B depicts a matrix of possibilities for the assembly of benzene compounds by cyclotrimerization of the three alkynes depicted in FIG. 6A.
Figure 6C:
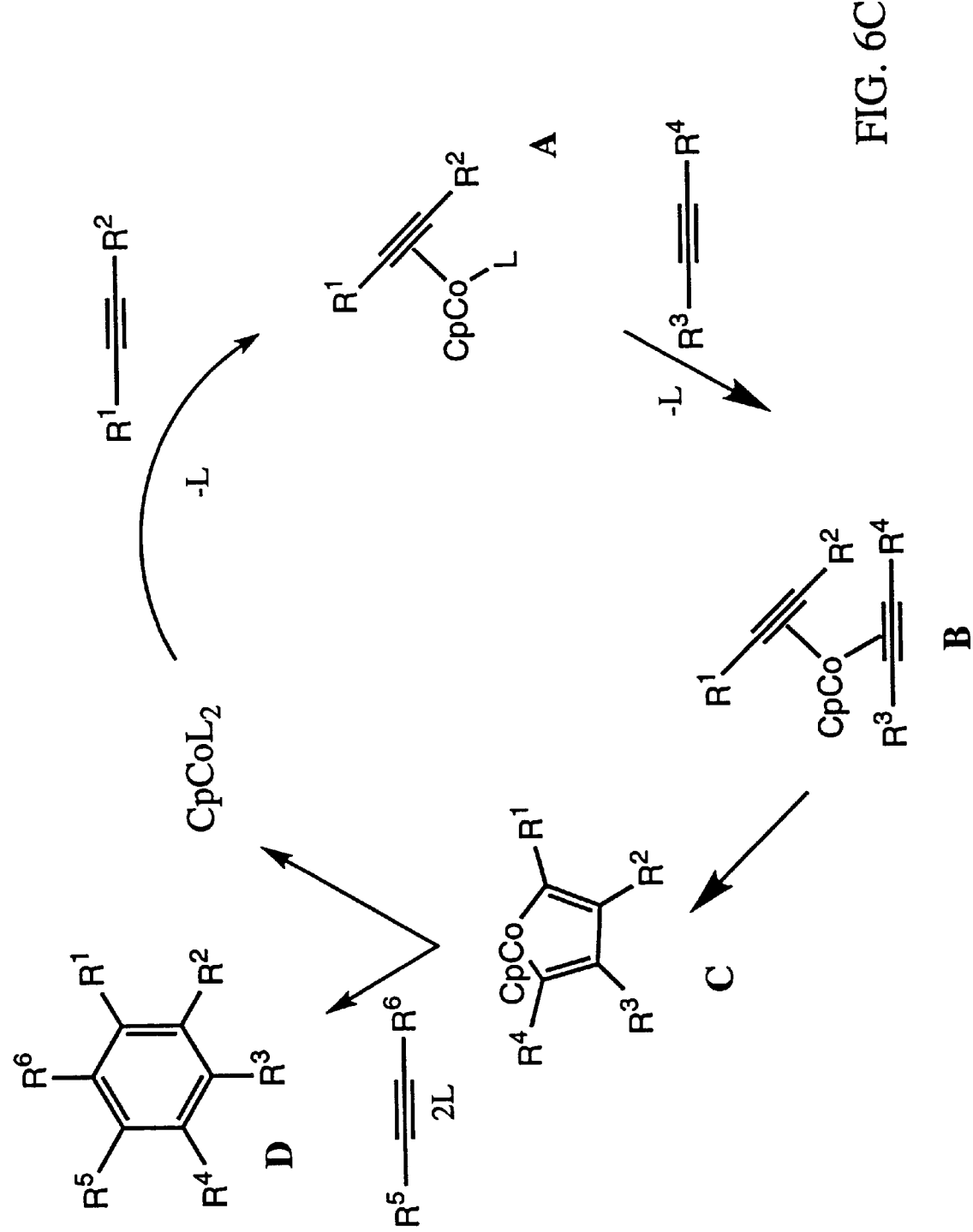
FIG. 6C depicts the mechanism of cyclotrimerization of alkynes. Only one of the possible products is shown.

For a cyclotrimerization of alkyne reactants as shown in FIG. 6 there are $4MN^2$ possible regioisomer products where M=the number of nonsymmetric alkyne first reactants attached to the RNA and N=the number of free nonsymmetric alkyne second and third reactants that are contacted with the RNA-first reactant mixture. FIG. 6 shows the matrix of possibilities for only 3 alkyne reactants, where the first reactant is attached to the RNA and the second and third reactants are free. If the Parallel SELEX™ process is expanded to include 10 alkyne first reactants attached to the RNA molecules and 10 second and third reactants there could be 4,000 benzene products made.

The mechanism of CpCo catalyzed cyclotrimerization of alkyne reactants is given in the bottom panel of FIG. 6. By attaching CpCo (or another metal complex capable of cyclizing alkynes) to an oligonucleotide as described above it may be possible to form a cyclotrimerizing facilitating RNA. RNA structures that are folded up around the organometallic center will provide a pocket that will impart selectivity in either of the bond forming steps depicted in FIG. 6, B→C or C→D. Employing the partitioning of the Parallel SELEX™ process should provide the specificity for the synthesis of the desired benzene products. On cloning and preparation of sufficient amounts of the facilitating RNA the coevolved aromatic product(s) may be prepared by treating the RNA with the mixture of alkyne reactants used in selection. The aromatic product obtained then can be structurally characterized by conventional methods.

D. Retrosynthetic Strategies

Figure 7:
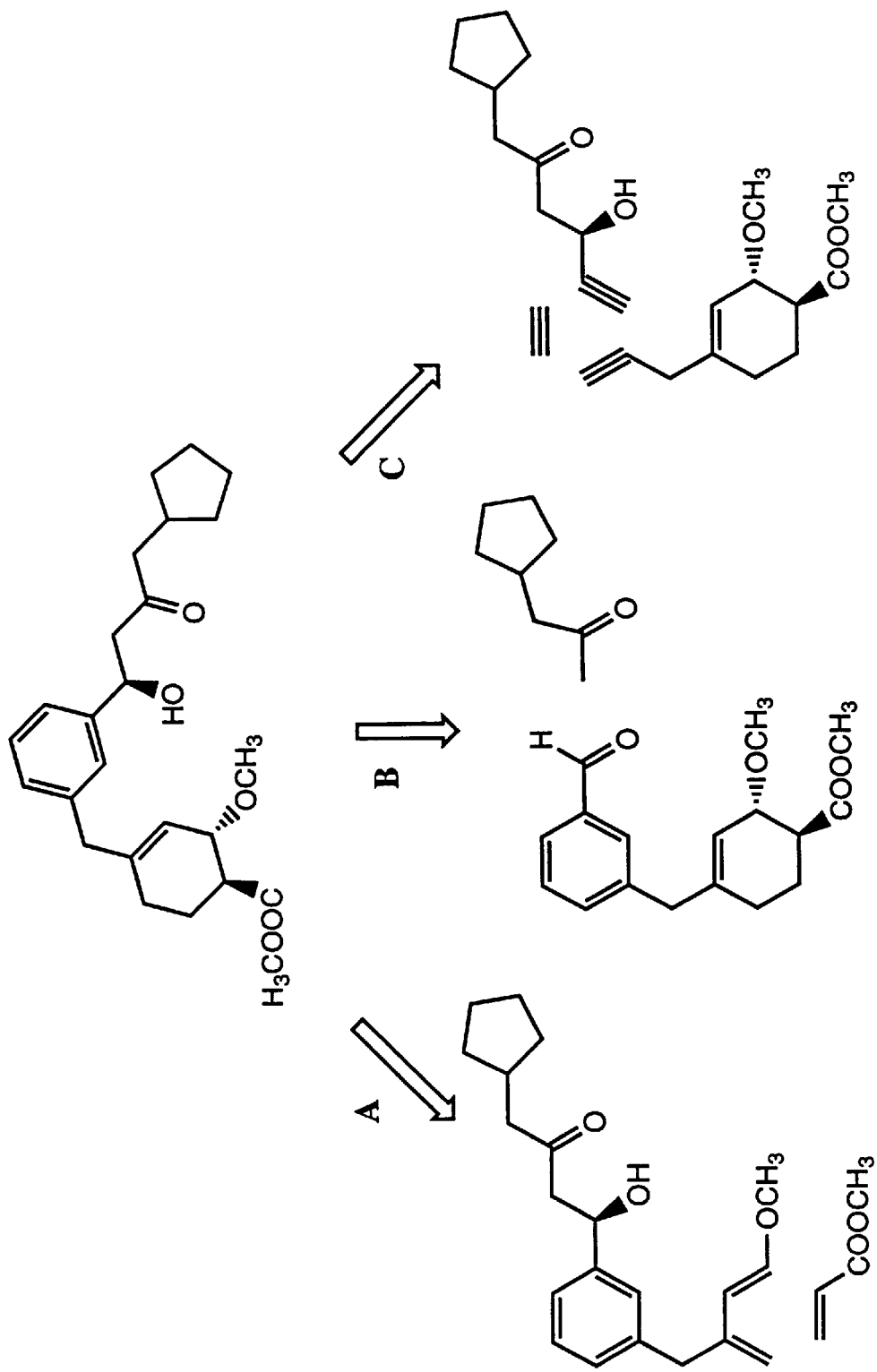
FIG. 7 depicts a possible strategy for retrosynthesizing a typical product of the invention.

In general it is envisaged that all Parallel SELEX™ schemes will have in common Steps 1–6 as described above and by FIGS. 2 and 4. Different chemistries will only change the type and number of products formed. When considering which chemistry or chemistries is best to include in the Parallel SELEX™ process it can be valuable to perform a retrosynthetic analysis on the structural product class of interest. Consider FIG. 7 and the possible disconnections for the product shown. Disconnection A would involve the Diels-Alder transformation and B the Aldol condensation. Both of these bond forming reactions were discussed above. There are many other disconnections that could be made for this product. In general, retrosynthetic strategies that include ring forming product transformations are desirable because the greatest number of bonds or stereocenters are formed. When considering which types of reactions are most powerful for the Parallel SELEX™ process other factors may need to be considered. For example, the availability of reagents and the reactivity and stability of the oligonucleotides under the reaction conditions. Of significant importance is the number of possible stereo or regioisomer products that may be formed. While the Diels-Alder and Aldol condensation reactions have the potential to create a large number of products as a result of the formation of new stereocenters, the retrosynthetic path C can provide a significant number of regioisomer products. It is contemplated that the invention can include several chemical reactions, involving one or more facilitating nucleic acids and two or more different reactants, either simultaneously or sequentially, to make the products of the invention.

E. Counter-SELEX™ Strategies

Inherent in the Parallel SELEX™ methodology is the selection of small molecules on the basis of a desired function; this can be extended to the selection of small molecules with a desired function and specificity. Specificity can be required during the selection process by first extracting RNAs attached to products which are capable of interacting with a non-desired "target" (Counter-SELEX™, negative selection, or counter-selection), followed by positive selection with the desired target. Applications of this technique include, but are not limited to, the selection of small molecules which interact only with a single isoform of a multi-isoform enzyme, selection of small molecules capable of binding to a family of receptors, selection of small molecules that can differentiate between closely related receptors, selection of small molecule inhibitors of important enzymes/receptors of eukaryotic pathogens that do not inhibit the mammalian counterparts, etc.

Examples of targets that would be applicable to this technique include, but are not limited to, cyclooxygenase, inosine monophosphate dehydrogenase, and fungal cytochrome P-450. Cyclooxygenase, a target of anti-inflammatory drugs, catalyzes the peroxidation of arachidonic acid, which eventually leads to the formation of the classical prostaglandins (PGD$_2$, PGE$_2$, and PGF$_{2\alpha}$), prostacyclin (PGI$_2$), and thromboxane A$_2$ (TXA$_2$). Currently available inhibitors include non-steroidal anti-inflammatory drugs (NSAIDS). Gastric ulceration, which results from prostaglandin inhibition, is a fairly common side effect of these drugs. There are two isoforms of the target enzyme; Cox1 and Cox2. The Cox1 isoenzyme is constitutively expressed in most cell types, whereas Cox2 is rapidly inducible by LPS in monocytes and by IL-1 in fibroblasts (inflammatory tissues express Cox2). By applying the Parallel SELEX™ method/Counter-SELEX™ method, it could be possible to select small molecule inhibitors of Cox2 that do not cross-react with Cox1. It is expected that selective inhibition of Cox2 would result in anti-inflammatory activity without gastrointestinal erosion.

Type II inosine monophosphate dehydrogenase (Type II IMP dehydrogenase) is an important immunosuppressive drug target. The de novo synthesis of guanosine nucleotides, which requires IMP dehydrogenase, appears to be required for proliferative responses of human T and B lymphocytes to antigenic and mutagenic stimulation. Type I IMP dehydrogenase is expressed in resting cells, including lymphocytes, while Type II IMP dehydrogenase is rapidly induced when T and B lymphocytes respond to proliferative signals. The Parallel SELEX™ method/Counter-SELEX™ method could be used to select small molecule inhibitors (immunosuppressive drug leads) of the Type II enzyme with low or no cross-reactivity with the Type I enzyme.

Fungal cytochrome P-450 is an important anti-fungal drug target and will be used here as an example of how a Parallel SELEX™ method/Counter-SELEX™ experiment could be performed. A function of P-450 is the C14 demethylation of lanosterol, a step in the synthesis of ergosterol (fungal cell membrane component). Current azole antifungal drugs (imidazoles and triazoles) target this cytochrome.

A potential method for identifying specific inhibitors of fungal cytochrome P-450 is outlined here. First, a product library is produced by reacting RNAs associated with first reactant(s) with free reactants. Next, the product library is contacted with mammalian cytochrome P-450 using one of the numerous possible partitioning protocols (described elsewhere), most preferably by contact with mammalian cytochrome P-450 immobilized on a solid support. Products with an affinity for the mammalian cytochrome are thereby partitioned from the remainder of the product library. The products not retained by the mammalian cytochrome are recovered and contacted with fungal cytochrome P-450, by one of the numerous previously described partitioning methods, wherein products having specificity for the fungal cytochrome may be partitioned from the remainder of the product library. The products with an increased affinity for the fungal cytochrome are recovered and their associated nucleic acids are amplified. The selection and amplification process is repeated until the nucleic acid pool is sufficiently enriched in facilitating nucleic acids to permit identification of their associated products.

The Parallel SELEX™ retrosynthetic analysis of a known P-450 inhibitory pharmacophore is shown in the scheme below and serves as a non-limiting example of how the reactants may be chosen.

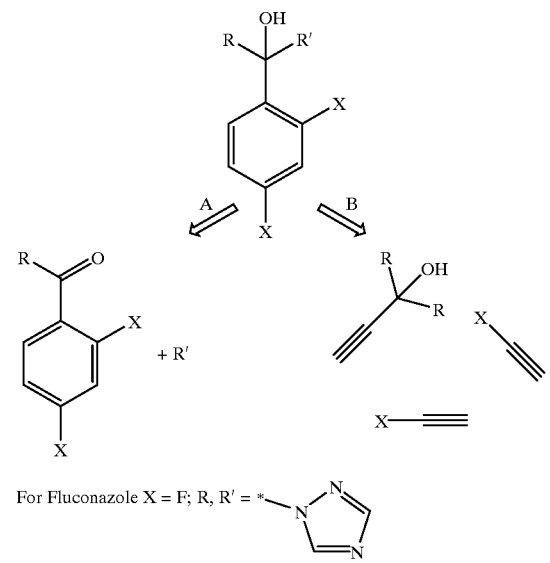

For Fluconazole X = F; R, R' = *

A large number of retrosynthetic strategies can be envisaged. Two obvious but not limiting strategies are depicted by A and B of the scheme above. Starting from any 2,4-disubstituted aromatic carbonyl compound, condensation with R' would give the corresponding benzyl alcohol. Examples of reaction types that could be used for strategy A include but are not limited to, Aldol and Claisen condensations where R' is an aldehyde, ketone, and ester, carboxylic acid, nitrile, or amide. In addition, strategy A could entail alkylation of heterocycles including imidazoles, triazoles, pyrazoles, pyridines, quinolines, indoles, oxazoles, pyrimidines and purines. Alternatively, strategy B would have as many as three different alkynes reacting in a cyclotrimerization reaction where X and or X' could be selected from all functional groups except carboxylic acids and Br and I. R and/or R' could be the same or different and selected from the group of all functional groups except carboxylic acids and Br or I.

F. Selectin Parallel SELEX™ Method

Binding of selectins to their natural, cell surface target, sialyl lewis X for example, has been implicated as a crucial step in the cascade of events responsible for inflammation. Molecules that inhibit this process have the potential to serve as anti-inflammatory agents in addition to preventing other selectin mediated events. The following outlines two Parallel SELEX™ strategies to elicit small molecule selectin ligands.

The general scheme of the two Parallel SELEX™ experiments is shown below. Both involve a derivatized sugar combining with a library of compounds. In one case the sugar has a nucleophilic functionality that can react with α,β unsaturated carbonyl compounds in a Michael addition fashion. The other strategy involves a diene functionalized sugar undergoing a Diels-Alder cycloaddition with either the same set of α,β unsaturated carbonyl compounds or with an entirely different library of dienophiles. The example shown utilizes a D-mannoside as the derivatized sugar because of its resemblance to the L-fucose of the natural ligand, but in principle could involve any molecule appropriately functionalized. Similarly, the Michael acceptor/dienophile library is unlimited, however one convenient strategy for generating a diverse pool of α,β unsaturated carbonyl compounds has been outlined below. A bias for certain functionalities in the library may be prudent based on the binding requirements known for sialyl lewis X mimics. For example, preservation of the sialic acid negative charge has been shown to be critical to binding. Consequently, the Michael acceptor/dienophile library should contain a significant population of members that have a negative charge somewhere on the molecule. Finally, partitioning can be carried out in a number ways, however methods that insure binding of the small molecule generated to the sialyl lewis X binding site are preferred. These include but are not limited to eluting with free sialyl lewis X or a known competitor or removing the required calcium ion from the protein with a chelator such as EDTA.

G. Synthesis of Pyridine Compounds Using the Parallel SELEX™ Process

A number of naturally occurring enzyme co-factors and drugs are derivatized pyridines, some of which are shown below. For example, nitropyridines are well known anti-cancer agents. Using a nitrile-cyclotrimerization Parallel SELEX™ process it would be possible to access functionalized pyridine pharmacophores. For example, pyridine derivatives could be generated that inhibit pyridoxal (Vit. $B_6$) dependent enzymes by mimicking key reaction intermediates. Similar experiments can be implemented to target nicotinic acid and nicotine receptors. Below are shown representative compounds that can be synthesized by this process.

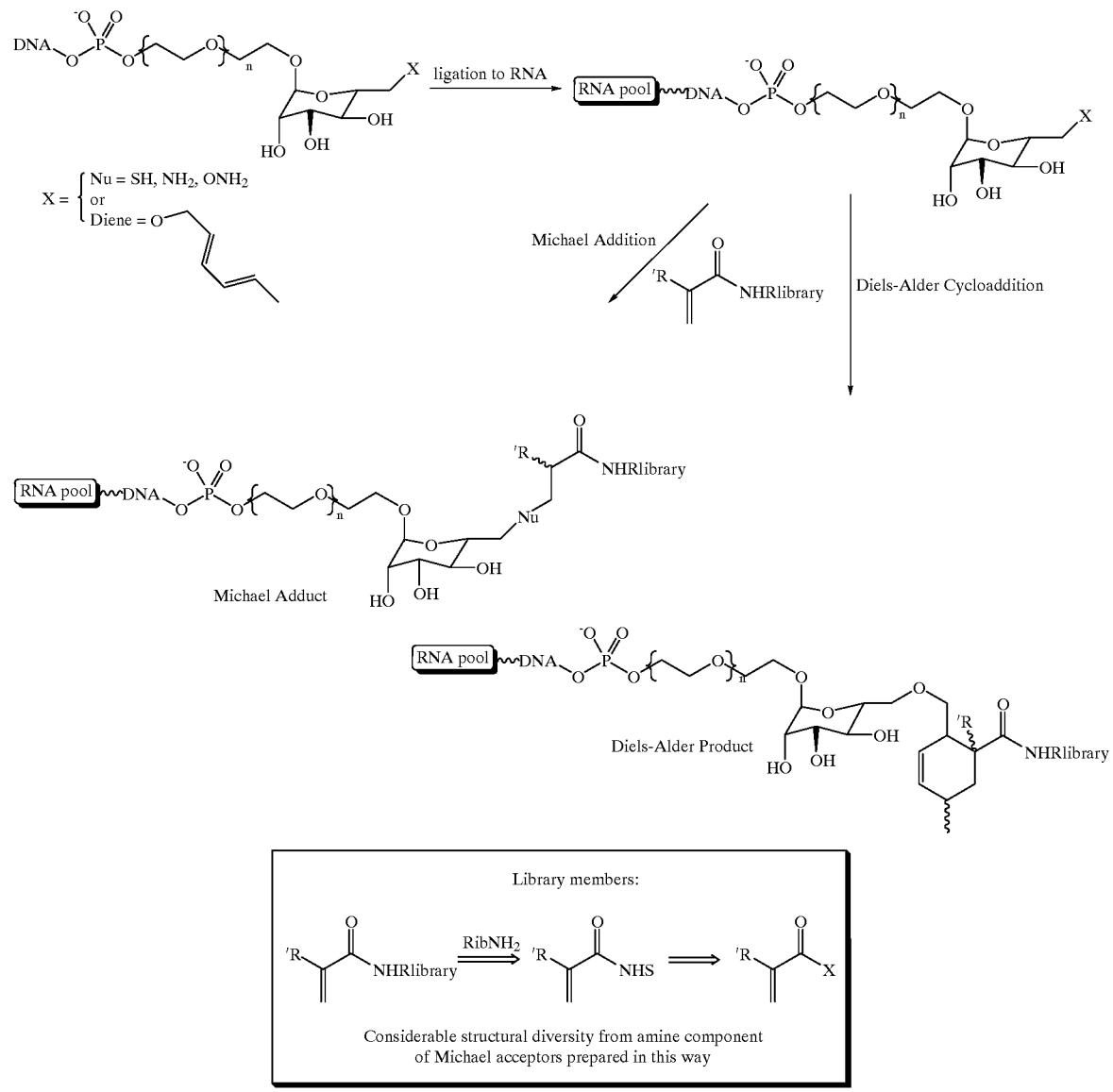

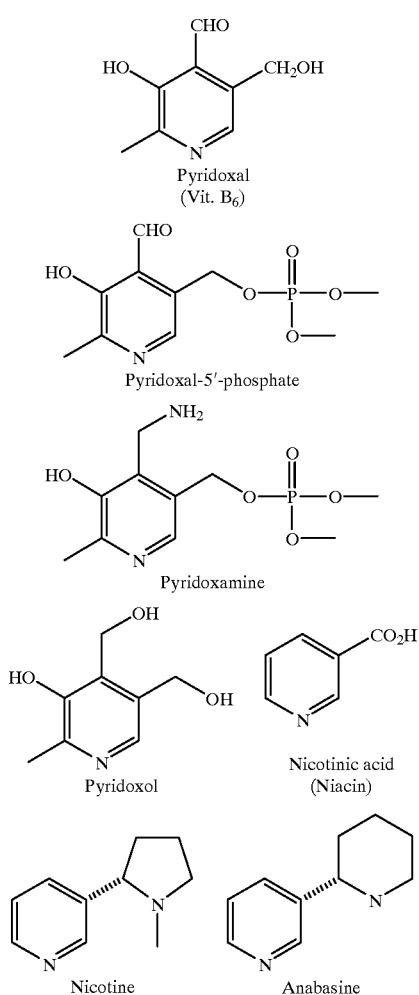

IV. Administration and Uses

Applications of the desirable products of this invention include various therapeutic, prophylactic, diagnostic, and cosmetic uses. Any use where a chemical product could be desirable is within the scope of this invention. Specific classes of conditions include, but are not limited to, inflammation, cardiovascular disorders, neoplastic conditions, metabolic disorders, parasitic diseases and infectious diseases. More specifically, the products of the invention are useful in treating or preventing cancer, angina, arthritis, asthma, allergies, rhinitis, shock, inflammatory bowel disease, low blood pressure, and systemic treatment of pain and inflammation, local trauma such as wounds, burns, rashes.

Preferred applications of the products of the present invention include, but are not limited to, treatment of hypertension and chronic inflammation, including angiotensin converting enzyme (ACE) inhibitors, and use as immunosuppressants, antibacterials and antifungals.

Particularly preferred targets include, but are not limited to, angiotensin converting enzyme, renin, cyclooxygenase, 5-lipoxygenase, IL-1β converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA$_2$, red blood cells, glioblastomas, fibrin clots, PBMCs, hCG, lectins, selectins, cytokines, ICP4, complement proteins, etc.

Anti-inflammatory drugs can be used for the treatment of acute and chronic inflammation and can include inhibitors of cyclooxygenase, 5-lipoxygenase, IL-1β Converting Enzyme (ICE), and cytokine receptors (e.g., IL-1 and TNF receptors and other receptors for pro-inflammatory cytokines).

There are two isoforms of the target enzyme: Cox1 and Cox2. The Cox1 isoenzyme is constitutively expressed in most cell types, whereas Cox2 is rapidly inducible by LPS in monocytes and by IL-1 in fibroblasts (inflammatory tissues express Cox2). Selective inhibition of Cox2 may result in anti-inflammatory activity without gastrointestinal erosion.

5-lipoxygenase, which is also involved in arachidonic acid metabolism, is necessary for the synthesis of the leukotriene hormones. The development of inhibitors of this enzyme has been hampered by the fact that it is regulated by several cofactors (Ca$^{++}$, ATP, phospholipids, etc.); it is, therefore, difficult to study in pure form. Current drug lead screening protocols require the use of whole cells. A Parallel SELEX™ procedure which utilizes the isolated enzyme may be applied to the selection of irreversible inhibitors with the need for a concomitant assay for enzyme activity.

Immunosuppressive drugs can include inhibitors of Type II inosine monophosphate dehydrogenase (Type II IMP dehydrogenase). The de novo synthesis of guanosine nucleotides appears to be required for proliferative responses of human T and B lymphocytes to antigenic and mutagenic stimulation (Allison, A. C. 1993. Annals New York Acad. of Sciences). Type I IMP dehydrogenase is expressed in resting cells, including lymphocytes, while the Type II enzyme is rapidly induced when T and B lymphocytes respond to proliferative signals. The Parallel SELEX™ process could be applied to the designing of a drug that is highly specific for the Type II enzyme (low or no cross-reactivity with the Type I enzyme).

Antifungal products include inhibitors of Fungal cytochrome P-450. A function of P-450 is the C14 demethylation of lanosterol, a step in the synthesis of ergosterol (fungal cell membrane component). Current azole antifungal drugs (imidazoles and triazoles) target this cytochrome. The Parallel SELEX™ process could provide a drug with improved selectivity for the fungal cytochrome P-450 (lower cross-reactivity with mammalian cytochrome P-450).

Products which are useful as steroid hormone agonists and antagonists are also included in the invention. It is believed that these products will be useful for treating breast, prostate, and cervical cancer. These products are also useful as birth control agents and arthritis remedies.

The desirable products of this invention, once identified by the Parallel SELEX™ method, can be produced for manufacture by conventional chemical synthesis routes or by using the facilitating nucleic acid to mediate the reaction between reactants. The products of the invention may contain an asymmetric atom(s). The asymmetric atom(s) can be selected from carbon, phosphorous, silicon, sulfur, to name a few. Thus, the invention includes the individual stereoisomers, and the mixtures thereof. The individual isomers may be prepared or isolated by methods known in the art.

The desirable products can be administered by any method known to one of ordinary skill in the art. The modes of administration include, but are not limited to, enteral (oral) administration, parenteral (intravenous, subcutaneous, and intramuscular) administration, topical application, and mucosal (nasal, respiratory, etc.) application.

The method of treatment according to this invention comprises administering internally or topically to a subject in need of treatment an effective amount of the desirable product. Doses of desirable products in the inventive method and pharmaceutical compositions containing same are an efficacious, nontoxic quantity generally selected from the range of 0.01 to 500 mg/kg of desirable product, preferably 0.1 to 50 mg/kg. Persons skilled in the art using routine clinical testing are able to determine optimum doses for the particular ailment being treated. The desired dose is generally administered to a subject from 1 to 6 or more times daily, intravenously, orally, rectally, parenterally, topically, or by inhalation. The efficacy of the desirable products of this invention can be determined by standard techniques known to one of ordinary skill in the art.

The preparation of products for administration in pharmaceutical preparations may be performed in a variety of methods well known to those skilled in the art. Appropriate pharmaceutically acceptable salts within the scope of the invention are those derived from mineral acids such as hydrochloric acid, hydrobromic acid, phosphoric acid, nitric acid, and sulfuric acid; and organic acids such as tartaric acid, fumaric acid, lactic acid, oxalic acid, ethylsulfonic acid, p-toluenesulfonic acid, and the like, giving the hydrochloride, sulfate, phosphate, nitrate, methanesulfonate, tartrate, benzenesulfonate, p-toluensulfonate, and the like, salt, respectively.

Desirable products of the invention may be formulated for parenteral administration in aqueous injection solutions which may contain antioxidants, buffers, bacteriostatic agents, solubilizing agents, chemoprotectants, etc. Extemporaneous injection solutions may be prepared from sterile pills, granules, or tablets which may contain diluents, dispersing and surface active agents, binders and lubricants which materials are all well known to the ordinary skilled artisan.

In the case of oral administration, fine powders or granules of the desirable product may be formulated with diluents and dispersing and surface active agents, and may be prepared in water or in a syrup, in capsules or cachets in the dry state or in a non-aqueous suspension, where a suspending agent may be included. The desirable products may also be administered in tablet form along with optional binders and lubricants, or in a suspension in water or syrup or an oil or in a water/oil emulsion or in a sustained release form from biodegradable or bioerodible polymers and may include flavoring, preserving, suspending, thickening, and emulsifying agents. The granules or tablets for oral administration may be coated or other pharmaceutically acceptable agents and formulation may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter. Liposomes can also be used a carriers for the products of the invention.

Additionally, the desirable products of this invention can find use as agricultural agents. Specifically, the desirable products can be herbicides, pesticides, growth regulators, etc. The use and administration of the products of the invention for agricultural purposes is known by one of ordinary skill in the art. The products of the invention can also be used in chemical manufacturing processes.

EXAMPLES

The following examples are illustrative of preferred embodiments of methods of preparation and products of the invention and are not to be construed as limiting the invention thereto.

Example One

Synthesis and Characterization of Nucleic Acid Test Mixtures Containing Modified Nucleosides Nucleic acid test mixtures containing natural or modified nucleosides were generated using T7 RNA polymerase to transcribe the modified RNA from a dsDNA template consisting of, for example, a 40 nt 5'-fixed region followed by either a 40 or 100 nucleotide randomized region and a 24 nucleotide 3'-fixed region. A template with a randomized region was used to (1) test the relative efficiency of synthesizing random pools of RNA, (2) generate random RNA templates for reverse transcription (RT) experiments, and (3) generate RNA to be characterized by its base composition. An example of a typical transcription is given below in Example Three. The transcription conditions include GMP to generate a 5'-monophosphate RNA, similar to the conditions used during the generation of RNA in typical SELEX™ experiments. After synthesis of the singly modified RNA libraries, the RNA is digested under basic conditions and the resulting nucleotides dephosphorylated with bacterial alkaline phosphatase. The resulting mixtures are then analyzed for their nucleoside composition using C18 reverse-phase HPLC.

The synthesis of various modified uridines and cytidines is described in U.S. Pat. No. 5,428,149, entitled "Method for Palladium Catalyzed Carbon-Carbon Coupling and Products"; U.S. patent application Ser. No. 08/264,029, filed Jun. 22, 1994, entitled "Novel Method of Preparation of Known and Novel 2'-Modified Nucleosides by Intramolecular Nucleophilic Displacement", now abandoned; U.S. patent application Ser. No. 08/347,600, filed Dec. 1, 1994, entitled "Purine Nucleoside Modifications by Palladium Catalyzed Methods", now U.S. Pat. No. 5,580,972; and U.S. patent application Ser. No. 08/458,421, filed Jun. 2, 1995, entitled "Palladium Catalyzed Nucleoside Modifications Methods Using Nucleophiles and Carbon Monoxide", now U.S. Pat. No. 5,719,273, all of which are herein incorporated by reference in their entirety. The synthesis of the triphosphates was accomplished by converting 5'-hydroxyl nucleosides to their triphosphates by a modified literature protocol (Ludwig and Eckstein, *J. Org. Chem.* (1989) 54, 631–635) followed by acidic Dowex deprotection, or by converting nucleoside 5'-monophosphates via a literature protocol (*J. Org. Chem.* (1990) 55, 1834). The triphosphates were purified via ion-exchange chromatography and/or reverse-phase HPLC with 0.05M triethylammonium bicarbonate buffer as the aqueous phase, and were characterized by their $^1$H and $^{31}$P NMR spectra and mass spectra. Solutions of the triphosphates were quantitated on the basis of their UV absorbance at their respective $\lambda_{max}$, as determined for the free nucleoside or the nucleoside 5'-monophosphate.

Some examples of modified pyrimidines which have been produced and converted to their triphosphates are shown below and include 5-benzoyl uridine (benzU), 5-pyridylmethyl uridine (pymeU), 5-ethylenediamine uridine carboxyamide (N-TFA-enU), 5-imidazole uridine carboxyamide (imidU), 5-pyridylmethyl cytidine monophosphate carboxyamide (pymeCMP), and 5-imidazole cytidine monophosphate carboxyamide (imidCMP).

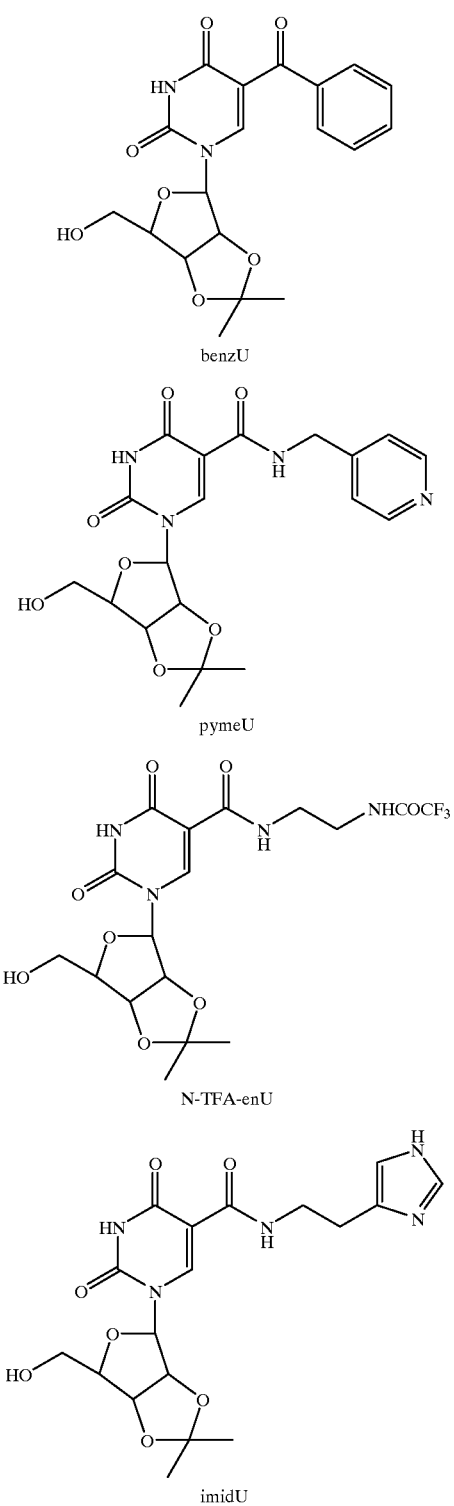

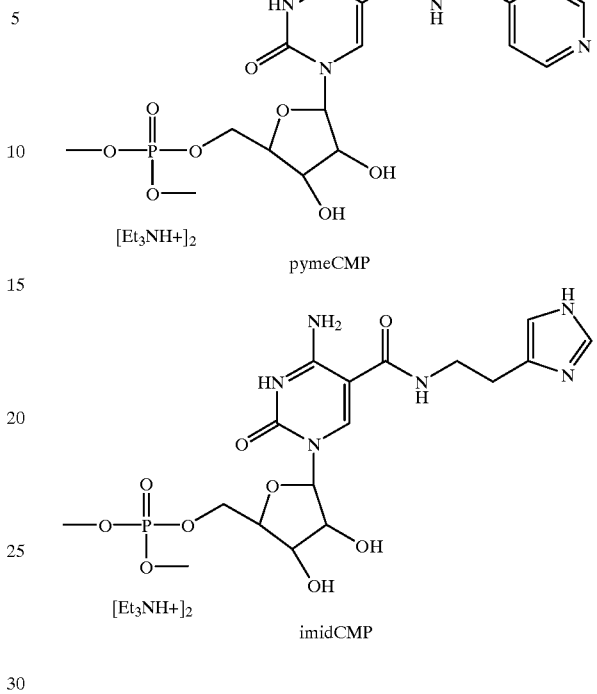

Example Two

Synthesis of Reactant-Linker Compounds

In one embodiment of the Parallel SELEX™ process the chemical reactant is attached to the nucleic acid test mixture via a linker group. This example demonstrates how to make several reactant-linker compounds by coupling the chemical reactant to a PEG molecule. Several chemical reactants have been linked to 2000 MW PEG by several techniques which employ PEG-2000 which has been converted to mono-amino PEG-2000 ("amino PEG"). Following are examples of PEG compounds linked with dienes (cyclic and acyclic), aliphatic ketones, aromatic ketones, β-ketoamides, alkynes (terminal and internal), as well as a biotin moiety. These PEG compounds have been subsequently converted to the corresponding phosphoramidites by standard methods. The reactant coupled to the protected PEG linker is then conjugated to the 5' end of a DNA 10-mer (to facilitate ligation with the random nucleic acid test mixture). This list is not intended to be inclusive of the chemical groups accessible to linkage to PEG compounds. The reactant-PEG-DNA moiety is then coupled to a nucleic acid test mixture, such as those described in Example One or in the SELEX™ patent applications. This coupling reaction is described in Example Three.

PEG-Acyclic Diene Synthesis

The following procedures were followed to prepare a PEG-acyclic, specifically 2,4-hexadienyl PEG2000 carbamate, as shown in the following scheme.

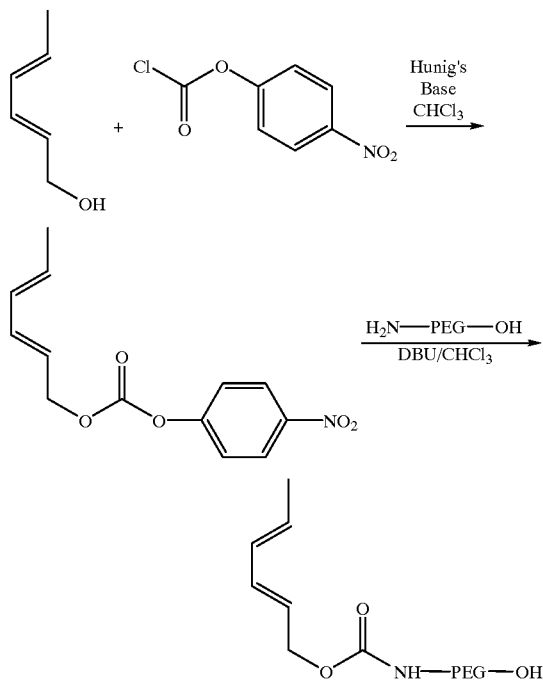

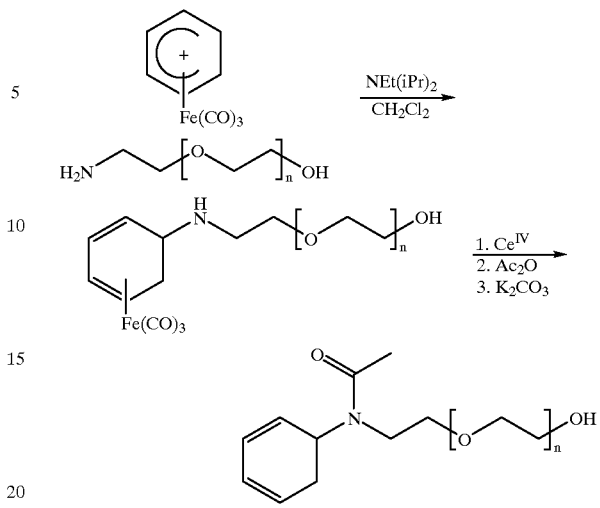

2,4-Hexadienyl-p-nitrophenyl carbonate was prepared as follows. Under an argon atmosphere, 1.0 mL (8.87 mmole) of 2,4-hexadien-1-ol and 2.0 mL (11.5 mmole) of anhydrous diisopropylethylamine were dissolved in 100 mL of $CHCl_3$ and cooled to 5° C. with an ice bath. To this mixture was added 1.97 g (9.76 nmoles) of p-nitrophenyl chloroformate dissolved in 10 mL $CHCl_3$ dropwise, over 30 min with stirring. The reaction mixture was stirred an additional 5 hr while being allowed to slowly come to room temperature. The mixture was then washed with 50 mL brine. The aqueous layer was back extracted with $CHCl_3$ (2×50 mL), the organic portions were combined and dried over $MgSO_4$ and the solvent removed under reduced pressure. The product was purified from the remaining yellow solid by recrystallization from ethanol to give 1.94 g (83%) of the carbonate as white needles. TLC: $R_f$=0.39 (hexanes). The compound was characterized on the basis of its $^1H$ and $^{13}C$ NMR spectra.

2,4-Hexadienyl PEG-2000 carbamate was prepared as follows. To a stirring solution of 500 mg (0.25 mmole) of PEG-2000 and 42 mg (0.275 mmole) of DBU in 30 mL $CHCl_3$ at room temperature was added 72 mg (0.275 mmole) of 2,4-Hexadienyl-p-nitrophenyl carbonate. The reaction was allowed to proceed overnight at room temperature with stirring. The solution was then washed with saturated $NaHCO_3$ (6×50 mL) and brine (1×50 mL). The chloroform phase was then dried over $MgSO_4$ and the solvent removed under reduced pressure to give a slightly yellow, waxy solid. The product was further purified by flash silica gel column chromatography (7% $MeOH/CH_2Cl_2$) which yielded 184 mg of a colorless solid. The identity of the desired product was confirmed by $^1H$ NMR.

PEG-Cyclic Diene Synthesis

The following procedures were followed to prepare a PEG-cyclic diene, specifically PEG-N-acetylcyclohexadiene, as shown in the following scheme.

PEG-cyclohexadiene iron tricarbonyl complex was prepared as follows. To a stirred solution of 250 mg (0.8 mmol) of cyclohexadienyliumiron(0)tricarbonyl tetrafluoroborate in 3 mL of anhydrous DMF at 0° C. was added a solution of 1.6 g (0.8 mmol) of amino PEG in 4 mL of anhydrous DMF. The solution was allowed to warm slowly to room temperature and concentrated in vacuo. The residue was suspended in 10 mL of THF and 200 mL of diethyl ether added to precipitate the product. The pale yellow solid obtained was collected by vacuum filtration to give 1.46 g (81% crude yield) of the product as confirmed by $^1H$ NMR spectroscopy.

PEG-cyclohexadiene was prepared as follows. To a stirred solution of 500 mg (0.22 mmol) of the PEG-cyclohexadiene iron complex in 4 mL of methanol was added 42 mg (0.22 mmol) of p-toluenesulfonic acid. The solution was cooled to −15° C. and 1 mL of $CH_2Cl_2$ was added to solubilize the reactants. Ceric ammonium nitrate (263 mg, 0.48 mmol) was then added as a solid and the solution stirred at −15° C. for 40 min. The solution was then allowed to warm to ambient temperature and concentrated in vacuo. The residue was dissolved in 150 mL of 2:1 brine:ethyl acetate, made basic with 100 mL of conc. aqueous $NaHCO_3$, and extracted with 4×50 mL of 20% $CH_2Cl_2$/ethyl acetate and the organic extracts concentrated in vacuo to give 369 mg (79% crude yield) of the product as confirmed by $^1H$ NMR spectroscopy.

PEG-diacetylcyclohexadiene was prepared as follows. To a stirred solution of 369 mg (0.17 mmol) of the above PEG-cyclohexadiene in 5 mL of anhydrous pyridine was added 35.3 μL (0.37 mmol) of acetic anhydride. The solution was stirred at ambient temperature overnight and an additional 16 μL of acetic anhydride was added. After 1 h the solution was concentrated in vacuo. The residue was dissolved in 120 mL of 2:1 brine:ethyl acetate and extracted with 4×50 mL of ethyl acetate, then 2×50 mL of 20% $CH_2Cl_2$/ethyl acetate, and the extracts combined and concentrated in vacuo to give 260 mg (61% crude yield) of the product as confirmed by $^1H$ NMR spectroscopy.

PEG-N-acetylcyclohexadiene was prepared as follows. To a stirred solution of 260 mg (0.12 mmol) of the diacetylated PEG-cyclohexadiene in 3 mL of methanol was added a solution of 163 mg (1.2 mmol) of $K_2CO_3$ in 1 mL of $H_2O$. The solution was stirred at ambient temperature overnight and concentrated in vacuo. The residue was dissolved in 60 mL of 2:1 brine:ethyl acetate and extracted with 2×40 mL of 20% $CH_2Cl_2$/ethyl acetate. The extracts were combined and concentrated in vacuo, the residue dissolved in 2 mL of THF, filtered through a plug of glass wool and 100 mL of diethyl ether added. The white solid obtained was collected by vacuum filtration and dried under high vacuum to give 119 mg (46% yield) of the product as confirmed by $^1$H NMR and mass spectrometry.

PEG-Ketone Synthesis

PEG-Acetophenone Synthesis

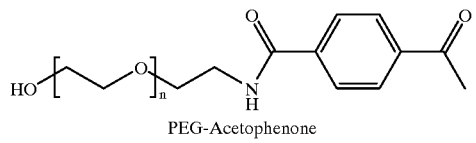

PEG-Acetophenone

PEG-Acetophenone was prepared as follows. Under an argon atmosphere, 2.0 g (1.0 mmole) of PEG-2000 was dissolved in dry THF and treated with 287 mg (1.1 mmole) of p-(N-hydroxysuccinimidyl)-carboxy acetophenone. The mixture was stirred at room temperature for two hours after which time the PEG was precipitated by addition of ether and isolated by filtration. The remaining white solid was purified by flash silica gel chromatography (7% MeOH/CH$_2$Cl$_2$) to yield 450 mg of the desired product as a waxy solid. Identity of the product was confirmed by $^1$H NMR.

PEG-Acetylacetamide Synthesis

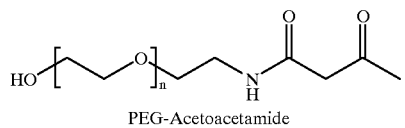

PEG-Acetoacetamide

PEG-Acetylacetamide was prepared as follows. To a stirred solution of 300 mg (0.18 mmol) of amino PEG in 2 mL of anhydrous DMF was added 36 mg (0.15 mmol) of N-hydroxysuccinimidyl acetoacetate. The solution was stirred at ambient temperature for 2 days and concentrated in vacuo. The residue was suspended in 5 mL of THF and 100 mL of diethyl ether added to precipitate the product. The white solid was collected by vacuum filtration to give 262 mg (70% yield) of the product as confirmed by $^1$H NMR.

PEG-4-Acetylbutyramide Synthesis

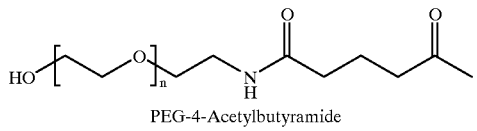

PEG-4-Acetylbutyramide

PEG-4-Acetylbutyramide was prepared as follows. To a stirred solution of 0.5ml (4.2 mmol) 4-acetylbutyric acid in 25 mL anhydrous CH$_2$Cl$_2$ was added 1.6 g (6.3 mmol) of the disuccinimidyl carbonate and 644 μL (4.6 mmol) of triethylamine. The solution stirred at ambient temperature overnight and concentrated in vacuo. The residue was purified by flash column chromatography on silica with 30% ethyl acetate/hexane to give 668 mg (70% yield) of the NHS ester as confirmed by $^1$H NMR spectroscopy.

To a stirred solution of 55 mg (0.24 mmol) of 4-acetylbutyric acid NHS ester in 3.0 mL of anhydrous DMF was added 400 mg (0.2 mmol) of amino PEG. The solution was stirred at ambient temperature overnight and concentrated in vacuo. The residue was dissolved in 10 mL of THF and 200 mL of diethyl ether added to precipitate the product. The white solid formed was collected by vacuum filtration and dried under high vacuum to give 334 mg (66% yield) of product as confirmed by $^1$H NMR.

PEG-Alkyne Synthesis

PEG-2-Butynamide Synthesis

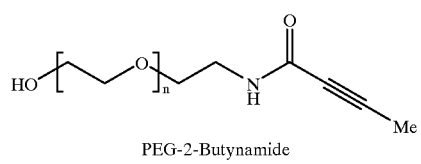

PEG-2-Butynamide

PEG-2-Butynamide was synthesized as follows. To a stirred solution of 250 mg (3.0 mmol) of 2-butynoic acid in 20 mL of anhydrous CH$_2$Cl$_2$ was added 619mg (3.0 mmol) 1,3-dicyclohexylcarbodiimide and 345 mg (3.0 mmol) of N-hydroxysuccinimide. The solution was stirred for 1.5 h, the solids removed by filtration and concentrated in vacuo. The residue was purified by flash column chromatography on silica with 40% ethyl acetate/hexane to give 448 mg (83% yield) of the NHS ester, as confirmed by its $^1$H NMR spectrum.

To a stirred solution of 300 mg (0.15 mmol) of amino PEG in 2 mL of anhydrous DMF was added 33 mg (0.18 mmol) of 2-butynoic acid NHS ester. The solution was stirred at ambient temperature overnight and concentrated in vacuo. The residue was suspended in 15 mL of THF and 200 mL of diethyl ether added to precipitate the product. The white solid formed was collected by vacuum filtration and dried under high vacuum to give 280 mg (75% yield) of the product as confirmed by $^1$H NMR.

PEG-4-Pentynamide Synthesis

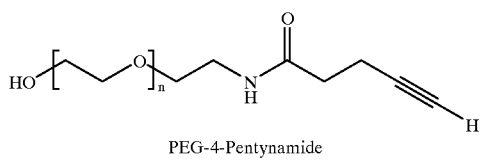

PEG-4-Pentynamide

PEG-4-Pentynamide was synthesized as follows. To a stirred solution of 250 mg (2.5 mmol) of 4-pentynoic acid in 20 mL of anhydrous CH$_2$Cl$_2$ was added 515 mg (2.5 mmol) of 1,3-dicyclohexylcarbodiimide and 288 mg (2.5 mmol) of N-hydroxysuccinimide. The solution was stirred overnight at ambient temperature, the solids were removed by filtration and the solution concentrated in vacuo. The residue was purified by flash chromatography on silica gel with 40% ethyl acetate/hexane to give 367 mg (75% yield) of the NHS ester as confirmed by $^1$H NMR spectroscopy.

To a stirred solution of 300 mg (0.15 mmol) of amino PEG in 2 mL of anhydrous DMF was added 35 mg (0.18 mmol) of 4-pentynoic acid NHS ester. The solution was stirred at ambient temperature overnight and concentrated in vacuo. The residue was suspended in 15 mL of THF and 200 mL of diethyl ether added to precipitate the product. The white solid formed was collected by vacuum filtration and dried under high vacuum to give 214 mg (57% yield) of the product as confirmed by $^1$H NMR.

PEG-Biotinamide Synthesis

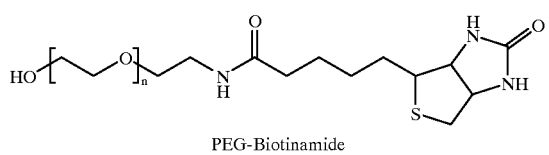

PEG-Biotinamide

PEG-Biotinamide was synthesized as follows. To a stirred solution of 400 mg (0.2 mmol) of amino PEG in 2 mL of anhydrous DMF was added 82 mg (0.24 mmol) of biotin NHS ester. The solution was stirred for 4 days at ambient temperature and concentrated in vacuo. The residue was suspended in 6 mL of THF and 150 mL of diethyl ether added to precipitate the product. The white solid formed was collected by vacuum filtration and dried under high vacuum to give 411 mg (92% yield) of the product as confirmed by $^1$H NMR.

Example Three
Preparing Nucleic Acid-Reactant Test Mixtures

Nucleic acid test mixtures were prepared as described in Example One and in the SELEX™ Patent Applications. Reactants are coupled to the nucleic acid test mixture either directly or through a linker moiety such as those described in Example Two. The preparation of the nucleic acid-reactant test mixture is accomplished as follows. The nucleic acid test mixture typically contains 100 or more nucleotides of contiguous random sequence flanked by defined 5' and 3' ends that permit primer hybridization. The double-stranded DNA (dsDNA) molecules, synthesized by Taq Polymerase, have a T7 RNA Polymerase promoter at the 5' end to facilitate transcription.

A typical transcription reaction contains 200 pmoles dsDNA, 80 μL 5× T7 RNA polymerase buffer (200 mM Tris-pH 8.0, 60 mM MgCl$_2$, 5 mM spermadine, 25 mM DTT, 20% glycerol and 0.01% triton X-100), 40 μL of 10 mM ATP, 40 μL 10 mM GTP, 40 μL 10 mM CTP, 40 μL 10 mM UTP (or modified UTP), 4 μL α[$^{32}$P] ATP (10 μCi/μL, if required), 32 μL 250 mM GMP, 5 μL RNasin (Promega, 40,000 Units/mL), 16 μL T7 RNA polymerase (New England Biolabs, 50,000 Units/mL) and dH$_2$O to a final volume of 400 μL. After incubating at 37° C. overnight, the RNA was purified on a 6% denaturing polyacrylamide gel. The 5' monophosphate is necessary for ligation of the RNA to the DNA portion of the linker sequence as described below.

Ligating the nucleic acid test mixture to DNA-PEG-reactant

A ligation reaction contains 500 pmoles nucleic acid test mixture, 1 nmole of DNA-PEG-reactant as described in Example Two, 1.5 nmoles of bridge oligo (5'-CTTGTCTCCCGCGTGCCTGG) (SEQ ID NO:3), 10 μL of 10× T4 DNA ligase buffer (Boehringer Mannheim, 660 mM Tris-HCl pH 7.5, 50 mM MgCl$_2$, 10 mM dithioerythritol, 10 mM ATP), 8 μL T4 DNA ligase storage buffer (Boehringer Mannheim, 20 mM Tris-HCl pH 7.5, 1 mM EDTA, 5 mM DTT, 60 mM KCl, 50% glycerol), 2 μL RNasin (Promega, 40,000 Units/mL), 8 μL T4 DNA ligase (Boehringer Mannheim, 5 Units/μL) and dH$_2$O to a final volume of 100 μL. All components of the ligation reaction except the RNasin and ligase were mixed and heated to 72° C. for 3 min. The solution was then slow cooled to room temperature (~10 min) and the RNasin and ligase added. After incubation at 37° C. overnight, the ligation product was purified on a 6% denaturing polyacrylamide gel. The resulting RNA-DNA-PEG-reactant is the nucleic acid-reactant test mixture.

Example Four
Use of Unmodified RNA to Facilitate a Diels-Alder Reaction Synthesizing a PEG linker A polyethylene glycol (PEG) linker was synthesized to act as a spacer between the nucleic acids (in this case 40N8 RNA) (SEQ ID NO:2) and the first reactant (in this case maleimide). The scheme for the synthesis of the linker is shown below.

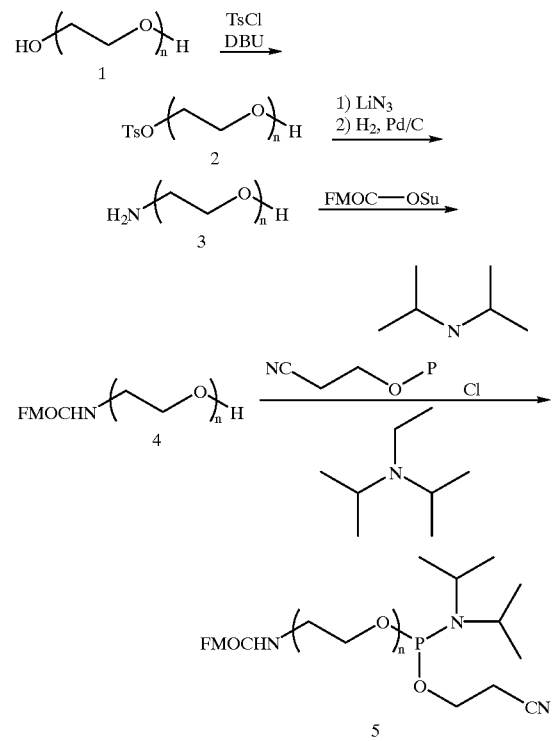

Synthesis of tosylated-PEG (Ts-PEG) (2)—Polyethylene glycol 1, 1.0 g (0.670 mmol, average molecular weight 1500) was dissolved in 15 mL of dry THF and the solvent removed in vacuo. To the remaining residue, dissolved in 15 mL of dry THF was added 52 mg (0.335 mmol) of DBU followed by 64 mg (0.335 mmol) of p-toluenesulfonyl chloride. The mixture was stirred under argon at room temperature for 10 days during which time a white precipitate formed. After 10 days the reaction mixture was filtered and the solvent was removed in vacuo. Purification of the monotosylated product by flash silica gel chromatography (7% MeOH/CH$_2$Cl$_2$) yielded 320 mg (58%) of a slightly yellow solid (R$_f$=0.31). The product was identified on the basis of its $^1$H NMR spectrum.

Synthesis of Amino-PEG (3)—In 2 mL of dry DMF was dissolved 400 mg (0.243 mmol) of Ts-PEG (2) followed by 119 mg (2.43 mmol) of lithium azide. With stirring and under an argon atmosphere the reaction mixture was heated to 80° C. for 5 hours. After coming to room temperature, the mixture was filtered through a silica pad, and the pad washed with 10% MeOH/CH$_2$Cl$_2$ until no product was detected in the eluent. The combined filtrate was evaporated to dryness under reduced pressure. The remaining residue was dissolved in 4 mL of MeOH to which was added 30 mg of 5% Pd/C and the solution was stirred under one atmosphere of hydrogen for 16 hours. The mixture was then filtered through celite. The celite pad was washed with MeOH, the filtrate combined and the solvent evaporated under reduced pressure to give an off-white solid. Purification by flash silica gel chromatography (12% MeOH.NH$_3$/CH$_2$Cl$_2$) yielded 279 mg (77%) of the desired amino-PEG product 3 (R$_f$=0.38, 15% MeOH.NH$_3$/CH$_2$Cl$_2$) as a white solid.

Synthesis of FMOC-PEG (4)—Amino-PEG (3) was dried by dissolving 840 mg (0.563 mmol) in 75 mL of dry THF followed by removal of the solvent by rotary evaporation. Under an argon atmosphere the amino-PEG was then dissolved in 50 mL dry THF, treated with 190 mg (0.563 mmol) of 9-fluorenylmethyl succinimidyl carbonate and the solution stirred at room temperature under argon for 2 hours. The solvent was then removed by rotary evaporation and the product purified by flash silica gel chromatography (8% MeOH/CH$_2$Cl$_2$) to give 863 mg (92%) of a white solid (R$_f$=0.28, 10% MeOH/CH$_2$Cl$_2$).

Synthesis of FMOC-PEG phosphoramidite (5)—Fmoc-PEG (4) was dried by dissolving 173 mg (0.104 mmol) in 25 mL of dry THF followed by removal of the solvent by rotary evaporation. Under an argon atmosphere, the FMOC-PEG was then dissolved in 25 mL of dry CH$_2$Cl$_2$, treated with 34.8 mL (0.208 mmol) of diisopropylethylamine followed by 36.2 mL (0.156 mmol) of 2-cyano N,N-diisopropylchlorophosphoramidite. The mixture was stirred for 1 hour at room temperature. The solvent and excess base was then removed under reduced pressure. The desired phosphoramidite product was purified by flash silica gel chromatography (8% MeOH/CH$_2$Cl$_2$) to yield 190 mg (97%) of a white solid (R$_f$=0.30, 10% MeOH/CH$_2$Cl$_2$).

DNA-PEG Conjugation and First Reactant Addition

The protected PEG linker synthesized above is then conjugated to the 5' end of a DNA 10-mer (to facilitate ligation with random RNA) followed by coupling of the first reactant (in this case maleimide) as shown in the scheme below.

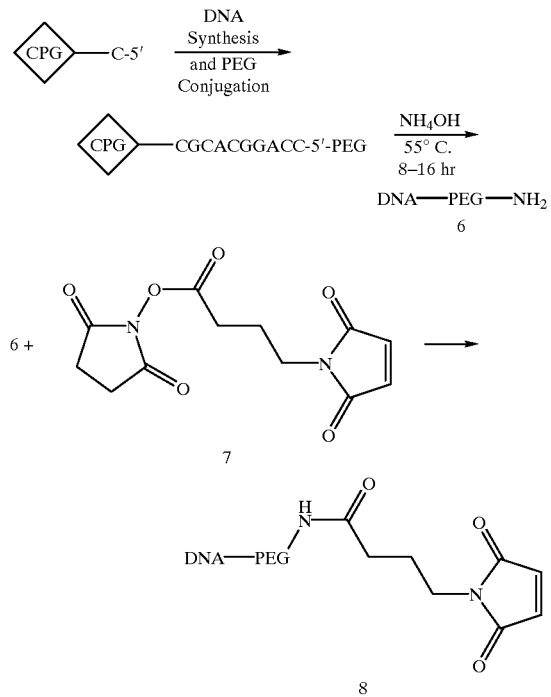

An applied Biosystems DNA synthesizer is used to synthesize the DNA 10-mer (5'-CCAGGCACGC) (SEQ ID NO. 1) and conjugate the FMOC-PEG phosphoramidite synthesized above in one procedure using standard phosphoramidite chemistries shown above. The DNA-PEG conjugate is cleaved from the CPG (controlled pore glass) solid phase support and fully deprotected using the standard overnight incubation in concentrated ammonium hydroxide to give the DNA-PEG free amine species 6. Any substrate can then be added to the end of the PEG chain using a variety of reactions. For example, a maleimide dienophile for a Diels-Alder reaction is appended by reacting the amino DNA-PEG with the maleimide-activated ester 7 to give the amide 8.

Producing Random RNA Pool having a 5' Monophosphate

A random sequence 40N8 RNA pool (SEQ ID NO. 2) was prepared using standard SELEX™ strategies and techniques from a synthetic, random sequence single-stranded DNA (ssDNA) template obtained from Operon (Alameda, Calif.). The random region was generated by utilizing a mixture of the four nucleotides (the molar ratios of which are adjusted to yield a 1:1:1:1 ratio of incorporated nucleotides) during oligonucleotide synthesis. The ssDNAs contained 40 nucleotides of contiguous random sequence flanked by defined 5' and 3' ends that permit primer hybridization. The double-stranded DNA (dsDNA) molecules, synthesized by Taq Polymerase, have a T7 RNA Polymerase promoter at the 5' end to facilitate transcription.

Each transcription reaction consisted of 100 pmoles of 40N8 dsDNA combined with 80 μl 5× T7 RNA Polymerase Buffer (200 mM Tris-pH 8.0, 60 mM MgCl$_2$, 5 mM Spermadine, 25 mM DTT, 20% Glycerol, 0.01% Triton-X-100), 40 μl 10 mM GTP, 40 μl 10 mM CTP, 40 μl 10 mM ATP, 40 μl 10 mM UTP, 40 μl 500 mM GMP, 8 μl RNasin (Promega, 40,000 Units/mL), 24 μl T7 RNA Polymerase (New England Biolabs, 50,000 Units/mL), and dH$_2$O to a final volume of 400 μl. After an overnight incubation at 37° C., the 5' monophosphate RNA was purified using a 8% denaturing polyacrylamide gel. The 5' monophosphate is necessary for ligation of the RNA to the DNA portion of the linker sequence as described below.

Ligating the Random RNA to DNA-PEG-maleimide

A random sequence RNA pool was generated as described above. A DNA 10-mer (SEQ ID NO. 1) and DNA bridge oligo (5'-CTTGTCTCCCGCGTGCCTGG) (SEQ ID NO. 3) used in the ligation reaction were obtained from Operon (Alameda, Calif.) and gel purified before use. One hundred pmoles of the random 40N8 RNA (SEQ ID NO. 2) was end-labeled by dephosphorylation with Bacterial Alkaline Phosphatase (Gibco BRL) and subsequent phosphorylation with T4 Polynucleotide Kinase (New England Biolabs) and γ-[$^{32}$P] ATP.

The ligation reaction contains 50 pmoles of random 40N8 RNA, approximately 60,000 CPM of random, 5'-end labeled 40N8 RNA, 100 pmoles DNA-PEG-Maleimide, 150 pmoles DNA bridge oligo, 2.5 μL 10× T4 DNA Ligase Buffer (50mM Tris-pH 7.8, 10 mM MgCl$_2$, 1 mM ATP, 25 mg/mL Bovine Serum Albumin), 0.5 μl RNasin (Promega, 40,000 Units/mL), T4 DNA Ligase to a final concentration of 1.2 Weiss Units/mL (New England Biolabs), and dH$_2$O to a final volume of 25 μl. The 1.2 Weiss Units/mL were obtained by converting New England Biolabs' unit definition to Weiss Units using the conversion factor found in any of their catalogs (1 NEB=0.015 Weiss Units).

All components except RNasin and T4 DNA Ligase were mixed, incubated at 70° C. for 3 minutes and slow-cooled to less than 37° C. RNasin and T4 DNA Ligase were then added, and the mixture was incubated for 90 minutes at 37° C. After incubation, RNA loading buffer was added and the mixture was heated to 70° C. for 3 minutes and then loaded onto a pre-heated 8% denaturing polyacrylamide gel. Ligation yields were obtained by autoradiography. The resulting RNA-DNA-PEG-maleimide is the nucleic acid-reactant test mixture.

Preparation of Biotinylated Diene Conjugate

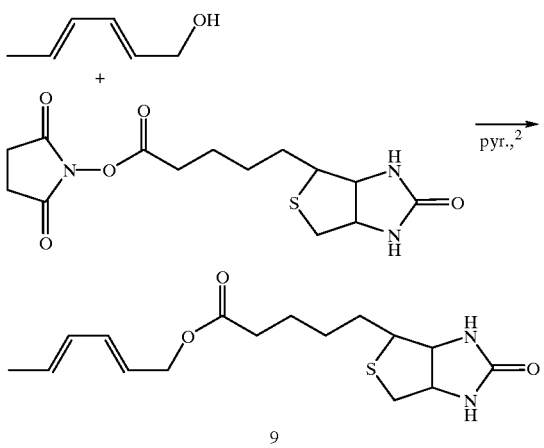

NHS-biotin (Pierce, 99.3 mg, 0.291 mmol) and 2,4-hexadien-1-ol (66.2 mg, 2.3 eq.) were combined in 10 mL of dry pyridine under argon at 0_ C. and stirred in the dark overnight while warming to ambient temperature. Monitoring of the reaction mixture by TLC (50% EtOAc/Hexanes) indicated slow reaction and the solution was then brought to reflux under argon overnight. Removal of the solvent in vacuo followed by successive chromatography on flash silica gel with 5% MeOH/EtOAc then 6% MeOH/$CH_2Cl_2$ afforded pure product 9, which was characterized on the basis of its $^1H$ and $^1H$-$^1H$ COSY NMR spectra.

The Chemical Reaction

The nucleic acid-reactant test mixture prepared above (RNA-DNA-PEG-maleimide) is reacted with the second reactant (biotinylated diene) under the following conditions. One–two nmol (~50,000 cpm) of nucleic acid-reactant test mixture is dissolved in 50 μL of reaction buffer (10 mM MES, 200 mM NaCl, pH 6.5), alternatively the reaction buffer can be (10 mM Tris, 300 mM NaCl, pH 7.0). The mixture is heated to 70° C. for 5 minutes. $MgCl_2$ is then added to a final concentration of 100 μM and 10 μM respectively and the solution is allowed to slowly come to room temperature (approximately 10 minutes). The biotinylated diene is then added to a final concentration of 1 mM, and at mixture is allowed to incubate at room temperature for 12 hours. The solution is then loaded on an immobilized streptavidin column and the column washed extensively with reaction buffer containing 10 μM $MgCl_2$. The bound RNA is liberated from the column matrix by treatment with proteinase K followed by washing the column with reaction buffer. Alternatively the RNA can be reverse transcribed while still bound to the resin or a disulfide linked biotin-diene substrate can be used in which case the RNA is eluted from the column using 50 mM DTT. Enrichment of the pool is followed by the number of cpm's eluted following standard proteinase K treatment. The eluted RNA is then reverse transcribed, the resulting cDNA PCR amplified, and the dsDNA transcribed as in typical SELEX™ experiments. The DNA-PEG-maleimide conjugate is ligated to the RNA as described above and the process repeated until the quantity of the resulting product is significant enough to determine the structure thereof.

Example Five
Use of Unmodified RNA and Metals in Solution to Facilitate a Diels-Alder Reaction The procedure followed for Example Four is repeated exactly, with the inclusion of the metal ions aluminum(III) and cobalt(II) in the reaction solution.

Example Six
Use of Modified RNA (Incorporating Pyridine-Modified UTP) to Facilitate a Diels-Alder Reaction The nucleic acids of this invention can be modified by various procedures described previously. One example of a modified nucleic acid is given where UTP molecules have been modified to incorporate a pyridine-type residue at the 5-position. The pyridine-modified UTP is incorporated into the random RNA described previously. The modified RNAs are attached to a reactant through a PEG linker and used to facilitate a Diels-Alder reaction.

The following procedure was followed to synthesize a uridine triphosphate (UTP) derivative that has a pyridine-type residue attached to the 5-position of the base.

Preparation of pyridyl carboxamide modified UTP

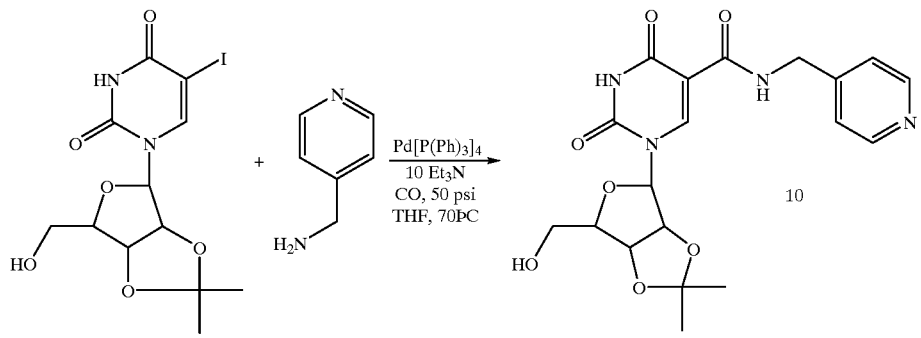

-continued

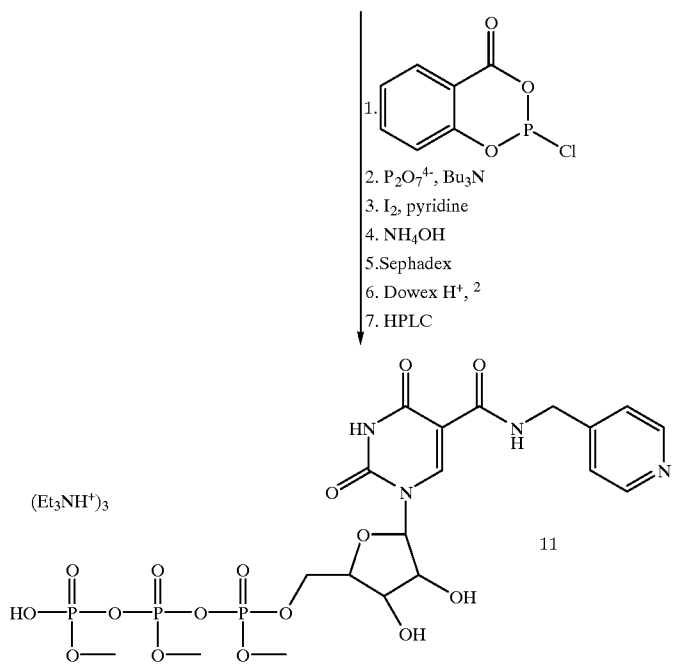

Carboxyamidation

A solution of 5-iodouridine-2',3'-isopropylidene (0.225 g, 0.545 mmol), Pd(PPh$_3$)$_4$ (0.1 eq., 56 mg), triethylamine (10 eq., 0.76 mL), and 4-(aminomethyl)-pyridine (4 eq., 0.2 mL) was prepared in 10 mL of dry THF under argon in a flame-dried glass bomb equipped with a teflon stopcock. The bomb was successively charged with 50 psi CO and evacuated three times, then pressurized to 50 psi CO and sealed. The flask was stirred vigorously while heating to 70° C. After 2 hrs., visible plating of the palladium had begun. The flask was stirred an additional 18 hrs., cooled and vented, and the solution evaporated to a yellowish oil. Chromatography on silica gel with 8–10% MeOH/CH$_2$Cl$_2$ gradient elution afforded 0.177 g (78%) of 10 as a white solid. Characterized by its $^1$H, $^{13}$C NMR spectra. Analytical samples could be obtained by recrystallization from methanol.

Triphosphate preparation

The triphosphate was prepared by the procedure of Ludwig and Eckstein (*J. Org. Chem.* 1989, 54, 631–635) using the 5'-hydroxyl modified uridine prepared above. The triphosphate was purified by passage of the reaction mixture in distilled water through an anion exchange column (Sephadex DEAE) with 0.05–1.00 M TBK (triethyl ammonium bicarbonate) buffer solution. Lyophilization of the fractions which contained the triphosphate gave the isopropylidene-protected triphosphate, which was characterized by its $^{31}$P NMR spectrum. The isopropylidene protecting group was removed by heating the triphosphate in 5 mL of distilled water with 100 mg of Dowex 50WX8 resin (H$^+$ form) for 15 min. at 70° C., followed by neutralization with 2 M TBK buffer (to pH 8). Final purification of this solution was performed by reverse phase preparatory HPLC (C18 column) with 3–5% gradient of CH$_3$CN in 0.05 M TBK buffer. The triphosphate thus prepared (11) was characterized on the basis of its $^1$H and $^{31}$P NMR spectra as the tris(triethylammonium) salt form and quantitated by UV absorbance (277 nm, $\epsilon$=14,600 M$^{-1}$ cm$^{-1}$).

The reaction is continued as described in Example 4 above.

Example Seven

Use of Modified RNA (Incorporating Histidinol-Modified UTP) to Facilitate the Cleavage of GRP The nucleic acids of this invention can be modified by various procedures described previously. One example of a modified nucleic acid is given where UTP molecules have been modified to incorporate a histidine-type residue at the 5-position. The histidine-modified UTP is incorporated into the random RNA (SEQ ID NO. 2) described previously. The modified RNAs are attached to a reactant through a PEG linker and used to facilitate the cleavage of Gastrin Releasing Peptide (GRP).

Synthesizing histidine-modified UTP

The following procedure was followed to synthesize uridine triphosphate (UTP) molecules that have a histidine-type residue attached to the 5-position.

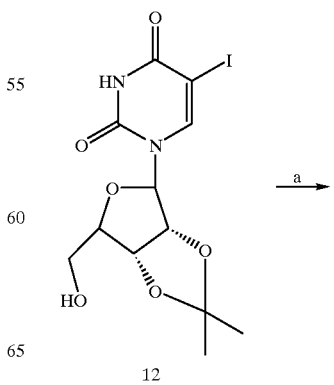

hexane, 200 mL CH₂Cl₂ and the product eluted with 5% CH₃OH/CH₂Cl₂. This eluent was concentrated and flash chromatographed on silica gel with 5% CH₃OH/CH₂Cl₂ to yield 0.294 g of 13 as a white solid.

Histidinol Michael addition adduct

TBDMS protected histidinol 14—To a stirred solution of 205 mg (5.1 mmol) of NaH washed 3× with hexane, under argon, in 3.0 mL DMF was added in portions 500 mg (2.3 mmol) of N-methylhistidinol dihydrochloride, resulting in moderate gas evolution. The solution was stirred for 1.5 h, then 1.8 mL (23 mmol) of anhydrous pyridine and 693.0 mg (4.6 mmol) of TBDMSC1 was added. The solution was stirred for 1.5 h, concentrated in vacuo and flash chromatographed on silica with 15% CH₃OH.NH₃/CH₂Cl₂ to yield 14.

Michael adduct 15—To a stirred solution of 167.9 mg (0.6 mmol) 13 in 10 mL of anhydrous DMF was added 0.105 mL (0.6 mmol) of diisopropylethylamine, then dropwise a solution of 185 mg (0.72 mmol) of 14 in 1.85 mL of anhydrous DMF. The solution was stirred for 1 h, concentrated in vacuo and flash chromatographed on silica gel with 15% CH₃OH.NH₃/ethyl acetate to yield 90.0 mg of 15 as a white solid, characterized on the basis of its $^1H$ NMR spectrum.

Triphosphate preparation

To a solution of 15 in dioxane/pyridine was added dropwise a solution of 2-chloro-4H-1,2,3-benzedioxaphosphorin-4-one in THF and the solution stirred for 20 min., then a 0.5 M solution of bis(tributylammonium) pyrophosphate in DMF and tributylamine were added simultaneously. The solution was stirred for an additional 20 min. and a pyridine/water solution of 12 added and the solution stirred for 20 min. Excess iodine was destroyed with 5% sodium bisulfite, stirred for 15 min., the solution concentrated, and hydrolyzed with concentrated ammonium hydroxide. The ammonia was removed in vacuo, the remaining solution washed twice with CH₂Cl₂, once with ethyl acetate and concentrated in vacuo. The residue was dissolved in water and stirred with Dowex resin for 15 min. at 70° C. The solution was filtered, neutralized with 2 M TBK buffer, loaded directly onto DEAE Sephadex and eluted with a gradient of 0.05 M triethylammonium bicarbonate buffer (TBK buffer) to 1.0 M TBK buffer to yield product slightly contaminated with a salicylate species and a small amount with the TBDMS and isopropylidene protecting groups still intact. The material was again treated with Dowex resin and purified on a reverse phase HPLC C18 column with a gradient of 0–5% acetonitrile in 0.05 M TBK buffer over 15 min. to yield pure 16 by $^1H$, $^{13}C$ and $^{31}P$ NMR.

The experiment is continued as outlined in Example 4 above, however, rather than forming a cyclohexene product, the nucleic acid hydrolyzes the GRP protein.

Example Eight

5'-Phosphorothioate-Modified RNA Binding to N-Bromoacetyl-Bradykinin

This example describes a Parallel-SELEX™ procedure wherein the coupled reactant is 5' guanosine monophosphorothioate (GMPS) directly attached to a random nucleic acid test mixture. The free reactant is a bromoacetyl group attached to the bradykinin target (BrBK). This example describes the selection and analysis of a 5' guanosine monophosphorothioate-substituted RNA (GMPS-RNA) which specifically reacts with N-bromoacetylated-bradykinin (BrBK) and facilitates the formation of a thio-ether bond between the RNA and the BrBK peptide. Previous work in this area showed that it was difficult to obtain ligands to bradykinin both in free solution and conjugated to a support matrix. As will be described below, RNA showing Into a self-contained coupling apparatus, equipped with a pressure-equalizing addition funnel, in an inert atmosphere glove box was weighed 702.3 mg (2.0 mmol) 12, 44.9 mg (0.20 mmol) palladium acetate, 114.3 mg (0.60 mmol) copper(I)iodide, and 157.4 mg (0.60 mmol) triphenylphosphine. The apparatus was sealed, removed from the box, and 30 mL of anhydrous THF added to the round bottom portion of the apparatus via cannula. To the addition funnel portion was added via cannula an argon-purged solution of 0.643 mL (2.2 mmol) vinyltributyltin in 40 mL of anhydrous THF. The flask was successively evacuated and charged three times with CO, then heated at 70° C. for 1.0 h until the yellow solution became slightly orange. The vinyltributyltin solution was then added at a rate of 1 drop per 10 sec. The solution turned dark red after 5–10% of reagent addition. The solution was heated at 70° C. for 5 h, allowed to cool and concentrated in vacuo. The residue was dissolved in CH₂Cl₂, loaded onto a pad of silica, washed with 200 mL a 6700-fold increase in $k_{cat}/K_m$ and a 100-fold increase in binding affinity for N-bromoacetyl-bradykinin relative to the starting pool was identified. This RNA binds its substrate with high specificity, requiring both the amino- and carboxy-terminal arginine residues of the peptide for optimal activity.

A. The Parallel-SELEX™

The Parallel-SELEX™ reaction was carried out using 5' guanosine monophosphorothioate (GMPS) as the coupled reactant attached to an RNA test mixture and bromoacetylated bradykinin (BrBK) as both the free reactant and target. GMPS-RNA is selected for the ability to rapidly substitute the thioate group of the RNA for the bromide group of BrBK. The product, BK-S-RNA, is then partitioned subtractively from the remaining unreacted GMPS-RNA and re-amplified prior to continuing with another selection cycle.

1. GMPS-RNA

The Parallel-SELEX™ was performed with an initial random repertoire of approximately 5×10$^{13}$ GMPS-RNA molecules of length 76 nucleotides having a central region of 30 randomized nucleotides (30N1) (SEQ ID NO: 4), described in detail by Schneider et al., (FASEB, 7, 201 (1993)), with the non-random regions serving as templates for amplification. The nucleic acid reactant test mixture was formed by inclusion of GMPS in the initial and all subsequent transcription reactions such that it was preferentially utilized over equimolar GTP in the priming of transcription by T7 RNA polymerase such that approximately 80% of the full length product was initiated by GMPS. GMPS-RNA was transcribed and purified by Amicon Microcon-50 spin separation to remove excess GMPS. GMPS-RNA is purified away from non-GMPS RNA using Thiopropyl Sepharose 6B, eluted from the matrix with dithiothreitol (DTT) and purified from the DTT with another Microcon-50 spin separation. Thiopropyl sepharose 6B (Pharmacia) was pre-washed in column buffer (500 mM NaCl, 20 mM HEPES pH 7.0) and then spun dry at 12,000 g prior to use. For GMPS-RNA purification, Microcon-50 column-purified RNA was brought to a final concentration of 500 mM NaCl, 10 mM EDTA and 20 mM HEPES pH 7.0 and added to matrix at a measure of 25 µL per 60 µL void volume. The mix was then reacted at 70° C. for 5 minutes, spun at 12,000 g, spin-washed with four column volumes of 90% formamide, 50 mM MES pH 5.0 at 70° C., spin-washed with four column volumes of 500 mM NaCl in 50 mM MES, pH 5.0 and spin-eluted with four column volumes of 100 mM DTT in 50 mM MES, pH 5.0. These conditions were optimized for the retention and subsequent elution of only GMPS-RNA.

2. Bromoacetylated bradykinin

Bromoacetylated bradykinin (BrBK) was used as both the free reactant and target in this example. The bromoacetyl group is the free reactant. BrBK was synthesized by reacting 50 µL of 5 mM bradykinin with three successive 250 µL portions of 42 mM bromoacetic acid N-hydroxysuccinimide ester at 12 minute intervals at room temperature. Excess bromoacetic acid N-hydroxysuccinimide ester was removed by filtration over 5 mL of aminoethyl acrylamide (five minutes of reaction at room temperature), followed by separation of the BrBK over GS-10 Sepharose. BrBK concentration was determined at 220 nm using an absorption coefficient of 12,000 cm$^{-1}$M$^{-1}$.

3. The selection reaction

Those species of GMPS-RNA which are most capable of carrying out the reaction with BrBK are selected iteratively through multiple rounds of SELEX™. Rounds of selection were carried out in reaction buffer with 1.1 mM BrBK and with the GMPS-RNA concentrations for the given times and temperatures indicated in Table 1 as follows.

TABLE 1

| Temp. (° C.) | 37 | 30 | 30 | 24 | 24 | 20 | 0 | 0 | 0 | 0 | 0 | 0 |
|---|---|---|---|---|---|---|---|---|---|---|---|---|
| Reaction time (s) | 60 | 60 | 30 | 60 | 30 | 30 | 60 | 60 | 120 | 60 | 30 | 60 |
| [RNA] (µM) | 40 | 40 | 40 | 40 | 40 | 40 | 20 | 20 | 20 | 20 | 20 | 20 |
| % RNA reacted | 1.3 | 0.7 | 0.8 | 0.7 | 1.9 | 2.5 | 1.2 | 3.4 | 4.5 | 5.0 | 2.5 | 2.8 |
| Background ratio | 3.2 | 3.2 | 3.4 | 1.7 | 2.5 | 3.9 | 3.1 | 4.0 | 4.9 | 10.1 | 9.0 | 4.5 |

During the selection, the BrBK peptide concentration was kept at 1.1 mM, a concentration 12-fold lower than the $K_m$ of the round 0 pool with BrBK. Proceeding through the selection, reaction time was restricted and temperature of the reaction was decreased in order to limit the reaction to 5% or less of the total GMPS-RNA. The object was to maintain second-order reaction conditions in order to select for improvements in both binding and chemistry. Activity of the BrBK was assayed at 12.5 µM BrBK with 25 µM GMPS-RNA; when the reaction was carried out to completion, 50% of the RNA was covalently bound by BrBK indicating that bromoacetylation of the peptide was essentially complete.

Reactions were quenched with a final concentration of either 235 mM sodium thiophosphate (rounds 1–8) or sodium thiosulfate (rounds 9–12) and subtractively partitioned either on denaturing 7 M urea 8% polyacrylamide APM gels (rounds 1–6) or by affinity chromatography (rounds 7–12). % RNA reacted refers to the percent of the total GMPS-RNA present as BK-S-RNA from acrylamide gel partitioning or as freely eluting BK-S-RNA in affinity column partitioning. Background was subtracted from the recovered RNA in both of these cases; background refers to the amount of RNA recovered from a control treatment where the reaction was quenched prior to the addition of the BrBK. The background ratio is the ratio of reacted RNA to that present as background. An attempt was made to keep this ratio between 2 and 10 throughout the rounds of SELEX™ by adjusting the reaction time.

The subtractive partitioning was accomplished either by subtraction of the GMPS-RNA upon Thiopropyl Sepharose 6B, or by separation of the two species on an APM polyacrylamide gel. [(B-Acryloylamino)phenyl]mercuric Chloride (APM) was synthesized and used at a concentration of 25 µM in denaturing polyacrylamide gel electrophoresis for the retardation of thiol-containing RNA as reported by G. L. Igloi, Biochemistry 27, 3842 (1988). GMPS-RNA was purified from APM-polyacrylamide by elution in the presence of 100 mM DTT. In concurrence with the cited literature, it was found that freshly purified, APM-retarded GMPS-RNA when re-run on an APM gel gave a free band of non-retarded RNA consisting of approximately three percent of the total GMPS-RNA applied. Free-running RNA was problematic in that it ran very closely to BK-RNA (regardless of the percent acrylamide used in the gel) and thus increased the background during partitioning. When this free-running RNA was purified from the gel and rerun on an APM gel, approximately 50% of this RNA remained free-running, with the balance of RNA running as GMPS-RNA. The amount of free-running RNA was proportional to the amount of time spent during precipitation, but was not dependent on the effect of pH, the presence or absence of either DTT, magnesium acetate, formamide, urea, or heat.

Reverse transcription and polymerase chain reaction were carried out as reported by Schneider et al., (FASEB, 7, 201 (1993)). The $k_{obs}$ value of the GMPS-RNA pool increased 100-fold between rounds 4 and 6, increasing only 2-fold with further rounds. Reactions to determine $k_{obs}$ values were carried out at 0° C. in reaction buffer (50 mM HEPES, pH 7.0, 5 mM $MgCl_2$, 150 mM NaCl) at 2 μM GMPS-RNA and 130 μM BrBK, with monitoring at 0, 1, 3, 10, 30, and 90 minutes. GMPS-RNA was denatured at 70° C. for 3 minutes and allowed to slow cool at room temperature prior to dilution to final reaction buffer conditions, transfer to ice, and addition of BrBK. Reactions were quenched on ice with 235 mM sodium thiosulfate and run on a denaturing 7 M urea 8% polyacrylamide APM gel. $k_{obs}$ values were determined as the negative slope of the linear range of data points from plots relating the concentration of unreacted GMPS-RNA vs. time. Round 10 and round 12 pools were used for cloning and sequencing.

B. The Clones

Fifty six independent clones were sequenced. Sixteen reactants were compared with the 30N1 bulk pool for reactivity with BrBK; all tested reactants show a 10- to 100-fold increase in $k_{obs}$ relative to the original pool. Reactant 12.1 (SEQ ID NO:5) was chosen for further kinetic analysis based on three criteria: (i) in a preliminary study of reaction inhibition with competing bradykinin it had the lowest $K_i$ for bradykinin (data not shown); (ii) it was the most frequently represented molecule in the round 12 population; and (iii), it had the second fastest $k_{obs}$ of the reactants tested.

The selected increase in $k_{obs}$ of reactant 12.1 is attributable to increases in both reactivity and binding. In reaction with BrBK, reactant 12.1 shows a 67-fold increase in $k_{cat}$ over that of bulk 30N1 GMPS-RNA, with a 100-fold reduction in $K_m$, giving an overall 6700-fold increase in $k_{cat}/K_m$ (see Table 1).

C. Specificity

Structural elements of BrBK required for optimal binding by reactant 12.1 were studied through inhibition of the reaction by bradykinin analogs. While inhibition by BK is not measurable in the reaction of bulk 30N1 GMPS-RNA with BrBK (data not shown), native bradykinin (BK) has a $K_i$ of 140±60 μM for the reaction between reactant 12.1 and BrBK. This value is nearly identical to the $K_m$ of the uninhibited reaction. Des-Arg$^9$-BK (a BK analog lacking the carboxyl terminal arginine) has a $K_i$ of 2.6±0.5 mM. Thus, the lack of the carboxy terminal arginine decreases the binding between BK and reactant 12.1 approximately 18-fold. Furthermore, des-Arg$^1$-BK (a BK analog lacking the amino terminal arginine) does not show any measurable inhibition of the reaction between reactant 12.1 and BrBK, indicating that the amino-terminal arginine is absolutely required for the observed binding between reactant 12.1 and BrBK. Recognition of arginine must be in the context of the peptide, however, since free L-arginine alone does not measurably inhibit the reaction. Thus, the increase in affinity of reactant 12.1 over that of the bulk 30N1 GMPS-RNA for BrBK is in part attributable to reactant recognition of the amino terminal arginine of BrBK, and to a lesser extent the carboxy terminal arginine. The intrinsic reaction activity of reactant 12.1 was studied using N-bromoacetamide ($BrAcNH_2$) as a minimal bromoacetyl structure. The $K_m$ and $k_{cat}$ values in the reactions of reactant 12.1 and the 30N1 RNA pool with $BrAcNH_2$ are approximately the same. Therefore, the enhanced reaction rate of reactant 12.1 with BrBK is apparently due not to increased nucleophilicity of the thioate group, but is rather a result of steric and/or entropic factors in the positioning of the two substrates. Thus a chemical reaction has been facilitated, exactly as is required for The Parallel SELEX™ process.

Example Nine

Use of Unmodified RNA and Imidazole-UMP-Modified RNAs to Facilitate a Claisen Condensation This example describes a Parallel SELEX™ procedure wherein the coupled reactant is an acetophenone attached via a PEG linker to a random nucleic acid test mixture. The nucleic acid test mixture included 100 nucleotides of random sequences which are unmodified or contain imidazole-UTP. Preparation of the acetophenone reactant-nucleic acid test mixture is described in Examples 1–3. The free reactant is a biotin-4-nitrophenol molecule. The reaction facilitated by the RNA is a Claisen reaction between the acetophenone and the nitrophenol moiety as shown in the scheme below.

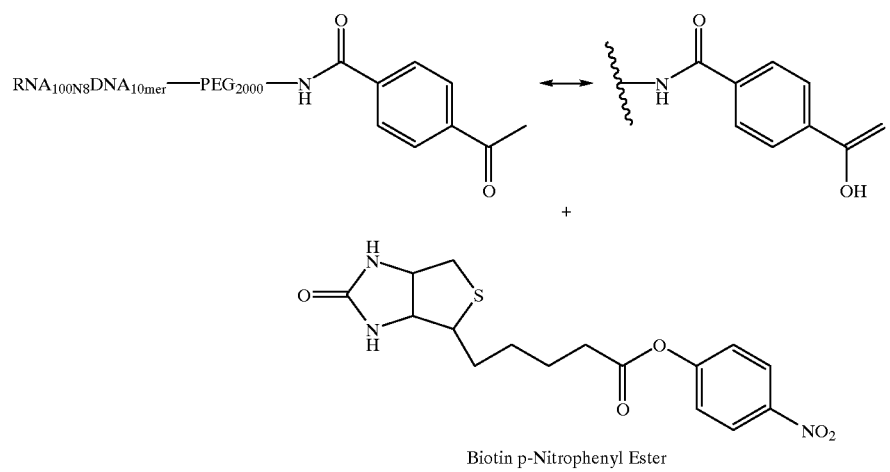

Biotin p-Nitrophenyl Ester

-continued

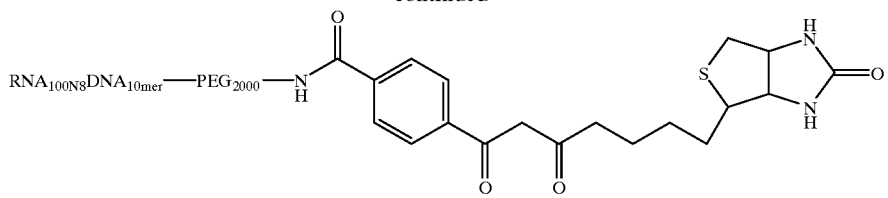

Single-stranded DNA templates for PCR and transcription of RNAs

A 147-nucleotide 100N8 single-stranded DNA (ssDNA) oligonucleotide with a 100-nucleotide region of contiguous random sequence and 5' and 3' fixed regions (SEQ ID NO: 6) was synthesized by standard methods. The 100N8C (SEQ ID NO: 7) ssDNA template was identical to the 100N8 template except that the 8 nucleotides flanking the random region in the 3'-fixed region were made complementary to the 8 nucleotides flanking the random region in the 5'-fixed region. The complementary 8 nucleotides of 100N8C are provided to form a stem structure in the RNA with a 100N loop in the variable region. 100N8C therefore has initial structure.

Producing single-copy double-stranded PCR product 2 nmole single-copy ssDNA templates for both 100N8 and 100N8C were used in a PCR reaction for 2 cycles of amplification to create 2 nmole transcribable product. The single-copy double-stranded PCR products were purified on a Qiagen column for transcription. One nmole of each 100N8 and 100N8C template was used for transcription with unmodified RNA and one nmole of each template was used for transcription with 5-imidazole-UTP. The RNA transcripts were purified, ligated, and gel purified as described below.

Producing Random RNA Pool having a 5' Monophosphate

RNA transcripts were prepared by transcription of double-stranded PCR products in a 500 μl reaction mixture containing 40 mM Tris-Cl, 12 mM $MgCl_2$, 1 mM spermidine, 1 mM each ATP, CTP, UTP or 5-imidazole-UTP, 20 mM GMP, 0.26 μM α-$^{32}$P-ATP, 5 mM DTT, 4% PEG, 0.002% Triton X-100, pH 8.0. The concentration of RNA varied from 125 nM to 1 μM, lower concentrations giving higher amplification. T7 RNA polymerase was added to 1.5 μM and the transcription was incubated for 2 hrs at 37° C. The reaction mixture was extracted 1× each with an equal volume phenol, phenol:chloroform (50:50), and chloroform. Following extraction, the RNA was applied to a Centrex UF-0.5 30,000 MW filter. The RNA was washed 3× with 500 μl $H_2O$. The RNAs were eluted from each filter in 200 μl $H_2O$. The RNAs were quantitated.

Ligating the Random RNAs to DNA-PEG-acetophenone

RNAs were ligated to the acetophenone-PEG-10-nucleotide DNA in 500 μl aliquots at a concentration of 5 μM RNA. The ligation reaction was set up in two steps. In the first step, the RNA was incubated with a 2-fold excess of the acetophenone-PEG-10-nucleotide DNA and a 3-fold excess of the 20-nucleotide bridge DNA in a 330 μl mixture containing 66 mM Tris-Cl, 5 mM $MgCl_2$, 1 mM DTE, 1 mM ATP, pH 7.5 (1× Boehringer Mannheim ligase buffer) at 72° C. for 3 min. In the second step, after the reaction mixture reached room temp, 40 μl Boehringer Mannheim enzyme storage buffer (20 mM Tris-Cl, 60 mM KCl, 1 mM EDTA, 5 mM DTE, 50% glycerol, pH 7.5), 53 μl $H_2O$, 17 μl RNAsin (Promega, 40 units/μl), 17 μl 1× ligase buffer (above) and 40 μl ligase (Boehringer-Mannheim, 5 units/μl) were added to a final volume of 500 μl. The ligation reaction was placed in a 37° C. incubator for 2–3 hrs. The ligated RNA was run on two 1.5 mm 6% denaturing polyacrylamide gels. The ligated RNA was cut from the gel, freeze-squeezed through a 0.2 μM filter, passed over NAP-5 desalting columns, and dried in a speed vac. The dried ligated RNA was resuspended in 50 μl water and quantitated.

The Chemical Reaction

The reactions of the nucleic acid-reactant test mixtures (acetophenone-PEG-DNA-RNA) with second reactant (biotin-4-nitrophenol) were in 500 μl aliquots containing 50 mM Hepes, 200 mM NaCl, 200 mM KCl, 2 mM $MgCl_2$, 2 mM $CaCl_2$, 10 μM $ZnCl_2$, 20% acetonitrile, pH 7.0. The concentration of the ligated RNA in the reactions were 2.5 μM and the concentration of the biotin-4-nitrophenol compound was 0.5 mM. The concentrations of the nucleic acid-reactant and second reactant were adjusted as necessary to increase stringency. The reaction mixtures were incubated for 17 hrs at 25° C. Following the incubation, the reaction mixtures were passed first through a NAP-5 column and then through a NAP-10 column to remove free biotin-4-nitrophenol compound. These samples were dried in a speed vac then suspended in 100 μl water. The specific activities of these samples were determined. The reacted product is partitioned as described below, reverse transcribed, PCR amplified, and transcribed. The Acetophenone-PEG-$DNA_{10mer}$ conjugate is ligated to the RNA as described above and the selection/amplification is repeated until the test mixture pool is sufficiently enriched with facilitating RNAs to determine the structure of their attached reaction products.

Gel-shift Partitioning

Rounds 1–3

Streptavidin (10 nmoles) and 10× buffer (to give a solution containing 10 mM Tris, 150 mM NaCl, pH 7.5) were added and each sample was incubated 15 min at 37° C. followed by a 3 min incubation at 70° C. As a positive control for streptavidin induced gel shift of a biotinylated RNA, biotin-PEG-$DNA_{10}$-$RNA_{100N}$ (approximately 7 pmoles) prepared similarly to the acetophenone-PEG-$DNA_{10}$-$RNA_{100N}$ above, was incubated with 10 nmoles of streptavidin as described above. The streptavidin shifted samples were run on a 1.5 mm 6% denaturing gel at 50 watts in an insulated gel apparatus until the xylene cyanol indicator dye was approximately 1 inch from the bottom.

The gel bands at the shifted region were excised as predicted by the positive control. The RNA was freeze-squeezed from the gel and passed through a NAP-5 column and dried in the speed vac. The RNAs were resuspended in 50 μl water. The quantity of recovered RNA was determined by determining the counts recovered and using the specific activity of the RNA applied to the gel. The RNA is reverse transcribed and the resulting DNA is PCR-amplified. PCR products are then transcribed and the RNA transcripts are ligated to the acetophenone-PEG-$DNA_{10mer}$ as described above.

Partitioning with Streptavidin-coated magnetic beads (DYNAL)

Rounds 4–6

50 µl of a paramagnetic bead slurry (should bind up to 100 pmoles of biotinylated oligonucleotide) in a 1.5 ml Eppendorf tube is placed in an MPC apparatus (magnetic holder) and the supernatant is removed. Beads are washed 3×, by placing tube in MPC between each wash, with Binding and Washing (B&W) Buffer containing 10 mM Tris, pH 7.5, 1 mM EDTA, 2.0 M NaCl, 0.5% PEG 2000. B&W Buffer is prepared with DEPC-treated water. For the binding reaction, beads are resuspended in 100 µl B&W buffer. RNA is added in a volume of 100 µl DEPC-treated water for a total volume of 200 µl. RNA is incubated with beads for 30 min, with occasional mixing. The tube is placed in the MPC holder and the buffer is removed and saved as #1. The beads are washed 2× with 200 µl B&W, placing in the MPC holder between washes. The wash buffers are saved as #2 and #3. The beads are then washed with 200 µl water, followed by a 100 µl water wash. The water washes are saved and pooled as #4. The beads are resuspended in 50 µl water and saved as #5. After round 6, an additional 200 µl wash with water was included. The wash buffers are each added to a vial of 4 ml scintillation fluid. An aliquot of the magnetic beads is also counted. These numbers are used to determine % bound. The background in this experiment, determined by incubating the nucleic acid-reactant test mixture (acetophenone-PEG-DNA-RNA) in the reaction without the second reactant (biotin-4-nitrophenol), is less than 0.02%. The RNA attached to the beads is reverse transcribed. The cDNA is removed from the beads using thermal denaturation conditions and the MPC holder and PCR amplified.

Counter SELEX™ Methods

To eliminate potential undesirable products resulting from the reaction of the second reactant (biotin-4-nitrophenol) with ordinary functional groups of the nucleic acid or groups introduced as a consequence of modifying the RNA (imidazole), there are several counter SELEX™ methods.

DNase I digestion of the DNA-PEG linker is the most efficient method for removing products between the nucleic acid-reactant test mixture (acetophenone-PEG-DNA-RNA) that do not involve the first reactant. All biotinylated products will be attached to streptavidin on magnetic beads. Following the multiple washing steps to remove any unbound nucleic acid-reactant, the magnetic beads (with bound biotinylated RNAs) are resuspended in 200 µl of DNase I buffer. DNAse I (4 units; RNase free) is added and the DNA is digested for 30 min at 37° C. The beads are placed in the MPC and the RNA that is released is collected in the supernatant. The beads are washed several times to remove any unbound RNA. The supernatant and washes contain only RNA that was attached to streptavidin by the product formed by reaction of the acetophenone and biotin-4-nitrophenol. The RNA solution is phenol/chloroform extracted to remove DNase and placed in the speed vac to dry. The RNA is resuspended in water and reverse transcribed. The cDNA is PCR amplified to make double-stranded DNA product for the next round of transcription.

Alternatively, the counter-SELEX™ method can involve a subtraction step where RNA is ligated to another reactant-PEG-DNA$_{10mer}$, i.e., a diene in the case of the Claisen condensation. This RNA is allowed to react with the second reactant (biotin-4-nitrophenol) under the same conditions as the acetophenone-PEG-DNA-RNA. The RNA that does not bind to the streptavidin-coated magnetic beads is now passed through a NAP-10 column to remove salt, dried in the speed vac, resuspended in water and reverse transcribed The cDNA is PCR amplified and transcribed for ligation to the acetophenone-PEG-DNA$_{10mer}$ for the positive selection.

If incubation of the unligated RNA with the second reactant results in a similar amount of RNA bound to the target, then those undesired RNAs can be removed by passing this mixture over the magnetic beads. The unbound RNA would then be passed through a NAP-10 desalting column and dried in the speed vac. The RNA can then be resuspended in water and used directly in the ligation reaction with the acetophenone-PEG-DNA$_{10mer}$. The acetophenone-PEG-DNA-RNA would then be incubated with the biotin-4-nitrophenol as described above.

Example Ten

RNA-Facilitated Claisen Reaction

This example describes a Parallel SELEX™ procedure wherein the coupled reactant is an acetophenone attached via a PEG linker to a random nucleic acid test mixture as described previously in Examples 1–3. The nucleic acid test mixture included 100 nucleotides of random sequences containing either benzoyl-UTP or imidazole-UTP. The free reactant is an AMP-biotin molecule. The reaction facilitated by the RNA is a Claisen reaction between the acetophenone and the AMP moiety as shown in the scheme below.

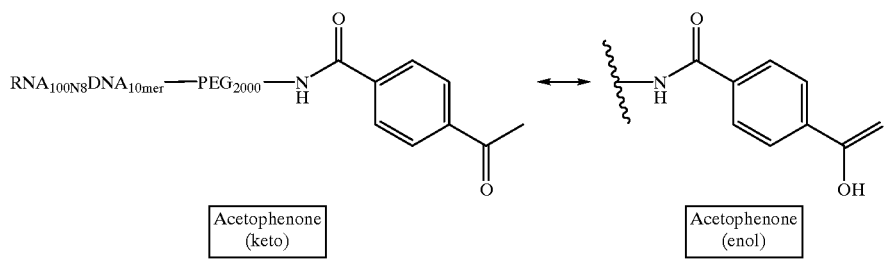

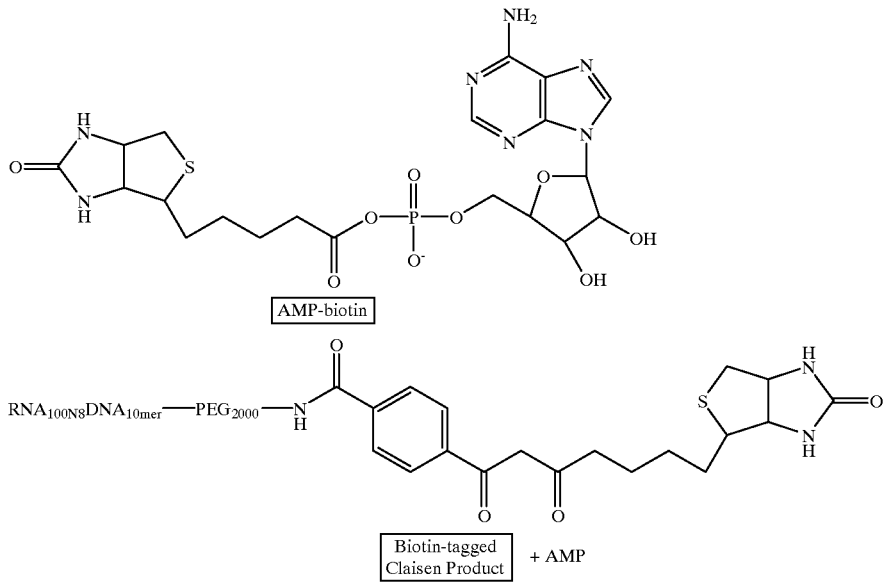

Synthesis of the Acetophenone-Nucleic Acid Test Mixture

The starting random nucleic acid test mixture is 2 nmole of 100N8 containing either benzoyl-UTP or imidazole-UTP as described in Example 1. The acetophenone nucleophile was ligated onto the RNA molecules through a DNA-PEG-linker as described in Examples 2–3. The AMP-biotin was synthesized by equal-molar incubation of AMP and biotin in the presence of excess DCC in a HCl/pyridine mixture. The AMP-biotin was purified by reverse phase HPLC and characterized by $^{31}$P-NMR.

The Reaction

The SELEX™ reaction buffer contains 200 mM HEPES (pH 7), 200 mM NaCl, 200 mM KCl, 2 mM $MgCl_2$, 2 mM $CaCl_2$, 10 μM each of $CoCl_2$, $CuCl_2$, $FeCl_2$, $MnCl_2$, $NiCl_2$, $ZnCl_2$ and the reactions were incubated at 25° C. The reaction stringency was gradually increased during the SELEX™ experiment by decreasing the RNA concentrations from 10 μM to 1 μM, the AMP-biotin concentration from 10 mM to 0.2–1 mM, and by reducing the incubation time from 16 h to 1 h. Partitioning of facilitating RNA molecules was based on the biotin-tag present on reacted molecules. Gel-shift partitioning was used in rounds 1–7 and in round 11; paramagnetic streptavidin Dynabeads M-280 were used for partitioning in rounds 8–10 and 12–14. During rounds 12–14, SELEX™ reactions of the enriched pools and the starting pools were performed side-by-side. The corresponding backgrounds were determined by incubating half of each RNA pool in the absence of AMP-biotin.

To determine if this biotinylation occurs at the terminal nucleophiles or at internal reaction centers, round 14 was carried out with either the correct terminal nucleophile or a non-reactive diene ligated onto the RNA molecules. This comparison indicates that RNA molecules with acetophenone as the terminal nucleophile are mostly internally biotinylated. RNA molecules facilitating internal biotinylation will be deleted from the pools by counter-SELEX™ methods as described in Example Nine. The SELEX™ pools will be further enriched for RNA molecules facilitating biotinylation of the terminal nucleophiles by continued rounds with increasing reaction stringency.

Example Eleven

RNA-Facilitated Amidation Reaction

This example describes a Parallel SELEX™ procedure wherein the coupled reactant is an amine attached via a PEG linker to a random nucleic acid test mixture prepared as described in Examples 1–3. The nucleic acid test mixture included 100 nucleotides of random sequences containing either benzoyl-UTP or imidazole-UTP. The free reactant is an AMP-biotin molecule. The reaction facilitated by the RNA is a reaction between the amine and the AMP moiety as shown in the scheme below.

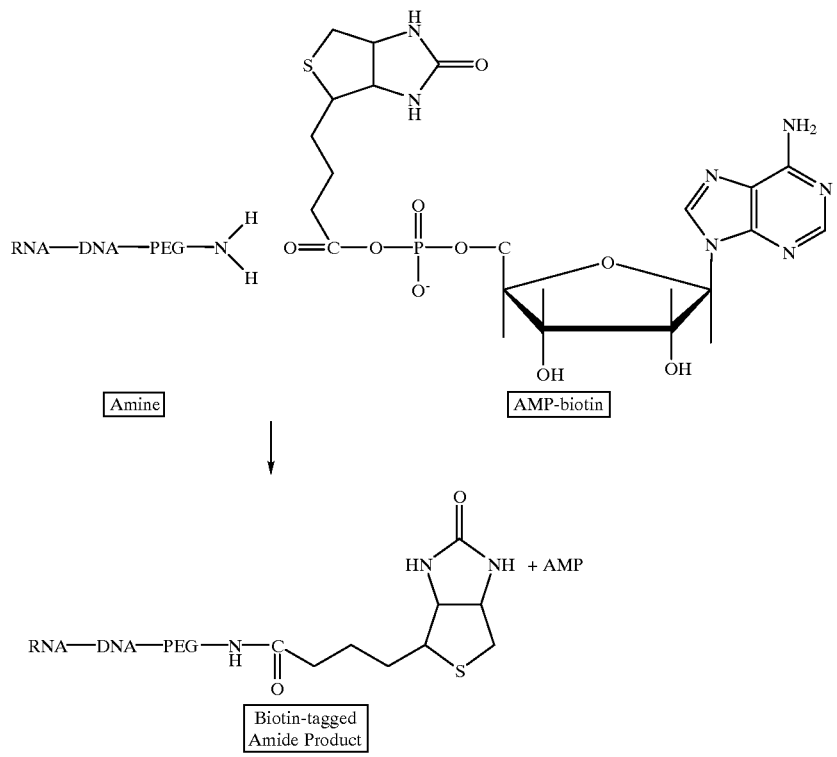

Synthesis of the Amine-RNA Library

The starting random nucleic acid test mixture is 2 nmole of 100N8 containing either benzoyl-UTP or imidazole-UTP as described in Example One. The amine nucleophile was ligated onto the RNA molecules through a DNA-PEG-linker similar to the description provided in Example 1–3.

The AMP-biotin was synthesized by equal-molar incubation of AMP and biotin in the presence of excess DCC in a HCl/pyridine mixture. The AMP-biotin was purified by reverse phase HPLC and characterized by $^{31}$P-NMR.

The Reaction

The SELEX™ reaction buffer contains 200 mM HEPES (pH 7), 200 mM NaCl, 200 mM KCl, 2 mM MgCl$_2$, 2 mM CaCl$_2$, 10 μM each of CoCl$_2$, CuCl$_2$, FeCl$_2$, MnCl$_2$, NiCl$_2$, ZnCl$_2$ and the reactions were incubated at 25° C. The reaction stringency was gradually increased during the SELEX™ experiment by decreasing the RNA concentrations from 10 μM to 1 μM, the AMP-biotin concentration from 10 mM to 0.2–1 mM, and by reducing the incubation time from 16 h to 1 h. Partitioning of facilitating RNA molecules was based on the biotin-tag present on reacted molecules. Gel-shift partitioning was used in rounds 1–7 and in round 11; paramagnetic streptavidin Dynabeads M-280 were used for partitioning in rounds 8–10 and 12–14. During rounds 12–14, SELEX™ reactions of the enriched pools and the starting pools were performed side-by-side. The corresponding backgrounds were determined by incubating half of each RNA pool in the absence of AMP-biotin.

To determine if this biotinylation occurs at the terminal amine nucleophile or at internal reaction centers, round 14 was carried out with either the correct terminal amine nucleophile or a non-reactive diene ligated onto the RNA molecules. This comparison indicates that biotinylation of imidazole-UTP RNA molecules occurs preferentially on the terminal amine. RNA molecules facilitating internal biotinylation will be deleted from the pools by counter-SELEX™ methods as described in Example Nine. The SELEX™ pools will be further enriched for RNA molecules facilitating biotinylation of the terminal nucleophiles by continued rounds with increasing reaction stringency.

Example Twelve

Use of Unmodified and 5-Imidazol-UMP-Modified RNA to Facilitate an Acylation Reaction: Selection of Human Neutrophil Elastase Inhibitors from an NHS-Carbamate-Functionalized Peptide Library An additional application of the Parallel SELEX™ methodology involves the selection of inhibitors of the serine protease human neutrophil elastase (HNE) from a large NHS-carbamate-functionalized peptide library using unmodified or 5-imidazol-UMP-modified RNA conjugated to a primary amine. This application addresses the deconvolution of a pre-synthesized combinatorial library. RNAs capable of facilitating a reaction (acylation) between their attached nucleophilic primary amine and the electrophilic carbonyl carbon of NHS-carbamates would be selected on the basis of the ability of the resulting RNA-conjugated peptide to interact with HNE. A more detailed description of this Parallel SELEX™ experiment, which is currently in progress, is provided below.

Synthesis of NHS-carbamate-functionalized peptide-diphenylphosphonate library

Certain peptidyl derivatives of diphenyl(α-aminoalkyl) phosphonates have been shown to be effective irreversible (covalent) inhibitors of HNE (J. Oleksyszyn and J. C. Powers. 1991. Irreversible inhibition of serine proteases by peptide derivatives of (α-aminoalkyl)phosphonate diphenyl esters. Biochemistry 30: 485–493). Using the known weak inhibitor Val$^P$(OPh)$_2$ as a starting point, a library of approximately 250,000 different tetrapeptide diphenylphosphonates was synthesized by standard solution phase combinatorial split synthesis. The symmetrical anhydrides of 50 different Boc-protected amino acids were synthesized, characterized by IR spectroscopy and reacted with amino phosphonate 6 shown in the scheme below. The reactions were combined to give the ca 100 compound mixture 7 which had $^1$H and $^{31}$P resonances consistent with a Boc-dipeptide mixture. The mixture 7 was converted to the free amines 8, divided into 50 equal portions and treated with each of the 50 anhydrides to form the 5K library 9. The process was repeated once to complete the peptide library. The resulting deprotected peptides were derivatized as the NHS carbamates.

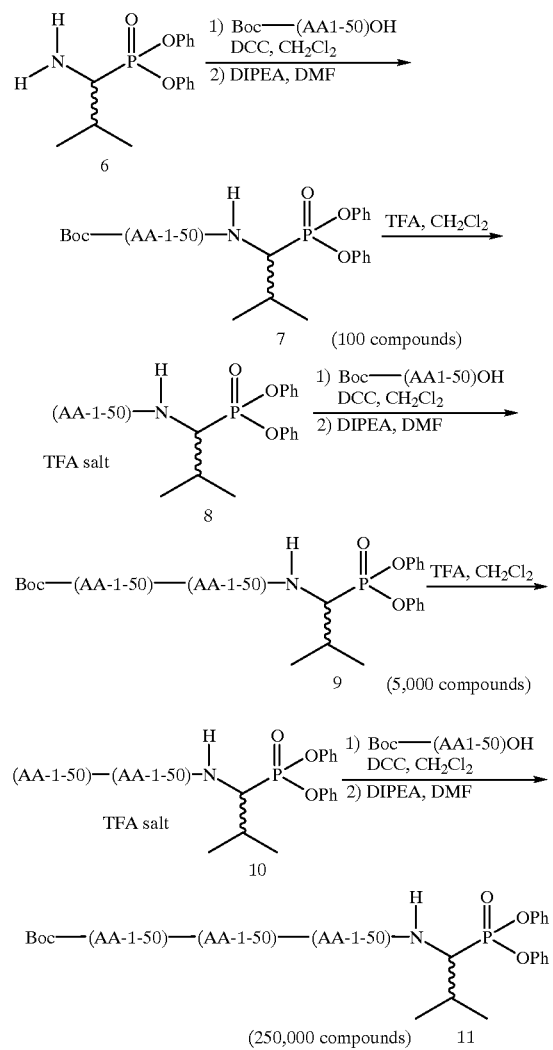

RNA pools

Random sequence RNA pools (100N; 100 nucleotides of contiguous random sequence; unmodified or 5-imidazole-U-modified) were ligated to DNA-PEG-NH$_2$ as described above in Examples 1–3.

Reaction of RNA-NH$_2$ pool with NHS-carbamate-functionalized peptide library

For each RNA pool, the initial reaction (given as an example of a typical reaction) consisted of approximately 2 nmoles RNA-NH$_2$ and 100 nmoles of NHS-carbamate functionalized peptides in 200 μl of reaction buffer (20% v/v methanol, 100 mM NaCl, 10 mM KCl, 1 mM MgCl$_2$, 1 mM CaCl$_2$, 100 μM MnCl$_2$, 10 μM CuSO$_4$, 10 μM ZnCl$_2$, 10 μM CoCl$_2$, 10 μM NiCl$_2$, 50 mM HEPES, pH 7.5). Following a 16 hour incubation at 22° C. peptides were removed from the RNA solution by size exclusion chromatography. The RNAs were further purified by retention on a 30,000 molecular weight cut-off (MWCO) microcentrifuge spin filter followed by extensive washing to remove any remaining free peptides.

To prevent the selection of RNA sequences on the basis of their affinity for HNE, the recovered RNAs were reverse-transcribed using an RNaseH negative reverse transcriptase (Superscript; GibcoBRL) to produce double-stranded RNA/cDNA hybrids.

Selection of RNA-conjugated HNE inhibitors—Methods for the effective selection of RNA-conjugated HNE inhibitors have been fully characterized. These methods exploit either the differential mobility of free RNA and HNE-conjugated RNA on denaturing polyacrylamide gels, or the specific retention of RNA-conjugated HNE inhibitors on bead-coupled HNE. While agarose bead (Sepharose 6B)-coupled HNE was used to select RNA-conjugated HNE inhibitors in the first selection cycle, each of the methods described below can be used throughout the selection process to ensure that the RNA population becomes enriched only with RNAs which facilitate the acylation reaction with NHS carbamate-functionalized HNE inhibitors (i.e., by alternating between different partitioning methods, the RNA population should not be enriched with nucleic acids retained for reasons other than having an attached HNE inhibitor).

For gel mobility shift partitioning, the recovered RNAs are combined with excess HNE in HNE reaction buffer (1 M NaCl, 0.01% Triton X-100, 50 mM HEPES, pH 7.5) and incubated for 30 min at room temperature. Two volumes of gel loading buffer (7 M urea, 50% v/v formamide, 0.05% SDS, 20 mM potassium phosphate, 1 mM EDTA, 0.1% w/v each of xylene cyanol and bromophenol blue) are added to the reaction mixture followed by electrophoresis on a denaturing polyacrylamide gel [5% acrylamide (19:1 acrylamide:bis-acrylamide), 7 M urea, 50% v/v formamide, 0.05% SDS, 20 mM potassium phosphate, 1 mM EDTA] with 20 mM potassium phosphate/1 mM EDTA as the running buffer. Following electrophoresis, RNA-HNE conjugates are identified by autoradiography and recovered by standard methods.

Two methods for partitioning RNA-conjugated HNE inhibitors with bead-coupled HNE have been developed. In the first method, HNE was conjugated to Sepharose 6B via a cleavable linker. More specifically, thiopropyl-Sepharose 6B (Sigma; pyridyldithiol linker arm) was converted to thiol-Sepharose 6B by reducing the linker arms with DTT. After removal of DTT, the thiol-functionalized beads were reacted with 3-(2-pyridyldithiol)propionyl hydrazide (PDPH; Pierce), resulting in hydrazide-functionalized beads with a disulfide-containing linker arm susceptible to cleavage with reducing agents. Sodium metaperiodate-oxidized HNE was then coupled to the beads through the hydrazide groups. HNE coupled to Sepharose beads by this procedure retain full activity and effectively retain RNA-conjugated HNE inhibitors. Resulting RNA-HNE conjugates can be eluted from the beads by cleavage of the linker arms with DTT (150 mM NaCl, ≧100 mM DTT, 50 mM HEPES, pH 7.5). The specific elution of HNE prevents the retention of nucleic acids which interact with components of the matrix other than HNE.

HNE has also been coupled to streptavidin-coated superparamagnetic beads (Dynabeads (Dynal)) exhibit magnetic properties only when placed within a magnetic field). Important for this particular application, these uniformly-sized polystyrene (with an even dispersion of Fe$_2$O$_3$) beads exhibit very low non-specific binding to nucleic acids. The coupling of HNE was accomplished by first biotinylating sodium metaperiodate-oxidized HNE with biotin-LC-hydrazide (Pierce), followed by the addition of biotin-HNE to the streptavidin-coated beads. HNE coupled by this procedure are also fully effective at retaining RNA-conjugated HNE inhibitors. Due to their very low non-specific binding properties, HNE-conjugated RNAs can be directly amplified in the presence of the beads.

With each of the described partitioning methods, the best HNE inhibitors can be preferentially selected during the SELEX™ process by increasing the stringency of the binding reaction; this can be accomplished, for example, by reducing the concentrations of the reactants, by reducing the time of incubation, or by demanding that the RNA-conjugated HNE inhibitors compete with reversible HNE inhibitors for binding to HNE. The selection/amplification process will be repeated until the RNA pools are sufficiently enriched in facilitating RNAs to permit identification of their specifically attached HNE inhibitors.

We claim:

1. A method for producing a product having the ability to perform a preselected function on a target comprising:

(a) preparing a nucleic acid test mixture, wherein said nucleic acid test mixture comprises nucleic acids having one or more functional groups selected from the group consisting of

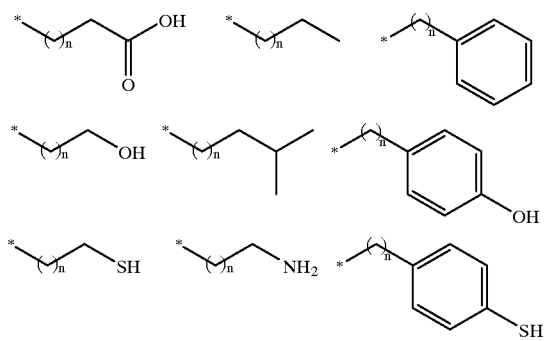

-continued

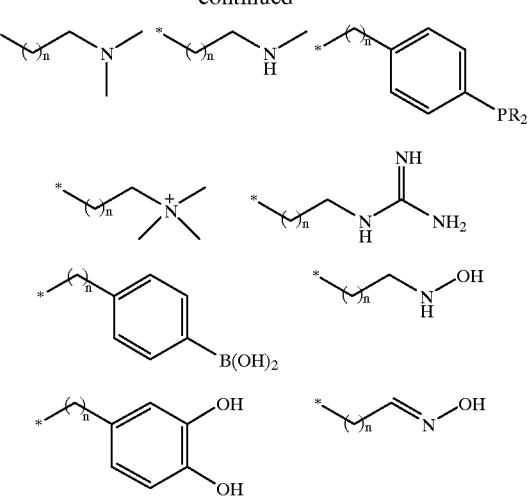

-continued

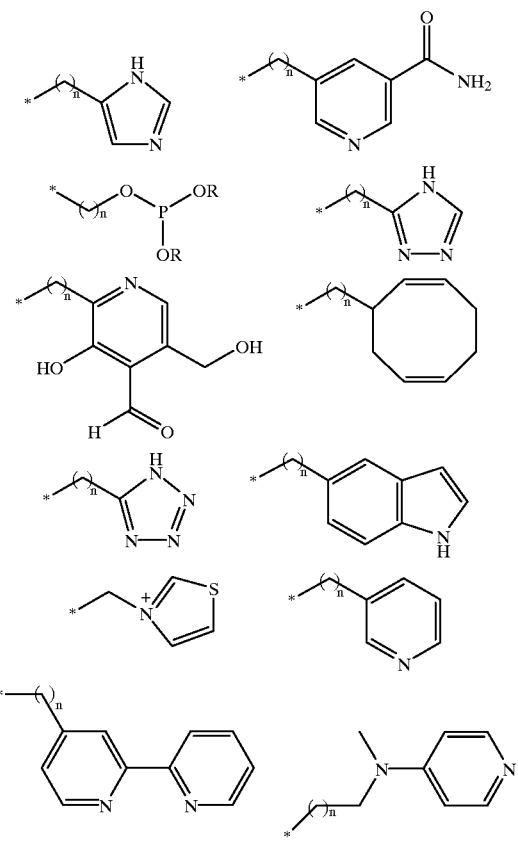

wherein the asterisk indicates the point of attachment of the functional group to the nucleic acid, n may be any integer and wherein said functional groups may be substituted at aliphatic or aromatic positions;
(b) coupling each member of said nucleic acid test mixture with a first reactant to form a nucleic acid-first reactant test mixture;
(c) forming a product library by contacting said nucleic acid-first reactant test mixture with a mixture of free reactants consisting of small organic molecules with a molecular weight in the range of 2 to 1000, wherein said product library is formed as a result of a bond formation reaction between said first reactant and at least one of said free reactants, wherein said bond formation reaction is facilitated by a nucleic acid coupled to said first reactant;
(d) contacting the product library of step (c) with a target, wherein the product having the ability to perform a preselected function on said target relative to the product library may be partitioned from the remainder of the product library; and
(e) partitioning said product having said ability to perform a preselected function of said target from the remainder of the product library, whereby said product can be produced.

2. The method of claim 1 wherein said nucleic acid test mixture comprises nucleic acids having a region of conserved sequences and a region of randomized sequences.

3. The method of claim 1 wherein said nucleic acid coupled to said first reactant is selected from the group consisting of single-stranded RNA, single-stranded DNA and double-stranded DNA.

4. The method of claim 1 wherein said nucleic acid text mixture comprises pyrimidines modified at the 2'- or 5-positions.

5. The method of claim 1 wherein said functional group is on a ribose position of said nucleic acid.

6. The method of claim 1 wherein said functional group is on a base position of said nucleic acid.

7. The method of claim 1 wherein said functional group is on a phosphate position of said nucleic acid.

8. The method of claim 1 which further comprises a linker group coupled between said first reactant and said nucleic acid.

9. The method of claim 8 wherein said linker group has a size in the range of 10 to 1000 D.

10. The method of claim 9 wherein said linker group is selected from the group consisting of polyethylene glycol (PEG), polyvinyl alcohol, polyacrylates and polypeptides.

11. A method for coproducing a nucleic acid that facilitates bond formation and a product that performs a preselected function on a target comprising:
(a) preparing a nucleic acid test mixture, wherein said nucleic acid test mixture comprises nucleic acids having one or more functional groups selected from the group consisting of

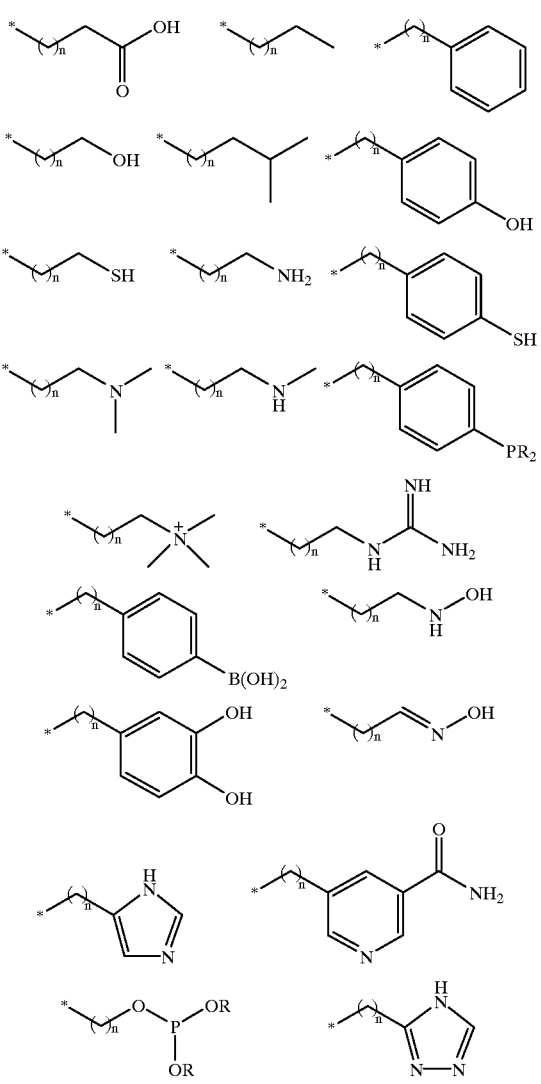

-continued

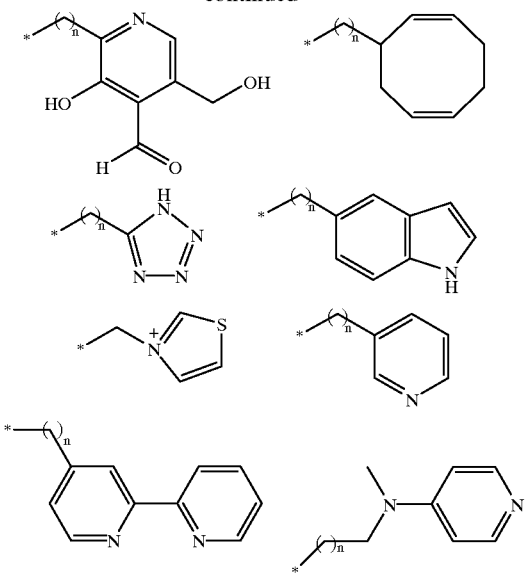

wherein the asterisk indicates the point of attachment of the functional group to the nucleic acid, n may be any integer and wherein said functional groups may be substituted at aliphatic or aromatic positions;

(b) coupling a first reactant to each member of said nucleic acid test mixture to form a nucleic acid-first reactant test mixture;

(c) forming a product library by contacting said nucleic acid-first reactant test mixture with a mixture of free reactants consisting of small organic molecules with a molecular weight in the range of 2 to 1000, wherein said product library is formed as a result of a bond formation between said first reactant and at least one of said free reactants, wherein said bond formation is facilitated by a nucleic acid which is coupled to said first reactant and wherein each product is coupled to a nucleic acid;

(d) contacting said product library with a target, wherein products that perform a preselected function on said target relative to the product library may be partitioned from the remainder of the product library; and (e) amplifying the nucleic acid associated with the product that performs a preselected function on said target, to yield a mixture of nucleic acids enriched for nucleic acids that facilitate bond formation between said first reactant and said free reactant, whereby said nucleic acid that facilitates bond formation and said product are produced.

12. The method of claim 11 which further comprises:

(f) coupling the amplified nucleic acids with said first reactant; and (g) repeating steps (c) through (f) until the product that performs said preselected function on said target can be produced in sufficient quantity for structure determination.

13. The method of claim 11 wherein said nucleic acid test mixture comprises nucleic acids having a region of conserved sequences and a region of randomized sequences.

14. The method of claim 11 wherein said nucleic acid coupled to said first reactant is selected from the group consisting of single-stranded RNA, single-stranded DNA and double-stranded DNA.

15. The method of claim 11 wherein said functional group is on a ribose position of said nucleic acid.

16. The method of claim 11 wherein said functional group is on a base position of said nucleic acid.

17. The method of claim 11 wherein said functional group is on a phosphate position of said nucleic acid.

18. The method of claim 11 which further comprises a linker group coupled between said first reactant and said nucleic acid.

19. The method of claim 18 wherein said linker group has a size in the range of 10 to 1000 D.

20. The method of claim 19 wherein said linker group is selected from the group consisting of PEG, polyvinyl alcohol, polyacrylates and polypeptides.

21. A method for producing a product library comprising contacting a mixture of first reactants each coupled to a member of a nucleic acid test mixture with a mixture of free reactants, wherein said nucleic acid test mixture comprises nucleic acids having one or more functional groups selected from the group consisting of

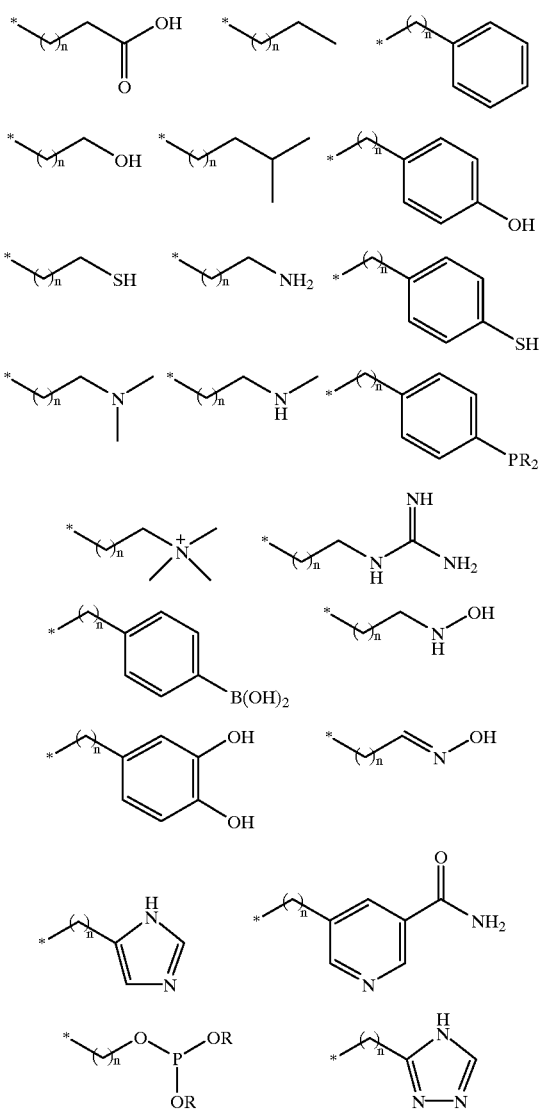

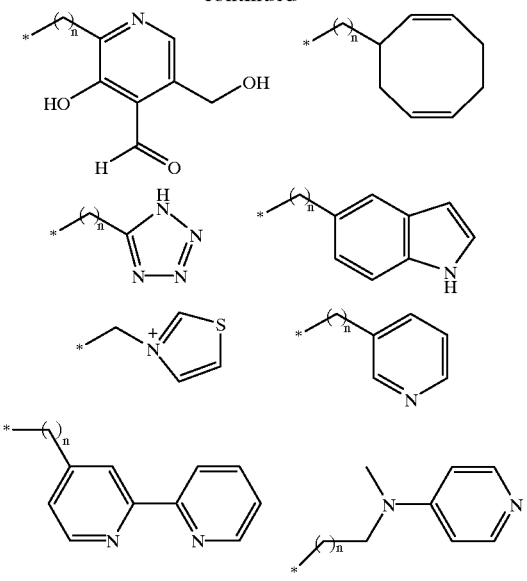

wherein the asterisk indicates the point of attachment of the chemical group to the nucleic acid, n may be any integer and wherein said chemical groups may be substituted at aliphatic or aromatic positions, each of first and free reactants consisting of a small organic molecule with a molecular weight in the range of 2 to 1000, wherein said product library is formed as a result of a bond formation reaction between said first reactant and at least one of said free reactants, wherein said bond formation reaction is facilitated by the nucleic acid coupled to said first reactant.

22. The method of claim 21 wherein said functional group is on a ribose position of said nucleic acid.

23. The method of claim 21 wherein said functional group is on a base position of said nucleic acid.

24. The method of claim 21 wherein said functional group is on a phosphate position of said nucleic acid.

25. The method of claim 21 which further comprises a linker group coupled between said first reactant and said nucleic acid.

26. The method of claim 25 wherein said linker group has a size in the range of 10 to 1000 D.

27. The method of claim 26 wherein said linker group is selected from the group consisting of PEG, polyvinyl alcohol, polyacrylates and polypeptides.

* * * * *

```
                          SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
         (A) LENGTH:  10
         (B) TYPE:  nucleic acid
         (C) STRANDEDNESS:  single
         (D) TOPOLOGY:  linear (xi) SEQUENCE DESCRIPTION:  SEQ ID NO:1:

CCAGGCACGC                                                              10

(2) INFORMATION FOR SEQ ID NO:2:

(i) SEQUENCE CHARACTERISTICS:
         (A) LENGTH:  87
         (B) TYPE:  nucleic acid
         (C) STRANDEDNESS:  single
         (D) TOPOLOGY:  linear (xi) SEQUENCE DESCRIPTION:  SEQ ID NO:2:

GGGAGACAAG AATAAACGCT CAANNNNNNN NNNNNNNNNN NNNNNNNNNN                   50

NNNNNNNNNN NNNTTCGACA GGAGGCTCAC AACAGGC                                 87

(2) INFORMATION FOR SEQ ID NO:3:

(i) SEQUENCE CHARACTERISTICS:
         (A) LENGTH: 20
         (B) TYPE:  nucleic acid
         (C) STRANDEDNESS:  single
         (D) TOPOLOGY:  linear (xi) SEQUENCE DESCRIPTION:  SEQ ID NO:3:

CTTGTCTCCC GCGTGCCTGG                                                   20

(2) INFORMATION FOR SEQ ID NO:4:

(i) SEQUENCE CHARACTERISTICS:
         (A) LENGTH: 77
         (B) TYPE:  nucleic acid
         (C) STRANDEDNESS:  single
         (D) TOPOLOGY:  linear (xi) SEQUENCE DESCRIPTION:  SEQ ID NO:4:

GGGAGCUCAG AAUAAACGCU CAANNNNNNN NNNNNNNNNN NNNNNNNNNN                   50

NNNUUCGACA UGAGGCCCGG AUCCGGC                                           77

(2) INFORMATION FOR SEQ ID NO:5:
```

```
        (i) SEQUENCE CHARACTERISTICS:
            (A) LENGTH: 78
            (B) TYPE:  nucleic acid
            (C) STRANDEDNESS:  single
            (D) TOPOLOGY:  linear (xi) SEQUENCE DESCRIPTION:  SEQ ID NO:5:

GGGAGCUCAG AAUAAACGCU CAAAGCUGUU GGCAGCGCUG GUGAAGGGAU                50

AGGCUUCGAC AUGAGGCCCG GAUCCGGC                                        78

(2) INFORMATION FOR SEQ ID NO:6:

(i) SEQUENCE CHARACTERISTICS:
            (A) LENGTH: 147
            (B) TYPE:  nucleic acid
            (C) STRANDEDNESS:  single
            (D) TOPOLOGY:  linear (xi) SEQUENCE DESCRIPTION:  SEQ ID NO:6:

GGGAGACAAG AATAAACGCT CAANNNNNNN NNNNNNNNNN NNNNNNNNNN                50

NNNNNNNNNN NNNNNNNNNN NNNNNNNNNN NNNNNNNNNN NNNNNNNNNN               100

NNNNNNNNNN NNNNNNNNNN NNNTTCGACA GGAGGCTCAC AACAGGC                  147

(2) INFORMATION FOR SEQ ID NO:7:

(i) SEQUENCE CHARACTERISTICS:
            (A) LENGTH: 147
            (B) TYPE:  nucleic acid
            (C) STRANDEDNESS:  single
            (D) TOPOLOGY:  linear (xi) SEQUENCE DESCRIPTION:  SEQ ID NO:7:

GGGAGACAAG AATAAACGCT CAANNNNNNN NNNNNNNNNN NNNNNNNNNN                50

NNNNNNNNNN NNNNNNNNNN NNNNNNNNNN NNNNNNNNNN NNNNNNNNNN               100

NNNNNNNNNN NNNNNNNNNN NNNTTGAGCG TGAGGCTACT AACAGGC                  147
```